US011261231B2

(12) United States Patent
Jones et al.

(10) Patent No.: US 11,261,231 B2
(45) Date of Patent: Mar. 1, 2022

(54) METHODS FOR INHIBITING HIV OR HCV INFECTION BY ADMINISTERING TIM-3 BINDING INHIBITORS

(71) Applicants: The Regents of the University of California, San Francisco, CA (US); Altor Bioscience, LLC, Miramar, CA (US)

(72) Inventors: Richard B. Jones, Toronto (CA); Mario Ostrowski, Toronto (CA); Douglas F. Nixon, San Francisco, CA (US); Lishomwa C. Ndhlovu, San Francisco, CA (US); James Rini, New York (CA)

(73) Assignees: Altor BioScience, LLC., Culver City, CA (US); The Regents of the University of Califoria, San Francisco, CA (US)

( * ) Notice: Subject to any disclaimer, the term of this patent is extended or adjusted under 35 U.S.C. 154(b) by 0 days.

(21) Appl. No.: 15/208,924

(22) Filed: Jul. 13, 2016

(65) Prior Publication Data
US 2016/0311890 A1 Oct. 27, 2016

Related U.S. Application Data

(62) Division of application No. 12/739,639, filed as application No. PCT/CA2008/001873 on Oct. 27, 2008, now Pat. No. 9,416,164.

(60) Provisional application No. 60/982,771, filed on Oct. 26, 2007.

(51) Int. Cl.
| | | |
|---|---|---|
| C07K 14/705 | (2006.01) | |
| C07K 16/28 | (2006.01) | |
| G01N 33/68 | (2006.01) | |
| G01N 33/569 | (2006.01) | |
| G01N 33/576 | (2006.01) | |
| C07K 16/10 | (2006.01) | |

(52) U.S. Cl.
CPC .... *C07K 14/70503* (2013.01); *C07K 16/2803* (2013.01); *G01N 33/6863* (2013.01); *G01N 33/6866* (2013.01); *C07K 16/1009* (2013.01); *C12N 2740/16011* (2013.01); *C12N 2770/24211* (2013.01); *G01N 33/56988* (2013.01); *G01N 33/576* (2013.01); *G01N 2333/525* (2013.01); *G01N 2333/57* (2013.01); *G01N 2800/52* (2013.01); *G01N 2800/56* (2013.01)

(58) Field of Classification Search
CPC .......... C07K 14/70503; C07K 16/2803; C12N 2740/16011
See application file for complete search history.

(56) References Cited

U.S. PATENT DOCUMENTS 9,416,165 B2   8/2016 Jones et al.

FOREIGN PATENT DOCUMENTS

| WO | 2003/063792 | 8/2003 |
|---|---|---|
| WO | 05/027854 | 3/2005 |
| WO | WO 2005/027854 A2 * | 3/2005 |
| WO | 05/334144 | 4/2005 |
| WO | 2005/097211 | 10/2005 |

OTHER PUBLICATIONS

Herbeuval, J.-P., and G. M. Shearer, 2007, HIV-1 immunopathogenesis: How good interferon turns bad, Clin. Immunol. 123:121-128 (available online Nov. 16, 2006).*
Cadogan, M., and A. G. Dalgleish, Nov. 2008, HIV immunopathogenesis and strategies for intervention, The Lancet 8(11):675-686.*
Burton, C. T., et al., 2011, Altered phenotype of regulatory T cells associated with lack of human immunodeficiency virus (HIV)-1-specific suppressive function, Clin. Exp. Immunol. 166(2):191-200.*
Zeng, M., et al., 2012, Lymphoid tissue structure and HIV-1 infection: life or death for T cells, Trends Immunol. 33(6):306-314.*
Alexander, H., et al., Apr. 1992, Altering the antigenicity of proteins, Proc. Natl. Acad. Sci. USA 89:3352-3356.*
Tainer, J. A., et al., 1991, Defining antibody-antigen recognition: Towards engineered antibodies and epitopes, Intern. Rev. Immunol. 7:165-188.*
Addo et al., "Up-regulation of Tim-3 expression on T cells from HIV-1 infected individuals", X VII International AIDS Conference, Mexico City; Aug. 3-8, 2008 [Abstract].
Fukushima et al., "Antibodies to T-cell and mucin domain-containing proteins (Timi)-1 and -3 suppress the induction and progression of murine allergic conjunctivitis", BBRC, 353: 211-216 (2006).
Geng et al., "Soluble form of T cell Ig mucin 3 is an inhibitory molecule in T cell-mediated immune response", The Journal of Immunology, 176(3): 1411-1420 (2006).
Hafler et al., "TIMs: central regulations of immune responses", J. Exp. Med., 205: 2699-2701 (2008).
Kearley et al., "Th-2 driven, allergen-induced airway inflammation is reduced after treatment with anti-Tim-3 antibody in vivo", The Journal of Experimental Medicine, 204(4): 1289-1294 (2007).
Sui et al., "Human membrane protein Tim-3 facilitates hepatitis a virus entry into target cells", International Journal of Molecular Medicine, 17: 1093-1099 (2006).

(Continued)

*Primary Examiner* — Jeffrey S Parkin
(74) *Attorney, Agent, or Firm* — Sheridan Ross P.C.

(57) ABSTRACT

The application relates to methods of treating chronic viral infection by modulating Tim-3 activity. In addition, the present application relates to methods of diagnosing or monitoring immune system activity or function, chronic viral infection and inflammatory disease using Tim-3 expression.

7 Claims, 27 Drawing Sheets
Specification includes a Sequence Listing.

(56) References Cited

OTHER PUBLICATIONS

Frisancho-Kiss et al., "Cutting Edge: T cell Ig Mucin-3 Reduces Inflammatory Heart Disease by Increasing CTLA-4 during Innate Immunity", Journal of Immunology, American Association of Immunologists, US, 176: 6411-6415 (2006).
Jones et al., "Tim-3 expression defined a novel population of dysfunctional T cells with highly elevated frequencies in progressive HIV-1 infection", The Journal of Experimental Medicine, 205(12): 2763-2779 (2008).
Ndhlovu et al., "Tim-3 Expression Defines a Novel Population of T Cells with Highly Elevated Frequencies in Progressive HIV-1 Infection", Aids Research and Human Retroviruses, vol. 24, No. Suppl. 1, 123 (2008).
Hartt Meyers, J. et al., "The TIM gene family regulates autoimmune and allergic diseases", TRENDS in Molecular Medicine, 11(8): 362-369 (2005).
Mette Ejrnaes et al., "Cure of Chronic Viral Infection by Neutralizing Antibody Treatment", Autoimmunity Reviews, 6: 267-271 (2007).
Shin et al., "CD8 T cell dysfunction during chronic viral infection", Current Opinion in Immunology, 19: 408-415 (2007).
Velu et al., "Enhancing SIV-Specific Immunity in Vivo by PD-1 Blockade", Nature, 458: 206-210 (2009).
Fourcade et al., "Upregulation of Tim-3 and PD-1 expression is associated with tumor antigen-specific CD8+ T cell dysfunction in melanoma patients", J. Exp. Med., 207(10): 2175-2186 (2010).
Takamura et al., "Premature Terminal Exhaustion of Friend Virus-Specific Effector CD8+ T Cells by Rapid Induction of Multiple Inhibitory Receptors", J. Immunol., 184: 4696-4707 (2010).
Jin et al., "Cooperation of Tim-3 and PD-1 in CD8 T-cell exhaustion during chronic viral infection", PNAS, 107(33): 14733-14738 (2010).
Lee et al., "Immunomodulator therapy: Monoclonal antibodies, fusion proteins, cytokines, and immunoglobulins", J. Allergy Clin. Immunol., 125: S314-S323 (2010).
Ngiow et al., "Prospects for TIM3-Targeted Antitumor Immunotherapy", Cancer Res., 71: 6567-6571 (2011).
Pardoll, "The blockade of immune checkpoints in cancer immunotherapy", Nature Reviews/Cancer, 12: 252-264 (2012).
Shetty et al., "PD-1 blockade during chronic SIV infection reduces hyperimmune activation and microbial ranslocation in rhesus macaques", J. Clin. Invest., 122(5): 1712-1716 (2012).
Baghdadi et al., "Combined blockade of TIM-3 and TIM-4 augments cancer vaccine efficacy against established melanomas", Cancer Immunol. Immunother., 62: 629-637 (2013).
Fourcade et al., "PD-1 and Tim-3 regulate the expansion of tumor antigen-specific CD8+ T cells induced by melanoma vaccines", Cancer Res., 36 pages (Dec. 16, 2013).
Jiang et al., "An integrated view of suppressor T cells subsets in Immunoregulation", J. Clin. Invest., 114(9): 1198-1208 (2004).
Hanabuchi et al., "Thymic stromal lympopoietin-activated plasmacytoid dendritic cells induce the generation of FOXP3+ regulatory T cells in human thymus", J. Immunol., 184: 2999-3007 (2010).
Burton, C.T. et al., "Altered phenotype of regulatory T cells associated with lack of human immunodeficiency virus (HIV)-1-specific suppressive function", Clin. Exp. Immunol., 166(2): 191-200 (2011).
Cadogan, M. et al., "HIV immunopathogenesis and strategies for intervention", The Lancet, 8(11): 675-686 (2008).
Herbeuval, J.-P. et al., "HIV-1 immunopathogenesis: How good interferon turns bad", Clin. Immunol., 123: 121-128 (2007) (available online Nov. 16, 2006).
Zeng et al., "Lymphoid tissue structure and HIV-1 infection: life or death for T cells", Trends Immunol., 33(6): 306-314.
International Search Report and Written Opinion for International (PCT) Patent Application No. PCT/CA2008/001873, dated Feb. 6, 2009, 14 pages.
International Preliminary Report on Patentability for International (PCT) Patent Application No. PCT/CA2008/001873, dated Apr. 27, 2010, 9 pages.

* cited by examiner

FIG. 1A
FIG. 1B
FIG. 1C
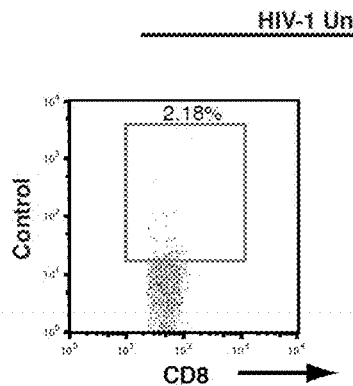
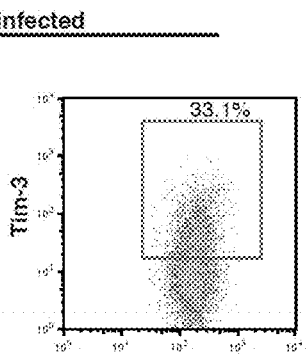
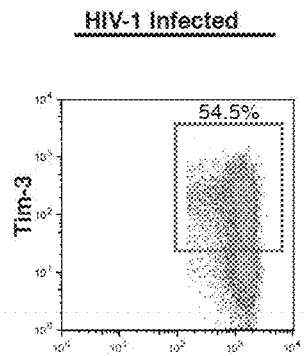
FIG. 1D
FIG. 1E
FIG. 1F
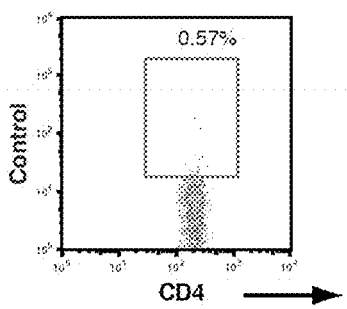
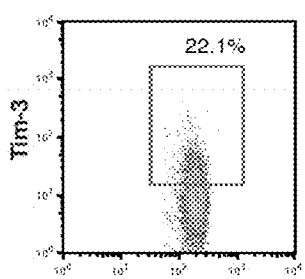
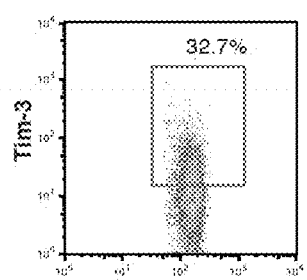
FIG. 1G
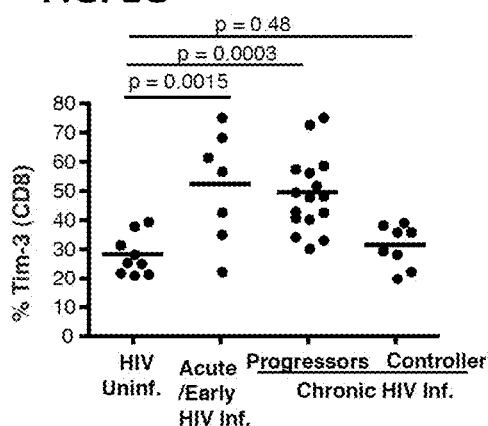
FIG. 1H
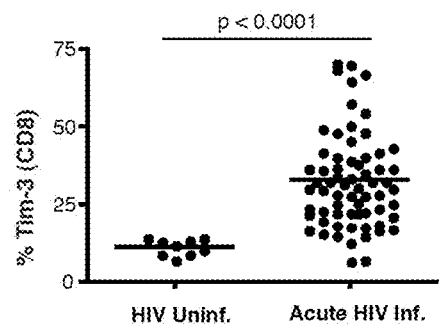
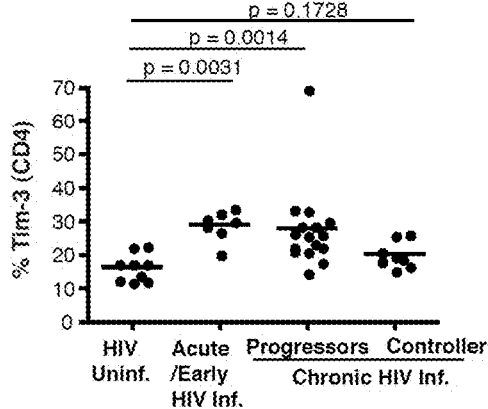
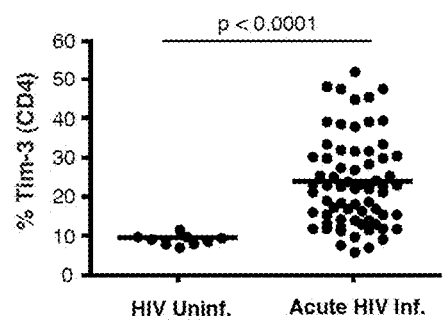

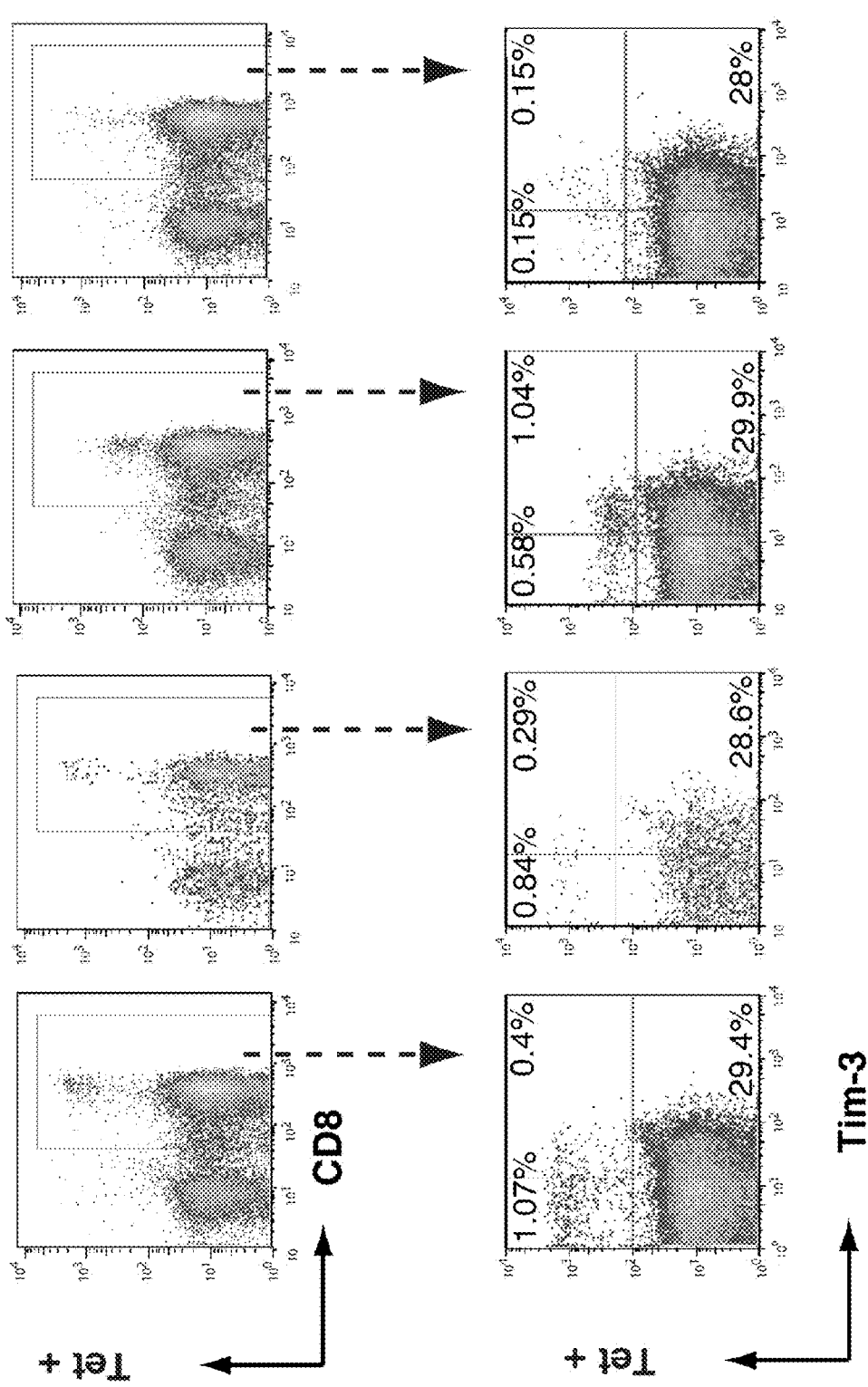

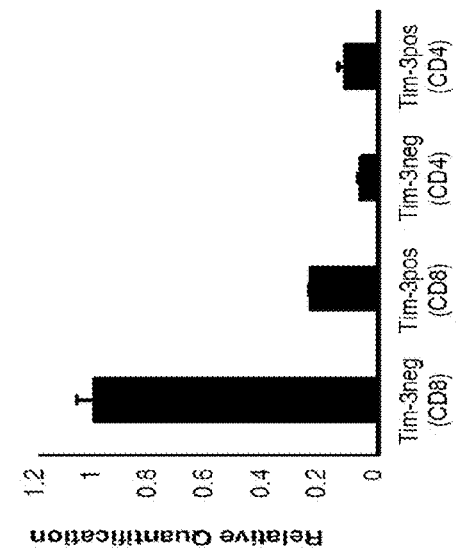
FIG. 4A  FIG. 4B  FIG. 4C
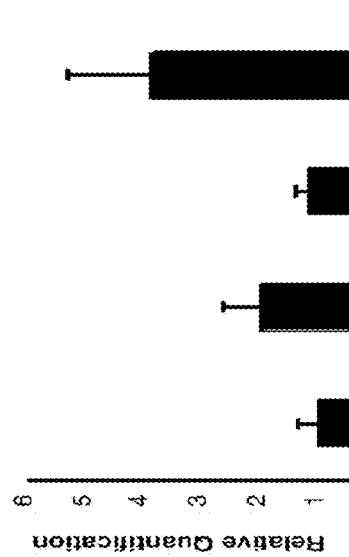
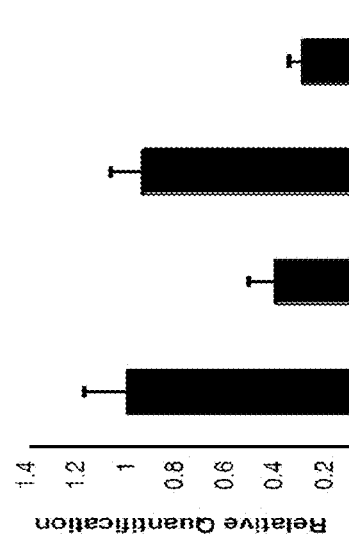

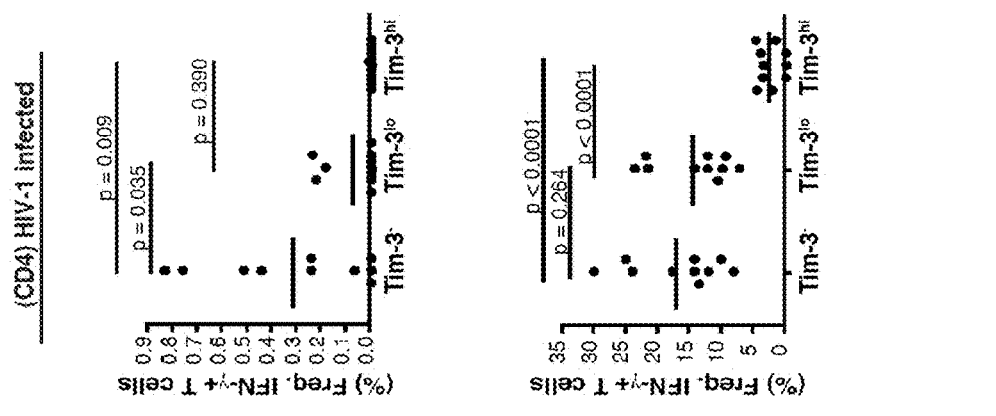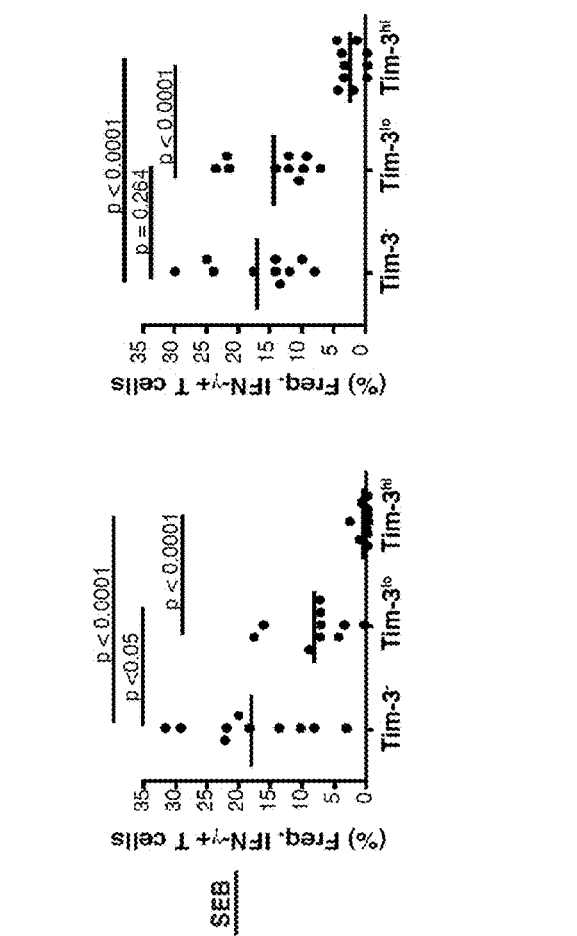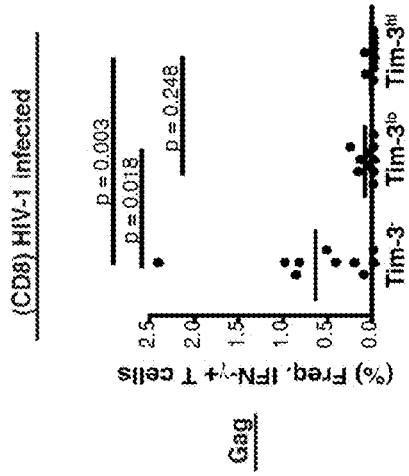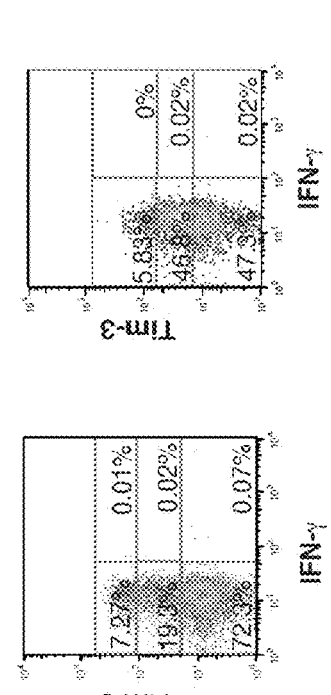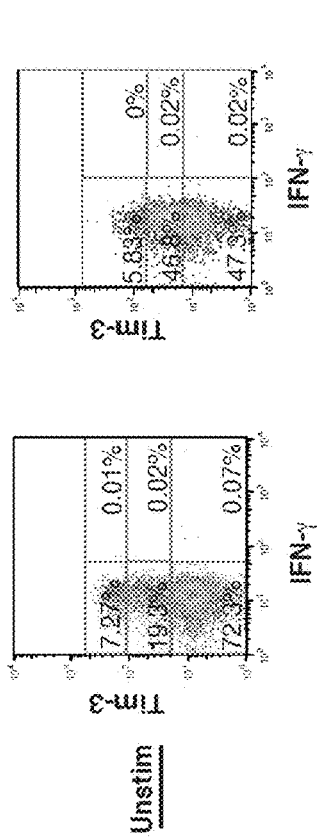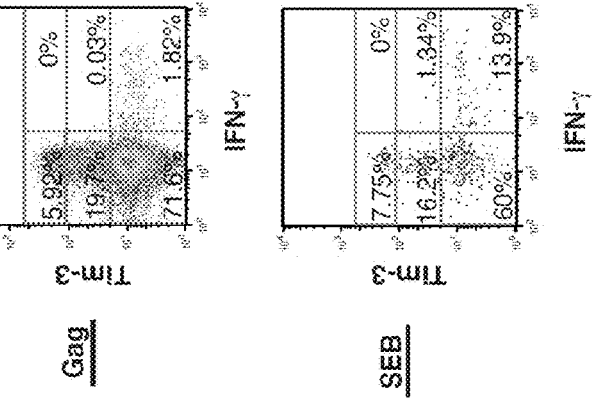

FIG. 5E
FIG. 5F
FIG. 5G
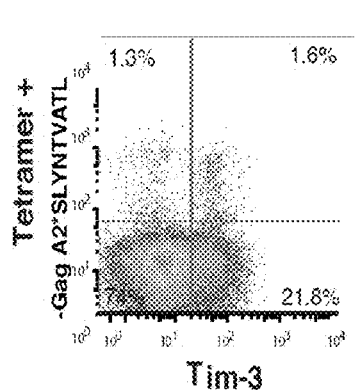
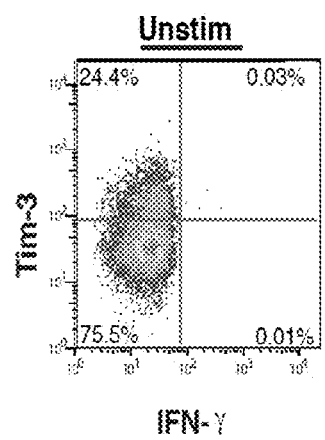
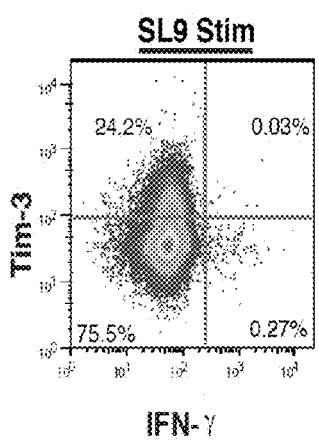
FIG. 5H
FIG. 5I
FIG. 5J
FIG. 5K
FIG. 5L
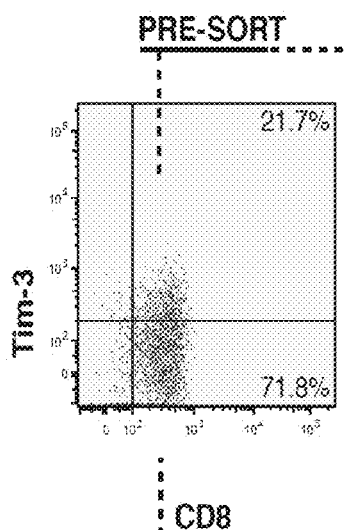
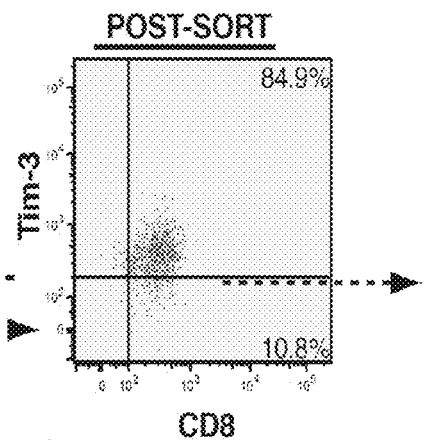
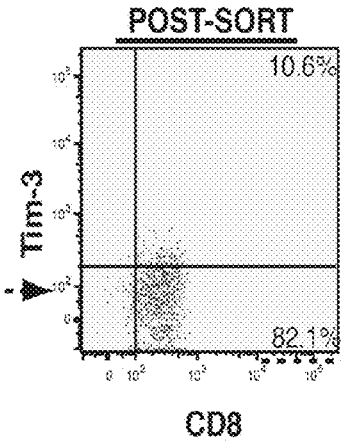
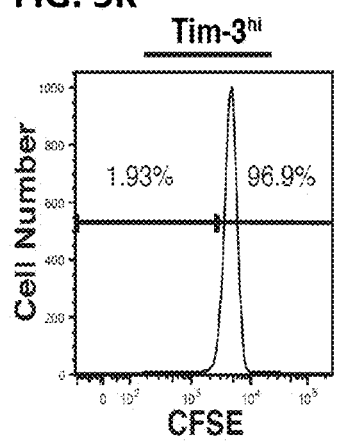
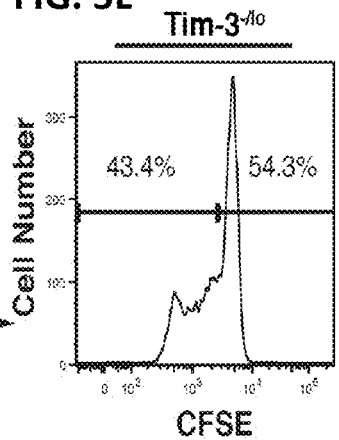

FIG. 5M   FIG. 5N   FIG. 5O   FIG. 5P
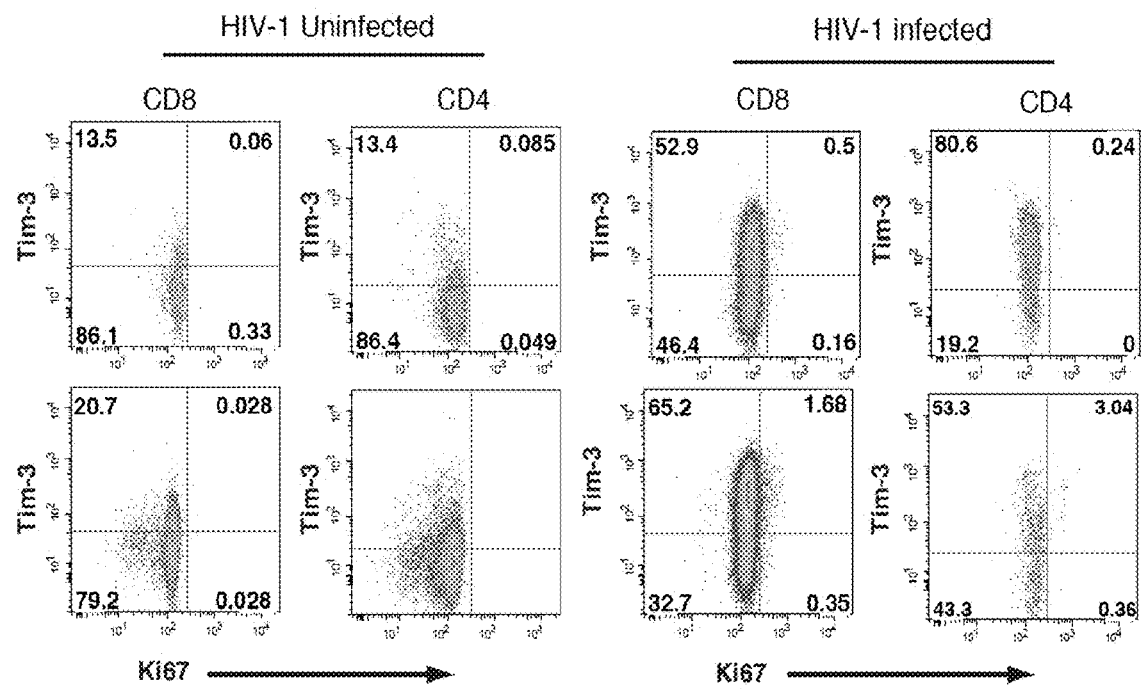
FIG. 5Q
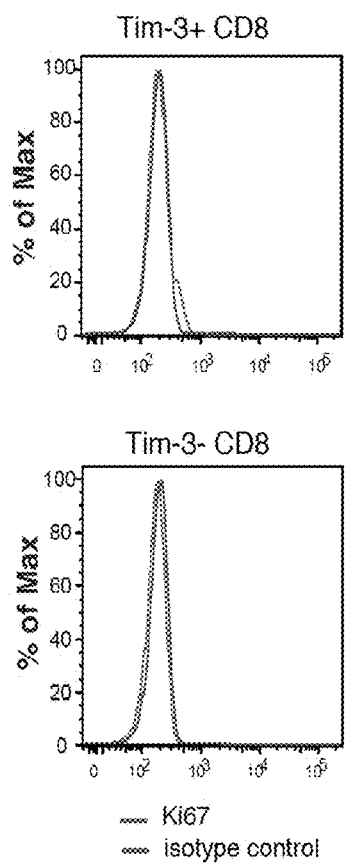
FIG. 5R
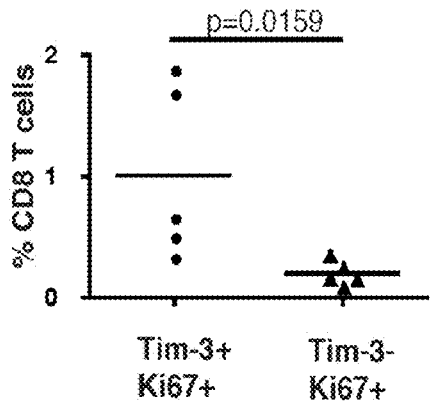

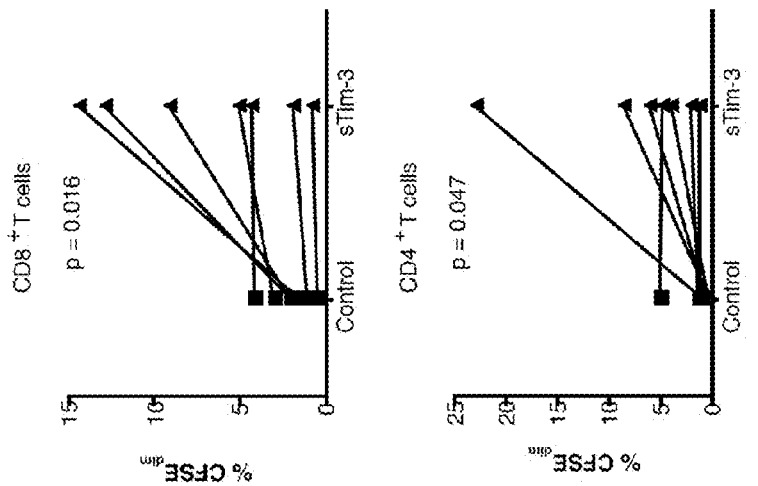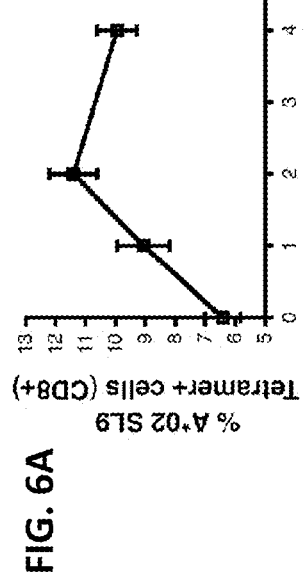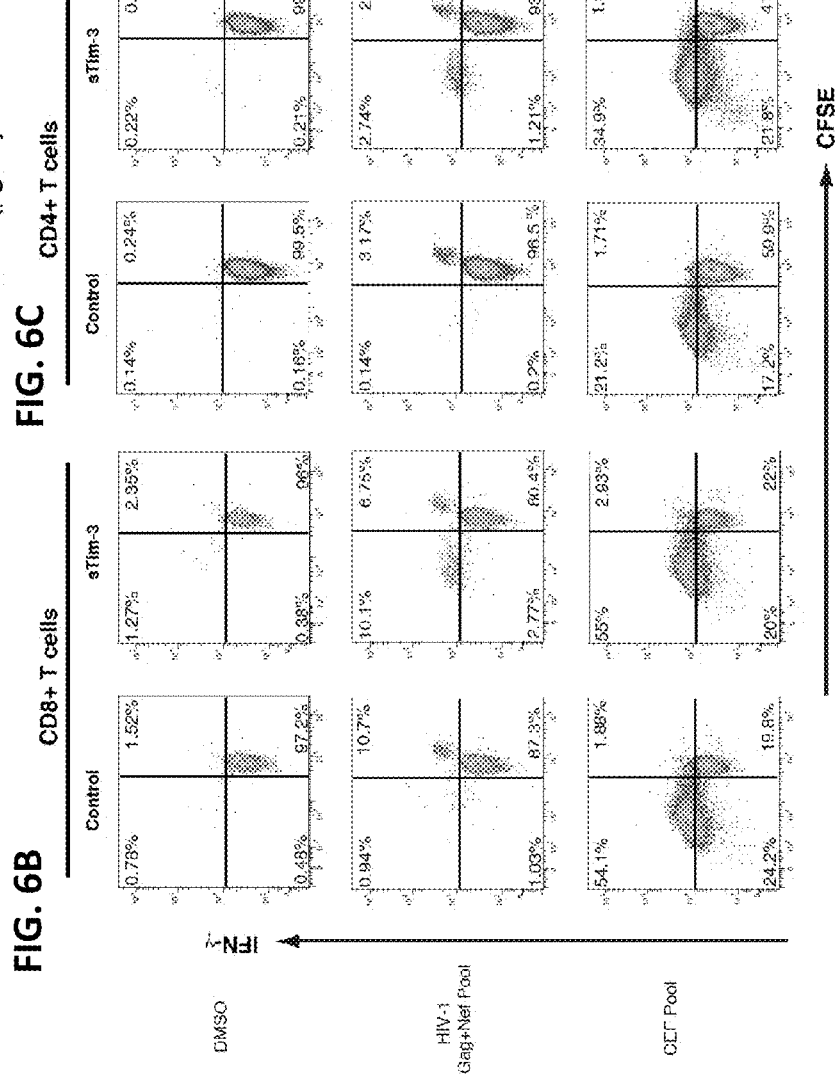

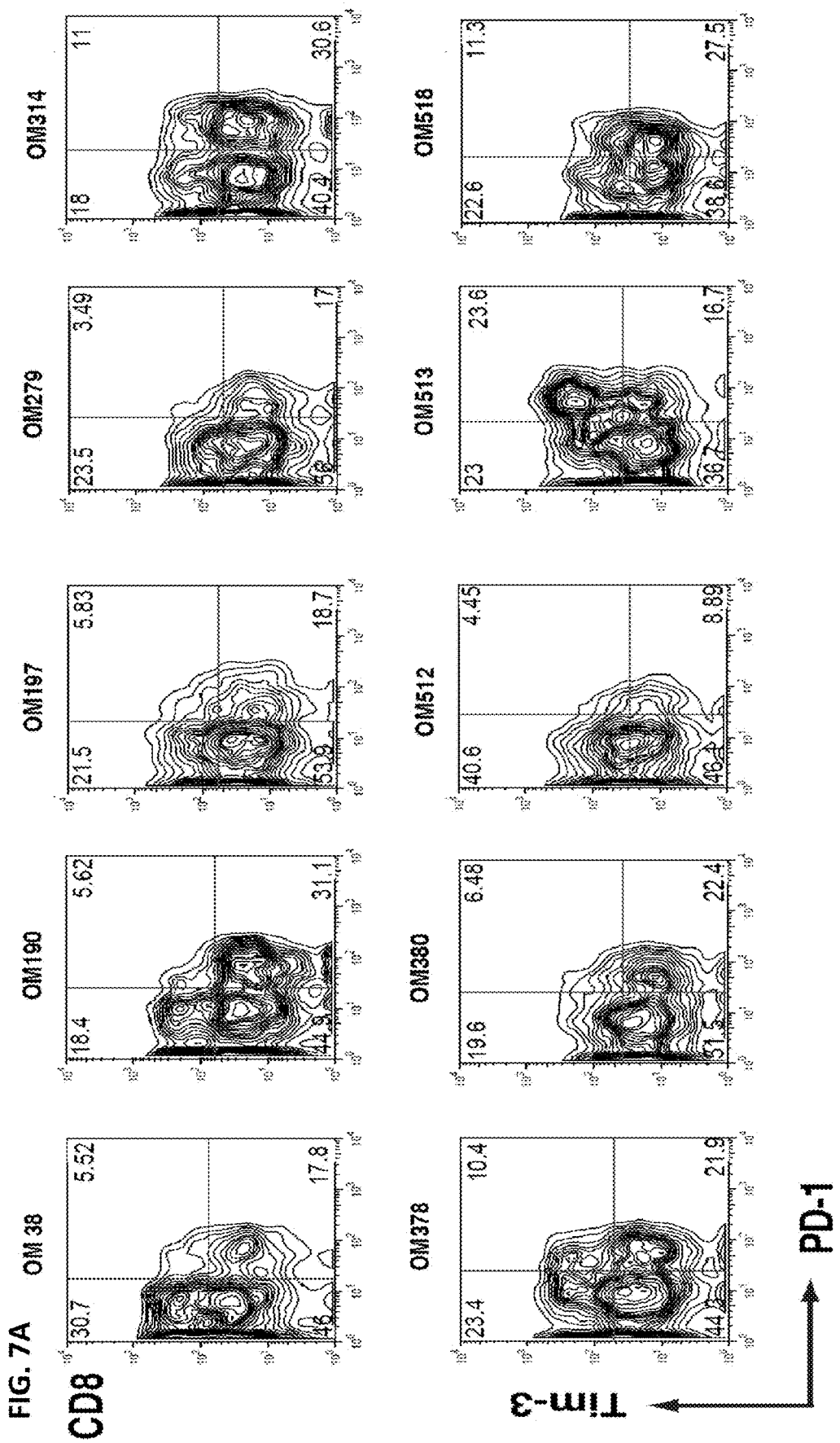

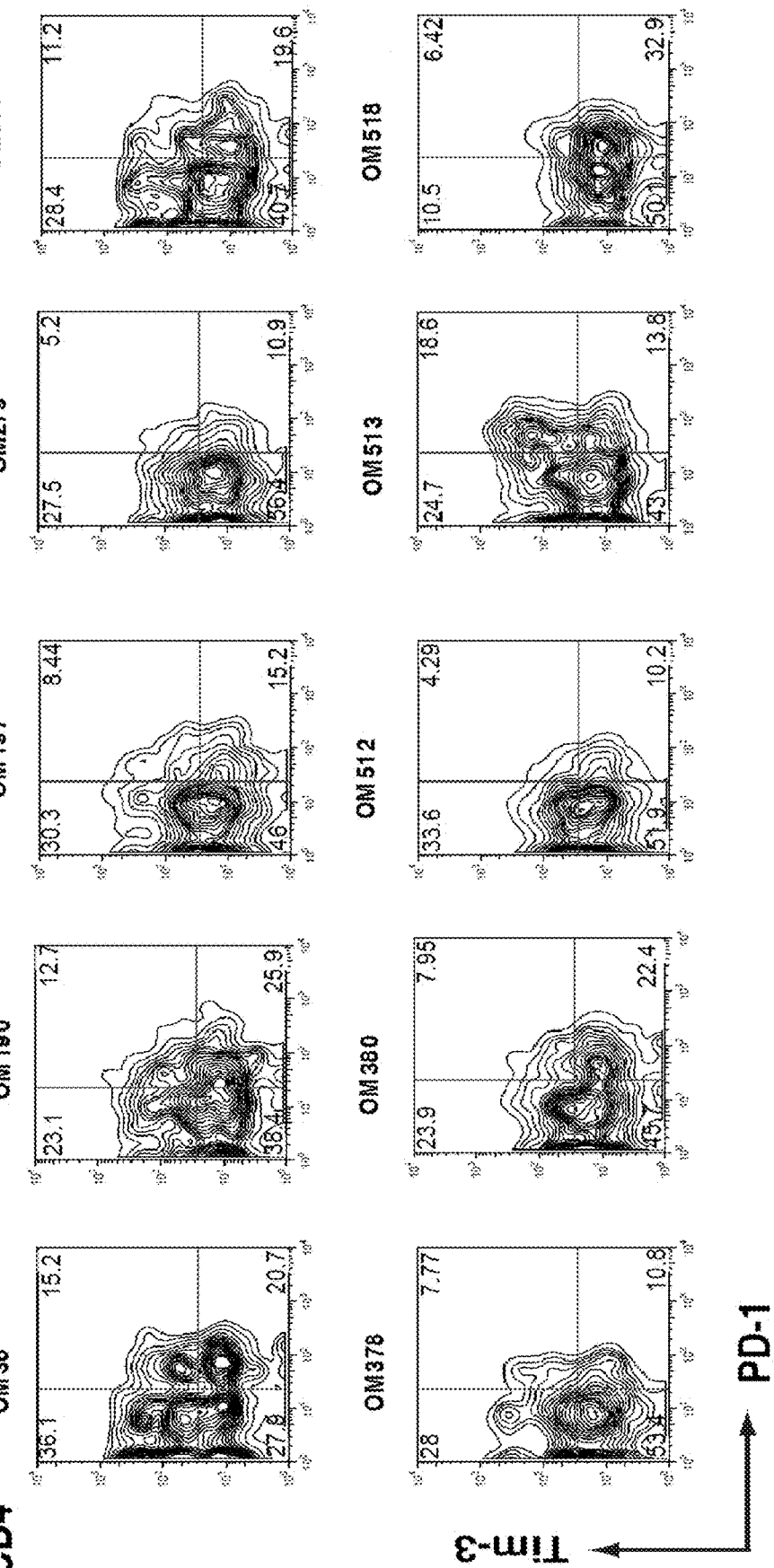

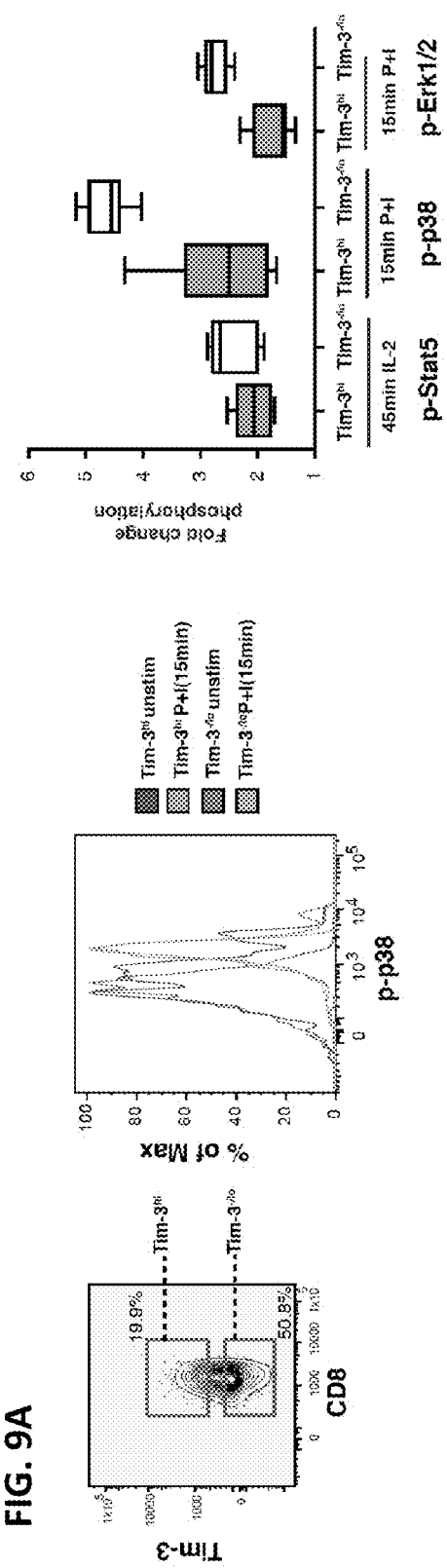
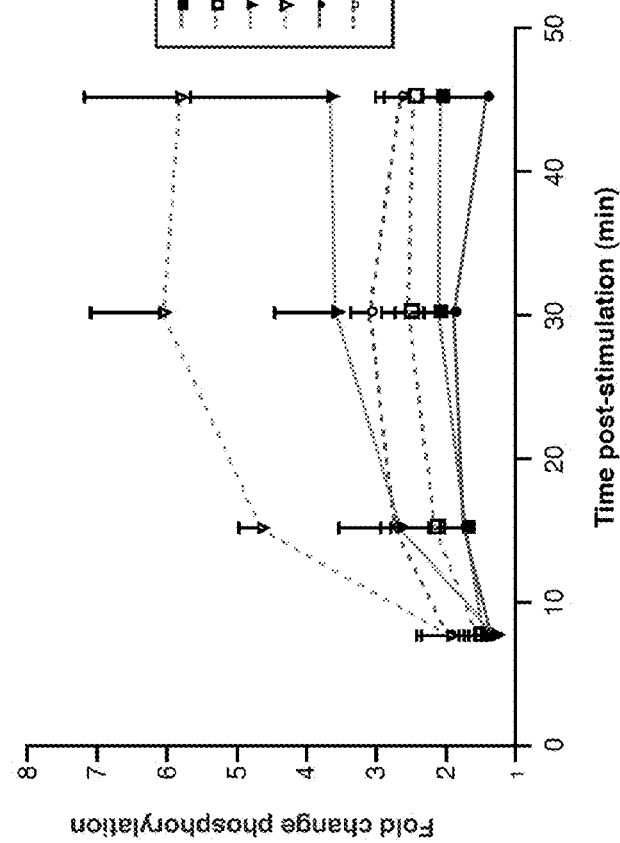
FIG. 9A
FIG. 9B

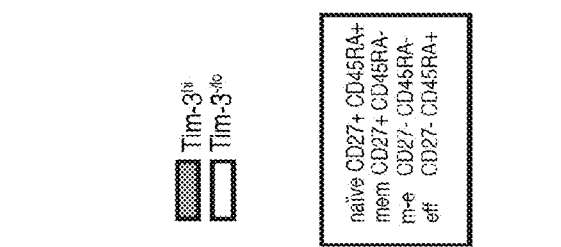
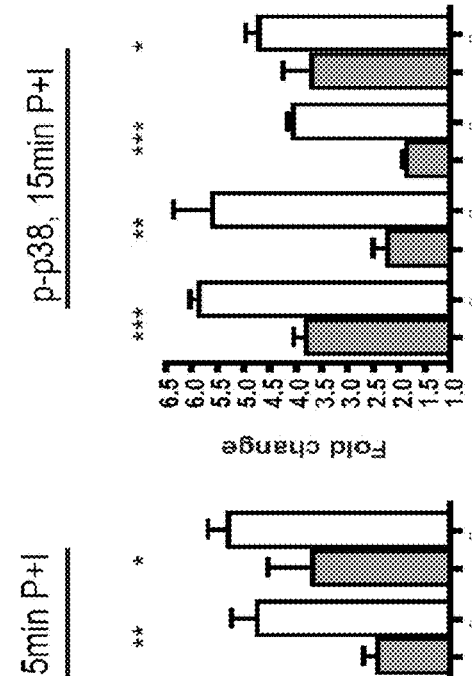
FIG. 9C
FIG. 9D
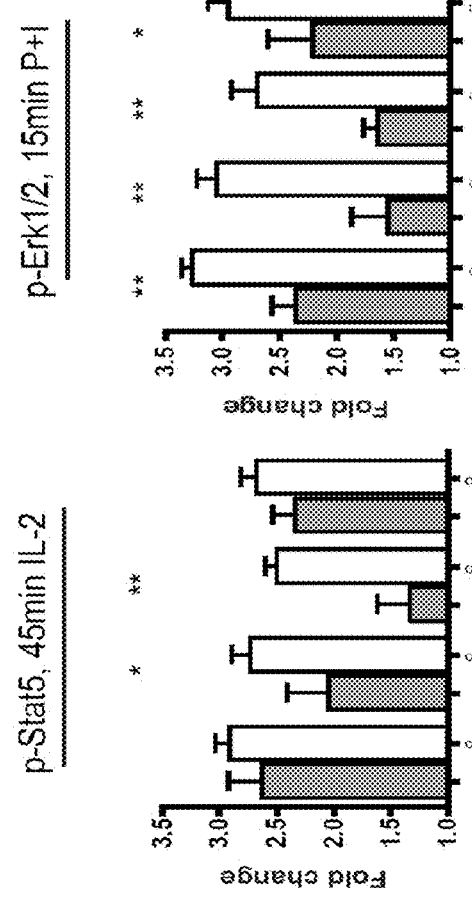
FIG. 9E

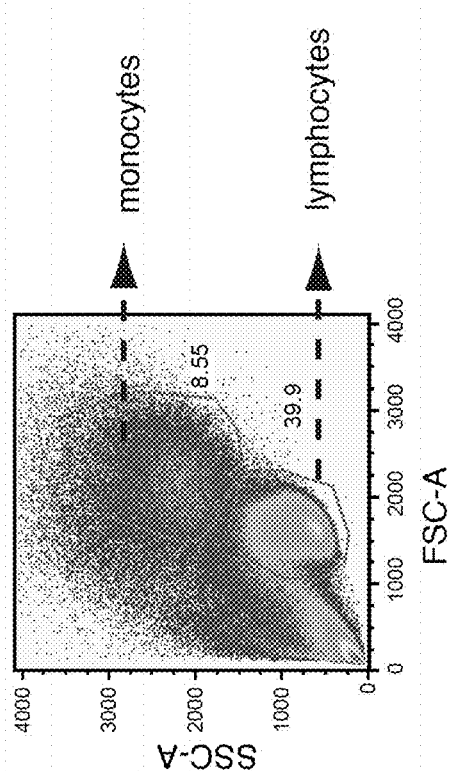
FIG. 10A
FIG. 10B
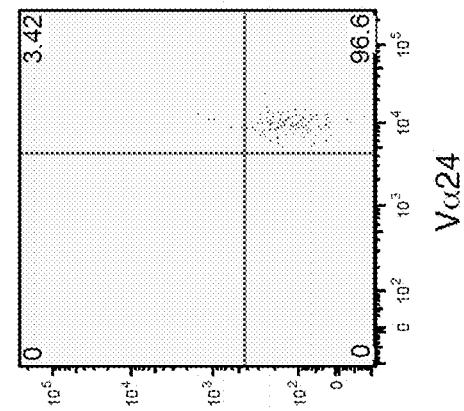
FIG. 10E NKT cells
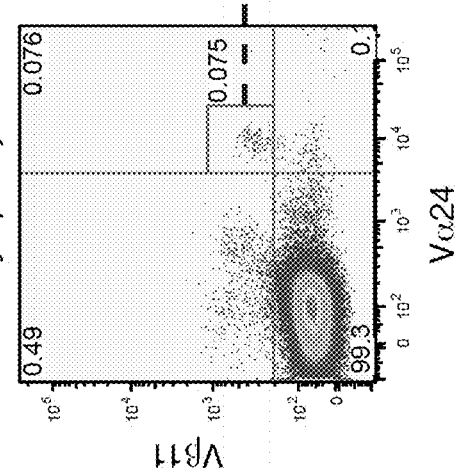
FIG. 10D lymphocytes
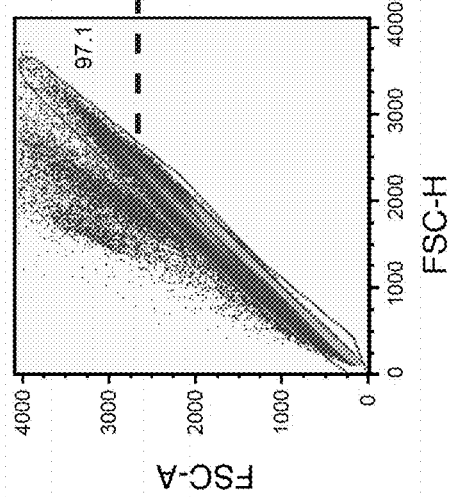
FIG. 10C monocytes

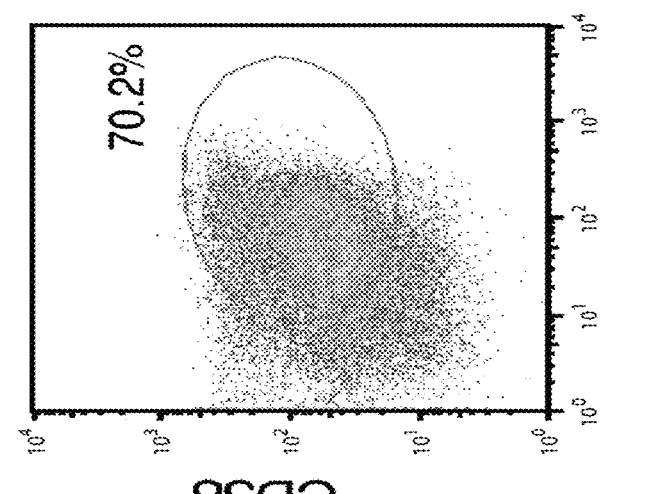
FIG. 11C
FIG. 11B
FIG. 11A
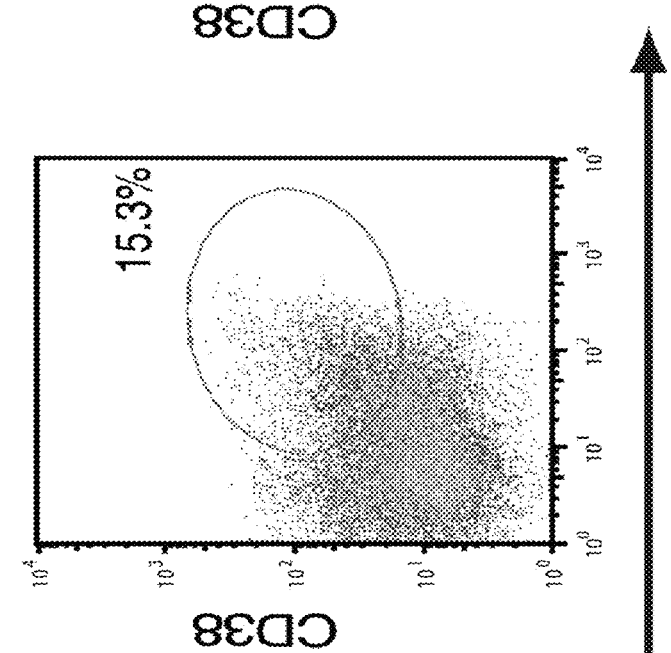
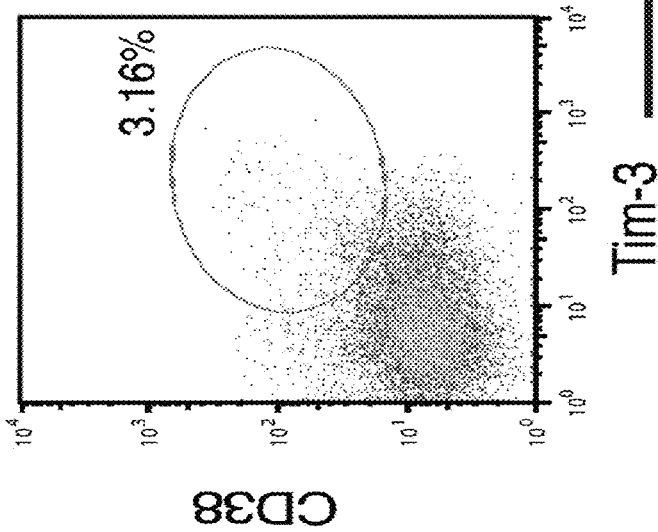

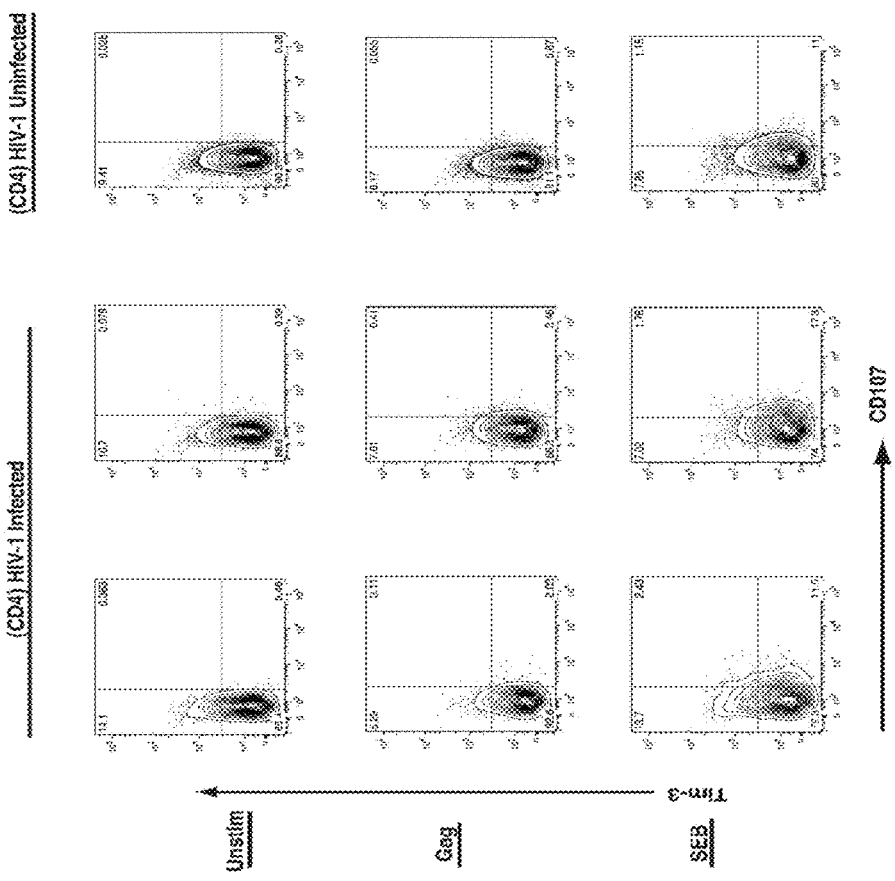
FIG. 14D    FIG. 14C    FIG. 14B    FIG. 14A
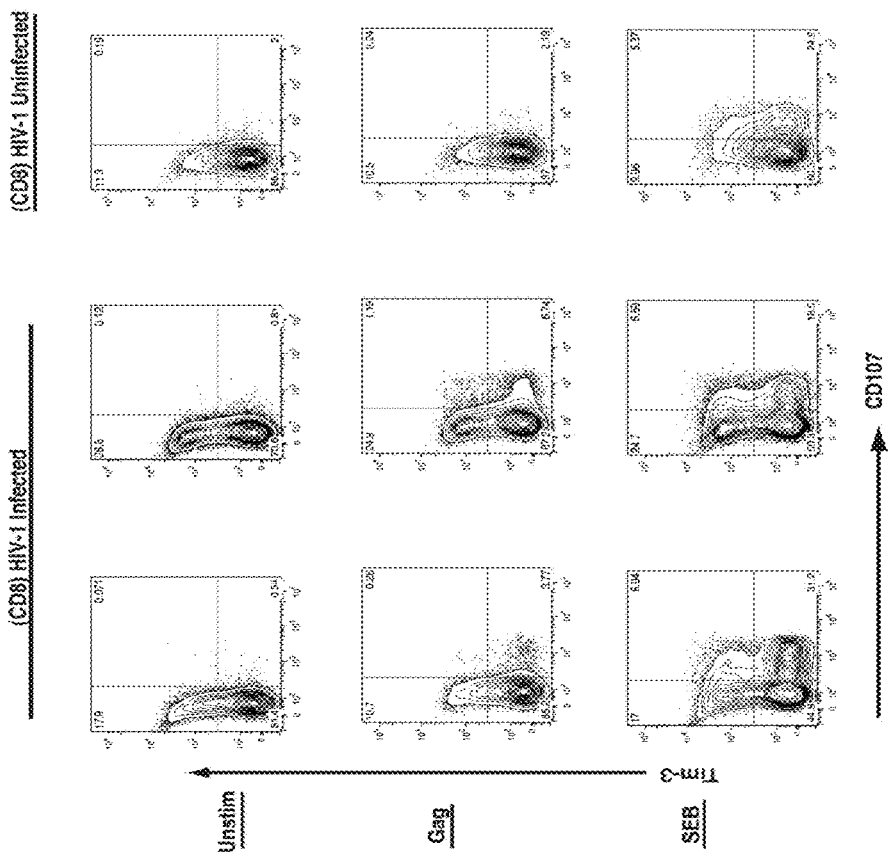

METHODS FOR INHIBITING HIV OR HCV INFECTION BY ADMINISTERING TIM-3 BINDING INHIBITORS

CROSS-REFRENCE TO RELATED APPLICATIONS

The present application is a divisional application of U.S. patent application Ser. No. 12/739,639, filed Apr. 23, 2010, now U.S. Pat. No. 9,416,165, which is a § 371 application of PCT/CA2008/001873, filed Oct. 27, 2008, which claims priority to U.S. Provisional Application No. 60/982,771, filed Oct. 26, 2007. The entire disclosure of each of the foregoing applications is incorporated by reference herein.

REFERENCE TO A SEQUENCE LISTING

This application contains a Sequence Listing submitted electronically as a text file by EFS-Web. The text file, named "Sequence_Listing_ST25", has a size in bytes of 8870 bytes, and was recorded on Apr. 23, 2010. The information contained in the text file is incorporated herein by reference in its entirety pursuant to 37 CFR § 1.52(e)(5).

FIELD OF THE APPLICATION

The present application relates to methods of treating viral infections and methods of increasing immune system activity by modulating Tim-3 activity. In addition, the present application relates to methods of diagnosing or monitoring immune system activity, acute and chronic viral infection and inflammatory disease using Tim-3 expression.

BACKGROUND OF THE APPLICATION

It is clear from many studies that HIV-1-specific $CD8^+$ and $CD4^+$ T cell responses have a prominent role in controlling viral replication (1-4). However, in most cases cellular immunity to HIV-1 proves incapable of long-term control of viremia, and without antiretroviral therapy, progression to AIDS occurs. It has become evident that the ultimate failure of the host immune system to contain HIV-1 is related to the functional impairment of virus-specific $CD8^+$ and $CD4^+$ T cells which accompanies progressive HIV-1 infection, a phenomenon referred to as T cell exhaustion (5-7).

Effective T cell responses are characterized by polyfunctional cytokine production, cytotoxic potential, and strong proliferation in response to antigen (11-14). In the context of chronic infection with HIV-1, the deterioration of the T cell response follows a characteristic pattern. Proliferative capacity, cytotoxic potential, and the ability to produce IL-2 are lost early, while production of IFN-γ is more enduring. Ultimately, the majority of both $CD8^+$ and $CD4^+$ T cells chronically exposed to antigen lose the ability to produce IFN-γ and enter into a state of peripheral anergy (8-13). This has been demonstrated by tetramer studies which have observed that only a small fraction of HIV-1-specific T cells produce cytokine in response to antigen (14-18). Recently, a step forward has been made in understanding T cell exhaustion by the identification of a causative contribution of signaling through PD-1 (5-7). Given the characteristic complexity of T cell regulation, other mechanisms for dampening effector functions of chronically activated cells likely exist.

T cell immunoglobulin and mucin domain-containing molecule 3 (Tim-3) is an immunoglobulin (Ig) superfamily member. The murine homologue of Tim-3 was identified as a specific cell surface marker of $T_{h1}$ $CD4^+$ T cells (19). Interaction of murine Tim-3 with its interferon inducible ligand galectin-9, has been shown to regulate $T_{h1}$ responses by promoting T cell aggregation and the death of IFN-γ producing $T_{h1}$ cells (20). In mice, blockade of the Tim-3 pathway prevents the acquisition of transplantation tolerance induced by costimulatory blockade (21) (22). Furthermore, Tim-3-deficient mice are refractory to the induction of high dose tolerance in an experimental autoimmune encephalomyelitis (EAE) model, and anti-Tim-3 mAbs treatment of SJL/J mice exacerbated EAE (23) (19). Together, these results show that Tim-3 interactions play a role in suppressing $T_{h1}$ mediated immune responses in mice through the termination of effector $T_{h1}$ cells.

SUMMARY OF THE APPLICATION

The inventors have identified a novel population of functionally impaired T cells in subjects infected with acute and chronic viruses, such as HIV. This population of cells expresses the glycoprotein Tim-3 on their surface. In addition, the inventors have identified that the presence of this population of cells correlates with CD38 expression and with the viral load in subjects either acutely or chronically infected with viruses, such as HIV, and that the presence of this population of cells inversely correlates with $CD4^+$ T cell count. Further, the inventors have shown that blocking Tim-3 activity improves immune system function. In particular, the inventors have shown that blocking Tim-3 signaling improves the function of T-cells.

Accordingly, the application includes a method of monitoring immune system activity or function in a subject, comprising the steps:
 (a) determining the expression of Tim-3 on the surface of T cells in a sample from the subject; and
 (b) comparing the expression of Tim-3 on the surface of the T cells from the sample with a control;
 wherein a difference in expression of Tim-3 on the surface of T cells in the sample from the subject as compared to the control is indicative of immune system activity or function.

Another aspect of the application is a method of detecting functionally impaired T cells in a subject, comprising the steps:
 (a) determining the expression of Tim-3 on the surface of T cells in a sample from the subject; and
 (b) comparing the expression of Tim-3 on the surface of the T cells from the sample with a control;
 wherein a difference in expression of Tim-3 on the surface of T cells in the sample from the subject as compared to the control is indicative of the presence of functionally impaired T cells in the subject.

A further aspect of the application is a method of monitoring or assessing viral load in a subject, comprising
 (a) determining the expression of Tim-3 on the surface of T cells in a sample from the subject,
 (b) comparing the expression of Tim-3 on the surface of the T cells from the sample with a control;
 wherein a difference in expression of Tim-3 on the surface of T cells in the sample from the subject as compared to the control is indicative of viral load in the subject.

Another aspect of the application is a method of monitoring or assessing disease progression in a subject with a chronic viral infection, comprising
 (a) determining the expression of Tim-3 on the surface of T cells in a sample from the subject, (b) comparing the expression of Tim-3 on the surface of the T cell from the sample with a control;

wherein an increase in expression of Tim-3 on the surface of T cells in the sample as compared to the control is indicative of disease progression, while a decrease in expression of Tim-3 on the surface of T cells in the sample is indicative of disease remission. in one embodiment the control comprises a sample from a previous time-point from the same individual.

An additional aspect of the application is a method of monitoring or diagnosing viral infection in a subject, comprising the steps:

(a) determining the expression of Tim-3 on the surface of T cells in a sample from the subject; and (b) comparing the expression of Tim-3 on the surface of the T cells from the sample with a control;

wherein a difference in expression of Tim-3 on the surface of T cells in the sample from the subject as compared to the control is indicative of viral infection in a subject. The viral infection can be acute or chronic viral infection.

A further aspect of the application is a method of monitoring the efficacy of highly active antiretroviral therapy (HAART), comprising the steps:

(a) determining the expression of Tim-3 on the surface of T cells in a subject prior to initiating HAART; and (b) comparing Tim-3 expression on the surface of T cells from at least one time point after initiation of HAART;

wherein a decrease in Tim-3 expression is indicative of effective therapy.

A further aspect of the application is a method of treating a subject with a viral infection, comprising administering an effective amount of an inhibitor of Tim-3 to the subject afflicted with a viral infection.

The application also includes the use of an effective amount of an inhibitor of Tim-3 for treating a subject afflicted with a viral infection and the use of an effective amount of an inhibitor of Tim-3 for manufacturing a medicament for treating a subject afflicted with a viral infection. In addition, the application relates to an inhibitor of Tim-3 for use in treating viral infections. In one embodiment, the viral infection is an acute viral infection. In another embodiment, the viral infection is a chronic viral infection.

Another aspect of the invention is a method of reversing immune defects which persist with highly active antiretroviral treatment (HAART) therapy comprising administering an effective amount of an inhibitor of Tim-3 to the subject in need thereof.

The application also includes the use of an inhibitor of Tim-3 for reversing immune defects which persist with HAART therapy and the use of an inhibitor of Tim-3 for manufacturing a medicament for reversing immune defects which persist with HAART therapy. In addition, the application relates to an inhibitor of Tim-3 for use in reversing immune defects which persist with HAART therapy.

A further aspect of the application is a method of improving the function of functionally impaired T cells, comprising treating the functionally impaired T cells with an inhibitor of Tim-3.

The application also includes the use of an inhibitor of Tim-3 for improving the function of functionally impaired T cells and the use of an inhibitor of Tim-3 for manufacturing a medicament for improving the function of functionally impaired T cells. In addition, the application relates to an inhibitor of Tim-3 for use in improving the function of functionally impaired T cells.

In addition, the application includes a method of inducing an immune response in a subject against a chronic virus, such as HIV-1 or HCV, comprising co-administering to said subject an effective amount of a chronic viral antigen, such as an HIV-1 antigen or HCV antigen, and an inhibitor of Tim-3.

The application also includes the use of an effective amount of a chronic viral antigen and an inhibitor of Tim-3 for inducing an immune response in a subject against a chronic virus and the use of an effective amount of an chronic antigen and an inhibitor of Tim-3 for manufacturing a medicament for inducing an immune response in a subject against a chronic virus. In addition, the application relates to a chronic viral antigen and an inhibitor of Tim-3 for use in inducing an immune response in a subject against a chronic virus.

In addition, the application provides a method of inducing an immune response in a subject against human endogenous retrovirus (HERV) or long-interspersed nuclear element (LINE) antigens comprising co-administering to said subject an effective amount of a LINE or HERV immunogen, and an inhibitor of Tim-3. In one embodiment, the method is used to induce an immune response against HIV infected cells which express HERV or LINE antigens. HERV antigens are described in U.S. Ser. No. 11/880,126 incorporated herein by reference.

The application also includes the use of an effective amount of a LINE or HERV immunogen and an inhibitor of Tim-3 for inducing an immune response in a subject and the use of an effective amount of a LINE or HERV immunogen and an inhibitor of Tim-3 for manufacturing a medicament for inducing an immune response in a subject. In addition, the application relates to a LINE or HERV immunogen and an inhibitor of Tim-3 for use in inducing an immune response in a subject.

Further, the application includes a method of treating or preventing a chronic viral infection, such as an HIV-1 infection or HCV infection, in a subject comprising co-administering to said subject an effective amount of a chronic viral antigen, such as an HIV-1 antigen, an HCV antigen, a HERV antigen or a LINE antigen, and an inhibitor of Tim-3.

The application also includes the use of an effective amount of a chronic viral antigen and an inhibitor of Tim-3 for treating or preventing a chronic viral infection in a subject and the use of an effective amount of a chronic viral antigen and an inhibitor of Tim-3 for manufacturing a medicament for treating or preventing a chronic viral infection in a subject. In addition, the application relates to a chronic viral antigen and an inhibitor of Tim-3 for use in treating or preventing a chronic viral infection in a subject.

The application also includes compositions comprising a soluble form of Tim-3 and methods and uses thereof.

Other features and advantages of the present application will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIGS. 1A-1R show that Tim-3 is upregulated on T cells in HIV-1 infection and its expression correlates with parameters of HIV-1 disease progression. (FIGS. 1A-1F) PBMCs from HIV-1 infected individuals and HIV-1 uninfected controls were stained with antibodies against Tim-3, CD4, CD8 and CD3. Shown is data obtained by staining with a biotinylated polyclonal goat anti-Tim-3 antibody, followed by a secondary streptavidin-APC conjugate. Confirmatory experiments were performed using PE conjugated monoclonal anti-Tim-3, and an excellent correlation between the two data sets was observed, with slightly higher frequencies of Tim-3 expressing cells observed with polyclonal anti-Tim-3 (see also FIGS. 12A-12C). Representative plots show events gated on the CD3$^+$ population and subsequently on the CD8$^+$ (FIGS. 1A, 1B, 1C) or CD4$^+$ (FIGS. 1D, 1E, 1F) populations. Staining was performed using biotinylated normal goat control antisera and streptavidin-APC to control for potential non-specific binding of polyclonal goat anti-Tim-3 (FIGS. 1A, 1D). Shown are representative levels of Tim-3 in an HIV-1 uninfected subject (FIGS. 1B, 1E) in comparison to an HIV-1 infected subject (FIGS. 1C, 1F). The percentages of Tim-3$^+$ cells on CD8$^+$ and CD4$^+$ T cells (FIGS. 1G, 1H) are indicated for 31 individuals separated into the following groups: HIV-1 uninfected, HIV-1-infected acute/early, HIV-1-infected chronic, and HIV-1-infected controller. Groups were defined as follows: Acute/early=infected with HIV-1 within the last 4 months; chronic=infected>1 year with CD4 decline; controller=infected>1 year, no evidence of CD4 decline, and viral load<5,000 copies/ml bDNA. Statistical analyses were performed using the Mann-Whitney test. (I-R) Correlation between Tim-3 expression on CD8$^+$ (FIGS. 1I-1K, 1O, 1P) and CD4$^+$ (FIGS. 1L-1N, 1Q, 1R) T cells and viral load (FIGS. 1I, 1L, 1O, 1Q), CD4 T cell counts (FIGS. 1J, 1M) and levels of CD38 expression (FIGS. 1K, 1N, 1P, 1R) are shown. Statistical analyses were performed using the Spearman's rank correlation test.

FIGS. 2A-2H show PBMC from 8 chronically HIV-1 infected individuals were stained with pentamers to A2 restricted CMV, EBV, and HIV-1 epitopes. (FIG. 2A-2D) Shown are representative flow cytometry data from one individual using tetramer to the CMV pp65 epitope 'NLVPMVATV' (O) (SEQ ID NO: 16), the EBV epitope 'GLCTLVAML' (P) (SEQ ID NO: 17), the HIV-1-Pol epitope 'ILKEPVHGV' (Q) (SEQ ID NO: 18), and the HIV-1-Gag epitope 'SLYNTVATL' (SEQ ID NO: 7). The mean fluorescence intensity (MFI) of pentamer$^+$ cells were compared for all detectable responses to each epitope. (FIGS. 2E-2H) Tim-3 expression was heterogenous amongst HIV-1-specific responses with some exhibiting very high levels of Tim-3, while others exhibited only baseline levels (FIGS. 2F, 2H). Statistical analyses were performed using the Wilcoxon matched pairs T test.

FIGS. 4A-4C show PBMC from both HIV-1-infected and uninfected individuals that were sorted for Tim-3$^+$ and Tim-3$^-$ populations within both CD8$^+$ and CD4$^+$ T cell subsets and quantified T-bet ($T_{h1}$), GATA-3 ($T_{h2}$), and IFN-γ ($T_{h1}$) mRNA by qPCR. For both CD8$^+$ and CD4$^+$ T cell populations, GATA-3 was expressed at higher levels in the Tim-3$^-$ fraction than in the Tim-3$^+$ fraction, while T-bet was more highly expressed in the Tim-3$^+$ population.

FIGS. 5A-5R show Tim-3 expressing CD8$^+$ and CD4$^+$ T cells populations hyporesponsive to antigenic stimulation. PBMCs derived from HIV-1 infected and uninfected individuals were stimulated with pooled peptides or SEB superantigen for 12 hours, and then stained for IFN-γ, TNF-α and Tim-3 using monoclonal antibodies, and analyzed by multiparametric flow cytometry. (FIGS. 5A-5D) Representative plots showing cytokine responses in CD8$^+$ and CD4$^+$ T cells from HIV-1 infected and HIV-1 uninfected individuals. (FIGS. 5E-5G) Tetramer analysis was performed on PBMC from a chronically HIV-1 infected individual using A2*SLYNTVATL (SEQ ID NO: 7) (FIG. 5E). PBMC from the same individual were stimulated with SLYNTVATL (SEQ ID NO: 7) peptide, or with DMSO as a control, and cytokine production versus Tim-3 expression was analyzed by flow cytometry (FIGS. 5F, 5G). CD8$^+$ T cells were sorted into purified Tim-3$^{+/hi}$ CD8$^+$ T cells and Tim-3$^{-/lo}$ (FIGS. 5H, 5I, 5J) CD8$^+$ T cells populations and labeled with CFSE. These two populations were then cultured in the presence of anti-CD3 and anti-CD28 monoclonal antibodies for 5 days. Cells where then assessed for the diminution of CFSE as a readout of cell division (FIGS. 5K, 5L). (FIGS. 5M-5R) Co-stained ex vivo PBMC from 5 HIV-1-uninfected individuals, and 5 HIV-1-infected chronic progressors, with Tim-3 and Ki67 antigen. Elevated frequencies of Ki67$^+$ cells were observed in both the CD4$^+$ and CD8$^+$ T cell subsets of HIV-1-infected versus uninfected PBMC (FIGS. 5M-5N). The large majority of Tim-3$^+$ cells were Ki67$^-$, Ki67$^+$ CD8$^+$ and CD4$^+$ T cells were greatly enriched for Tim-3 expressing cells (FIG. 5R).

FIGS. 6A-6E show that blocking the Tim-3 signaling pathway by the addition of soluble Tim-3 enhances proliferation and cytokine production of HIV-1-specific T cells. (FIG. 6A) The addition of sTim-3 enhanced the expansion of CD8$^+$ T cells specific for the HLA-A*0201 restricted HIV-1-Gag epitope 'SLYNTVATL' (SL9) (SEQ ID NO: 7) in HIV-1-infected chronic progressors in a dose-dependent manner up to 2 μg/ml. (FIGS. 6B, 6C) PBMCs from 6 HIV-1 infected patients were stained with CFSE and the effect of sTim-3 on cytokine production and proliferation of PBMCs was determined in four individuals over a 6 day stimulation assay. Shown is representative data from an acutely HIV-1 infected individual on day 6 of culturing showing IFN-γ secretion (y-axis) by CFSE (x-axis) in CD8$^+$ (FIG. 6B) and CD4$^+$ (FIG. 6C), T cell populations in response to DMSO (Upper row), pooled Gag/Nef peptides (middle row) or CEF pooled peptides (lower row) in the presence or absence of either 1 μg/ml sTim-3 or an equal volume of expression control. (FIG. 6D) Enhanced proliferation of both CD8$^+$ and CD4$^+$ T cells was also observed when PBMC from chronic progressors were stimulated with pooled Gag and Nef peptides. (FIG. 6E) Addition of 10 μg/ml of mAb 2E2 resulted in a profound rescue of HIV-1-Gag T cell proliferative responses.

FIGS. 7A-7F show PBMC from 10 individuals with chronic progressive HIV-1 infection co-stained for Tim-3 and PD-1. Expression was analyzed by flow cytometry after gating on CD8⁺ or CD4⁺ T cells. (FIGS. 7A-7B) Demonstrates that in 9/10 subjects, Tim-3 and PD-1 were primarily expressed by distinct populations of CD8⁺ T cells. One subject, OM513, displayed a frequent Tim-3⁺ PD-1⁺ population (23.6%), but retained both Tim-3⁺ PD-1⁻ and Tim-3⁻ PD-1⁺ populations (23.0% and 16.7% respectively). (FIGS. 7C-7D) Demonstrates that 9/10 subjects showed primarily divergent staining for PD-1 and Tim-3 on CD4⁺ T cells. (FIGS. 7E-7F) In HIV-1-specific CD8⁺ T cells, two patterns of expression were observed: tetramer⁺ populations were predominantly Tim-3⁺ PD-1⁻ (FIG. 7E), or they were predominantly Tim-3⁻ and PD-1⁺ (FIG. 7F). Both patterns showed that a minority population co-expressed both Tim-3 and PD-1 demonstrating that Tim-3 and PD-1 expression define primarily distinct populations.

FIG. 9A demonstrates phospho-flow cytometry analyses of phosphorylation status of Stat5, p38, and ERK-1/2 in Tim-3⁺ versus Tim-3⁻ CD8⁺ T cells from HIV-1 infected subject. CD8⁺ T cells were sorted based on their Tim-3 expression status and stimulated with either rIL-2 or PMA/Ionomycin in triplicates wells from each sample. Shown is representative FACS gating for sorting Tim-3⁺/hi and Tim-3⁻/lo PBMCs. Shown is a summary of data from 4 chronically HIV-1 infected individuals. (FIG. 9B) A representative time course from one individual. (FIGS. 9C-9E) Shown is the compiled data for (FIG. 9C) Stat5, (FIG. 9D) ERK-1/2, and (FIG. 9E) p38 showing differential levels of change in target phosphorylation (measured by change in mean fluorescence intensity) in Tim-3⁺ versus Tim-3⁻ cells within each of the following CD8⁺ T cell sub-populations: naïve (CD27⁺CD45RA⁺), memory (CD27⁺ CD45RA⁻), effector memory (CD27⁻, CD45RA⁻), or effector (CD27⁻, CD45RA⁺).

FIGS. 10A-10E show the expression of Tim-3 in NKT cells and monocyte subpopulations in PBMCs from a healthy subject. Representative plots of n=8.

FIGS. 11A-11C show the flow cytometry plots of CD38 versus Tim-3 expression on CD8⁺ T cells from three subjects: (FIG. 11A) an HIV-1 infected controller, (FIG. 11B) an HIV-1 infected chronic progressor with a moderate viral load, and (FIG. 11C) an HIV-1 infected chronic progressor with advanced disease and a high viral load.

FIGS. 14A-14D show TNF-α and CD107a expression in response to antigen were similarly restricted to Tim-3⁻ cells.

DETAILED DESCRIPTION OF THE APPLICATION

Figure 1I:
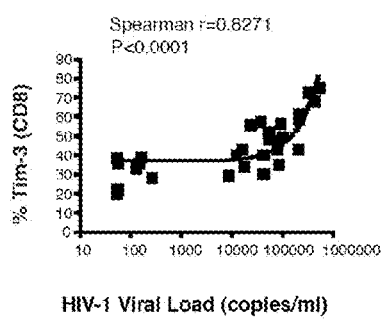
Figure 1J:
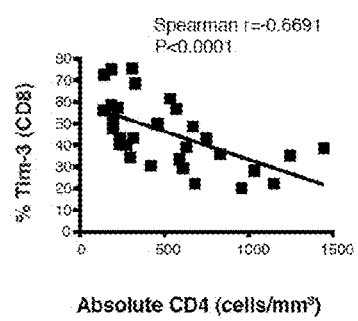
Figure 1K:
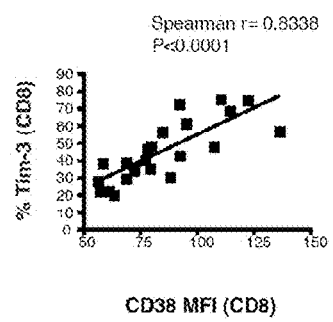
Figure 1L:
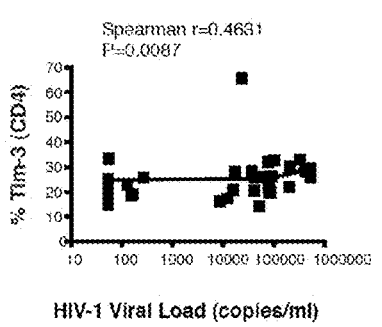
Figure 1M:
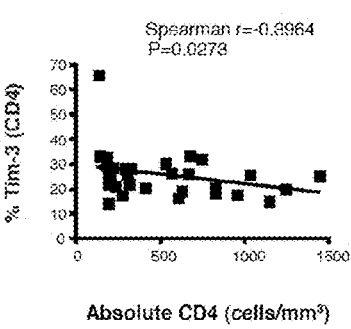
Figure 1N:
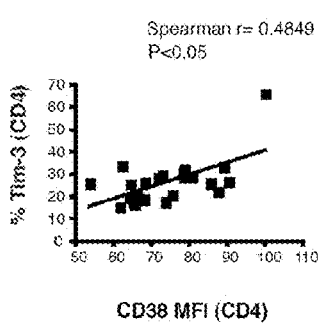
Figure 1O:
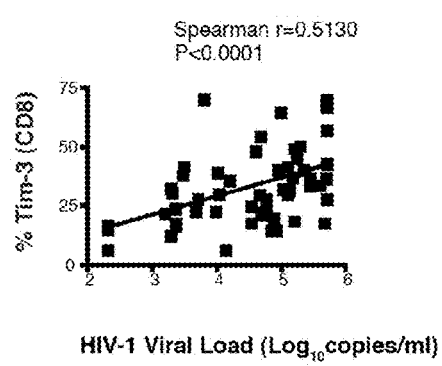
Figure 1P:
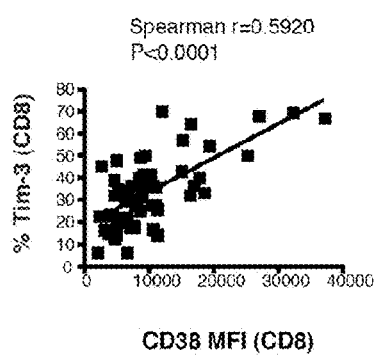
Figure 1Q:
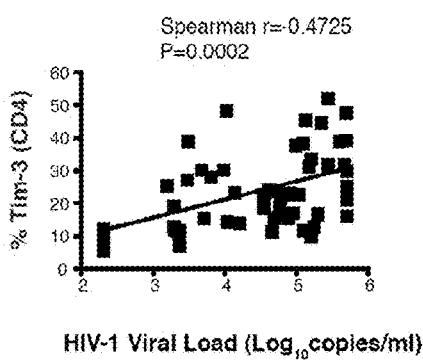
Figure 1R:
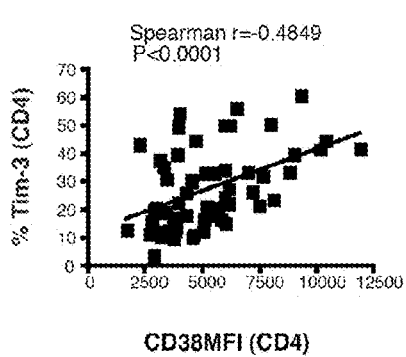

As mentioned above, the inventors have identified a novel functionally impaired T cell population that expresses Tim-3. This population of T cells is found in subjects afflicted with acute and chronic viral infections, such as HIV infection. The inventors have identified that the presence of this population in subjects infected with chronic viruses proportionally correlates with viral load and CD38 expression, and inversely correlates with CD4⁺ T cell count. In addition, the inventors have shown that blocking Tim-3 activity improves immune system function.

Accordingly, the application includes a method of monitoring immune system activity or function in a subject, comprising the steps:
(a) determining the expression of Tim-3 on the surface of T cells in a sample from the subject; and
(b) comparing the expression of Tim-3 on the surface of the T cells from the sample with a control;
wherein a difference in expression of Tim-3 on the surface of T cells in the sample from the subject as compared to the control is indicative of immune system activity or function.

The term "Tim-3" as used herein refers to T cell immunoglobulin and mucin domain-containing molecule 3. In one embodiment, Tim-3 is of human origin. In another embodiment, Tim-3 has the sequence:

```
                                        (SEQ ID NO: 5)
MFSHLPFDCV LLLLLLLLTR SSEVEYRAEV GQNAYLPCFY

TPAAPGNLVP VCWGKGACPV FECGNVVLRT DERDVNYWTS

RYWLNGDFRK GDVSLTIENV TLADSGIYCC RIQIPGIMND

EKFNLKLVIK PAKVTPAPTR QRDFTAAFPR MLTTRGHGPA

ETQTLGSLPD INLTQISTLA NELRDSRLAN DLRDSGATIR

IGIYIGAGIC AGLALALIFG ALIFKWYSHS KEKIQNLSLI
```

-continued

SLANLPPSGL ANAVAEGIRS EENIYTIEEN VYEVEEPNEY

YCYVSSRQQP SQPLGCRFAMP or a variant thereof.

The term "variant" as used herein includes modifications, substitutions, additions, derivatives, analogs, fragments or chemical equivalents of the Tim-3 amino acid sequences disclosed herein that perform substantially the same function as the Tim-3 peptides and peptide inhibitors disclosed herein in substantially the same way. For instance, the variants of the Tim-3 peptides would have the same function of being useful in monitoring immune system activity or function, in detecting functionally impaired cells, in monitoring viral load and monitoring or diagnosing chronic viral infection. Variants of Tim-3 peptide inhibitors would have the same function as being useful to inhibit Tim-3.

Variants also include peptides with amino acid sequences that are substantially or essentially identical to the amino acid sequences of SEQ ID NO:5, 2 or 6.

The term "substantially identical" or "essentially identical" as used herein means an amino acid sequence that, when optimally aligned, for example using the methods described herein, share at least 75%, 80%, 85%, 90%, 95%, 96%, 97%, 98%, 99%, or 100% sequence identity with a second amino acid sequence.

The term "sequence identity" as used herein refers to the percentage of sequence identity between two polypeptide and/or nucleotide sequences.

To determine the percent identity of two amino acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues at corresponding amino acid positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecule of the present application. BLAST protein searches can be performed with the XBLAST program parameters set, e.g., to score-50, wordlength=3 to obtain amino acid sequences homologous to a protein molecule of the present disclosure. To obtain gapped alignments for comparison purposes, Gapped BLAST can be utilized as described in Altschul et al., 1997, *Nucleic Acids Res.* 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another preferred, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

The percentage of identity between two polypeptide sequences, the amino acid sequences of such two sequences are aligned, for example using the Clustal W algorithm (Thompson, J D, Higgins D G, Gibson T J, 1994, *Nucleic Acids Res.* 22(22): 4673-4680.), together with BLOSUM 62 scoring matrix (Henikoff S. and Henikoff J. G., 1992, *Proc. Natl. Acad. Sci. USA* 89: 10915-10919.) and a gap opening penalty of 10 and gap extension penalty of 0.1, so that the highest order match is obtained between two sequences wherein at least 50% of the total length of one of the sequences is involved in the alignment.

Other methods that may be used to align sequences are the alignment method of Needleman and Wunsch (Needleman and Wunsch. *J. Mol. Biol.,* 1970, 48:443), as revised by Smith and Waterman (Smith and Waterman. *Adv. Appl. Math.* 1981, 2:482) so that the highest order match is obtained between the two sequences and the number of identical amino acids is determined between the two sequences. Other methods to calculate the percentage identity between two amino acid sequences are generally art recognized and include, for example, those described by Carillo and Lipton (Carillo and Lipton *SIAM J. Applied Math.* 1988, 48:1073) and those described in Computational Molecular Biology (Computational Molecular Biology, Lesk, e.d. Oxford University Press, New York, 1988, *Biocomputing: Informatics and Genomics Projects*). Generally, computer programs will be employed for such calculations.

Variants of the Tim-3 peptides and peptide inhibitors disclosed herein also include, without limitation, conservative amino acid substitutions. A "conservative amino acid substitution" as used herein, is one in which one amino acid residue is replaced with another amino acid residue without abolishing the desired function or activity of the peptide inhibitors disclosed herein. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. Conserved amino acid substitutions involve replacing one or more amino acids of the polypeptides of the disclosure with amino acids of similar charge, size, and/or hydrophobicity characteristics. When only conserved substitutions are made the resulting variant should be functionally equivalent. Changes which result in production of a chemically equivalent or chemically similar amino acid sequence are included within the scope of the disclosure. If the peptide inhibitors of the present application are made using recombinant DNA technology, variants of the peptide inhibitors may be made by using polypeptide engineering techniques such as site directed mutagenesis, which are well known in the art for substitution of amino acids. For example, a hydrophobic residue, such as glycine can be substituted for another hydrophobic residue such as alanine. An alanine residue may be substituted with a more hydrophobic residue such as leucine, valine or isoleucine. A negatively charged amino acid such as aspartic acid may be substituted for glutamic acid. A positively charged amino acid such as lysine may be substituted for another positively charged amino acid such as arginine. The phrase "conservative substitution" also includes the use of a chemically derivatized residue in place of a non-derivatized residue provided that such polypeptide displays the requisite activity.

Variants of the Tim-3 peptides and peptide inhibitors of the present application also include additions and deletions to the amino acid sequences disclosed herein.

Variants of the Tim-3 peptides and peptide inhibitors of the present application also include analogs thereof. The term "analog" as used herein includes any active agent capable of performing the function of the Tim-3 peptides and peptide inhibitors disclosed herein, and may include peptide mimetics and the like. The term "active" refers to molecules in a conformation suitable for performing substantially the same functions as the peptide inhibitors disclosed herein in substantially the same way. Peptide mimetics include synthetic structures that may serve as substitutes for peptides in interactions between molecules (see Morgan and Gainor. (1989), Ann. Reports Med. Chem. 24:243-252 for a review). Peptide mimetics include synthetic structures which may or may not contain amino acids and/or peptide bonds but are designed to retain the desired structural and functional features and thus may be suitable substitutes of the peptide inhibitor analog disclosed in the present application.

Peptide mimetics also include molecules incorporating peptides into larger molecules with other functional elements (e.g., as described in WO 99/25044). Peptide mimetics also include peptoids, oligopeptoids (Simon et al (1972) Proc. Natl. Acad, Sci USA 89:9367), and peptide libraries containing peptides of a designed length representing all possible sequences of amino acids corresponding to an isolated peptide of the disclosure. Peptide mimetics may be designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amino acids to stabilize or promote reverse turn conformations and to help stabilize the molecule. Cyclic amino acid analogues may be used to constrain amino acid residues to particular conformational states. The mimetics can also include mimics of inhibitor peptide secondary structures. These structures can model the 3-dimensional orientation of amino acid residues into the known secondary conformations of proteins. Peptoids may also be used which are oligomers of N-substituted amino acids and can be used as motifs for the generation of chemically diverse libraries of novel molecules.

Variant Tim-3 peptides and peptide inhibitors of the present application also include derivatives thereof. The term "derivative" refers to a peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. A derivative of a polypeptide also optionally includes polypeptides comprising forms of amino acids that are oxidized.

Variant Tim-3 peptides and peptide inhibitors of the present application also include fragments thereof. The term "fragment" as used herein means a portion of a polypeptide that contains, preferably, at least 10%, 20%, 30%, 40%, 50%, 60%, 70%, 80%, 90%, 95%, or more of the entire length of the reference polypeptide.

The phrase "determining expression of Tim-3 on the surface of T cells" as used herein means assessing the expression of Tim-3, including qualitative and quantitative expression, on the surface of T cells. This includes assessing the frequency or level of Tim-3 expression on individual cells or populations of cells. This also includes assessing the frequency or number of Tim-3 expressing cells. A person skilled in the art will appreciate that a number of methods can be used to detect, determine and/or quantify cell surface expression of Tim-3 including immunoassays such as Western blots, immunoprecipitation followed by SDS-PAGE, immunocytochemistry, FACS, protein arrays, and the like.

For example, antibodies specific for Tim-3 can be used to determine the expression of Tim-3 on the surface of T cells.

The term "antibody" as used herein is intended to include monoclonal antibodies, polyclonal antibodies, and chimeric antibodies. The antibody may be from recombinant sources and/or produced in transgenic animals. The term "antibody fragment" as used herein is intended to include without limitations Fab, Fab', F(ab')2, scFv, dsFv, ds-scFv, dimers, minibodies, diabodies, and multimers thereof, multispecific antibody fragments and domain antibodies. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be synthesized by recombinant techniques.

Antibodies to Tim-3 are commercially available (R&D Systems). However, a person skilled in the art will appreciate that one could produce other antibodies that are specific for Tim-3.

To produce monoclonal antibodies, antibody producing cells (lymphocytes) can be harvested from an immunized animal with the antigen of interest (e.g. Tim-3) and fused with myeloma cells by standard somatic cell fusion procedures thus immortalizing these cells and yielding hybridoma cells. Such techniques are well known in the art, (e.g. the hybridoma technique originally developed by Kohler and Milstein (Nature 256:495-497 (1975)) as well as other techniques such as the human B-cell hybridoma technique (Kozbor et al., Immunol. Today 4:72 (1983)), the EBV-hybridoma technique to produce human monoclonal antibodies (Cole et al., Methods Enzymol, 121:140-67 (1986)), and screening of combinatorial antibody libraries (Huse et al., Science 246:1275 (1989)). Hybridoma cells can be screened immunochemically for production of antibodies specifically reactive with the antigen of interest and the monoclonal antibodies can be isolated.

The phrase "method of monitoring immune system activity or function" as used herein refers to a method or process of determining or assessing the activity or function of the immune system, including the degree of immune system activity or function. The term also includes determining or assessing the frequency, function and/or activity of immune cells, including T cells.

The term "immune system function" as used herein refers to the function of the immune system including humoral or cell-mediated. Immune system function can be assessed using assays known to those skilled in the art including, but not limited to, antibody assays (for example ELISA assays), proliferation assays, antigen specific cytotoxicity assays and the production of cytokines (for example ELISPOT assays), such as IFN-γ, TNF-α, IL-2 and/or IL-17. In one embodiment, immune system function refers to the number of, proliferation of and/or cytokine production by $CD4^+$ and/or $CD8^+$ T cells.

The term "immune system activity" as used herein refers to the activation status of the immune system. For example, activation status can be assessed using surface markers on T cells, such as CD38.

A person skilled in the art will appreciate that immune system activity and immune system function are different. For example, the functionally impaired T cells identified by the inventors that express Tim-3 have impaired function (e.g. impaired ability to proliferate and produce cytokines). However, the inventors have also shown that Tim-3 expression correlates with CD38 expression, which is a predictor of T cell activation. Thus, without being limited to theory, Tim-3 acts to suppress the effector functions of activated T cells.

The term "subject" as used herein refers to any member of the animal kingdom, preferably a mammal, more preferably a human being. In one embodiment, the subject has a chronic viral infection such as HIV infection or other chronic viral infection, such as HCV. In another embodiment, the subject has an acute viral infection, such as acute HIV infection, acute HCV infection, influenza infection, SARS infection, hepatitis B infection, hepatitis C infection, rhinovirus infection, cytomegalovirus infection, Epstein-barr virus infection, measles, varicella-zoster virus infection, herpes simplex infection, human papillomavirus infection, enterovirus infection, rubella infection, dengue virus, HTLV-I infection, HTLV-II infection, west nile virus, infection, and others. In a further embodiment, the subject has a chronic rheumatologic condition, such as rheumatoid arthritis, systemic lupus erythematosis, ankylosing spondylitis, or other rheumatologic condition. In an additional embodiment, the subject has an immunosuppressed condition or is immunosuppressed, such as after a transplantation.

The term "sample" as used herein refers to any fluid, cell or tissue sample from a subject which contains T cells. For example, the sample could be from the circulatory system or lymphatic system, such as blood, serum or lymphatic fluid.

The term "T cells" includes $CD4^+$ T cells and/or $CD8^+$ T cells. For example, Tim-3 expression can be determined on either or both $CD4^+$ or $CD8^+$ T cells.

The term "control" as used herein refers to a sample from a subject or a group of subjects who are either known as having a particular condition or trait or as not having a particular condition or trait. The control can vary depending on what is being monitored, assessed or diagnosed. For example, if one is monitoring immune system activity or function, the control can be from a subject who is known to have a suppressed immune system or an activated immune system. In another embodiment, the control is from a subject or a group of subjects known to express a particular level or amount of Tim-3 on the surface of their T cells. The control can also be a predetermined standard or reference range of values.

The term "difference in expression of Tim-3 on the surface of T cells in the sample from the subject as compared to the control" means that Tim-3 is differentially expressed on the surface of T cells in the sample from the subject as compared to the control.

The term "differentially expressed" or "differential expression" as used herein refers to a difference in the level of expression of Tim-3. The term "difference in the level of expression" refers to an increase or decrease in the measurable expression level of Tim-3 as compared with the measurable expression level of Tim-3 in a second sample or control. The term can also refer to an increase or decrease in the measurable expression level of Tim-3 in a population of samples as compared with the measurable expression level of Tim-3 in a second population of samples. In one embodiment, the differential expression can be compared using the ratio of the level of expression of Tim-3 as compared with the expression level of the Tim-3 of a control, wherein the ratio is not equal to 1.0. For example, a protein is differentially expressed if the ratio of the level of expression in a first sample as compared with a second sample is greater than or less than 1.0. For example, a ratio of greater than 1, 1.2, 1.5, 1.7, 2, 3, 5, 10, 15, 20 or more, or a ratio less than 1, 0.8, 0.6, 0.4, 0.2, 0.1, 0.05, 0.001 or less. In another embodiment the differential expression is measured using p-value. For instance, when using p-value, Tim-3 is identified as being differentially expressed as between a first and second population when the p-value is less than 0.1, preferably less than 0.05, more preferably less than 0.01, even more preferably less than 0.005, the most preferably less than 0.001.

The phrase "indicative of immune system activity or function" as used herein refers to comparing the expression of Tim-3 on the surface of T cells from the sample with a control and determining whether there is a difference of expression and whether the results indicate that the immune system of the subject has decreased or increased activity or function as compared to the control. As mentioned above, Tim-3 expression is indicative of functionally impaired T cells, and thus indicative of impaired immune system function. Accordingly in one embodiment, if the control is from a normal subject, known to be healthy and not have a viral infection or inflammatory disease, then increased Tim-3 expression on T cells from the subject as compared to the control indicates that the subject has decreased immune system function relative to a normal control. In another example, if the control is from a normal subject, known to be healthy and not have a viral infection or inflammatory disease, then decreased Tim-3 expression on T cells from the subject as compared to the control indicates that the subject has increased immune system function relative to a normal control. In a further embodiment, if the control is a reference standard known to be indicative of a healthy individual not having a viral infection or inflammatory disease, then increased Tim-3 expression is on T cells from the subject as compared to the control indicates that the subject has decreased immune system function relative to the control. If the control is a reference standard known to be indicative of viral infection or inflammatory disease, then decreased Tim-3 expression from the subject compared to the control indicates that the subject has increased immune system function relative to the control.

Higher than normal immune system activity can be an indicator of an inflammatory disease. Thus, the method can be used to monitor or diagnose an inflammatory disease. This includes determining whether or not a subject has an inflammatory disease or the extent or severity of the inflammatory disease as compared to a control. This method can be used in combination with other traditional diagnostic techniques for inflammatory disease.

In one embodiment, the inflammatory disease is an autoimmune disease. In one embodiment, the autoimmune disease is multiple sclerosis, transplant rejection, GVHD, acute disseminated encephalomyelitis, coeliac disease, Crohn's disease, diabetes mellitus type 1, Graves' disease, Kawasaki's Disease, myasthenia gravis or a chronic rheumatologic condition. In a specific embodiment, the rheumatologic condition is rheumatoid arthritis, systemic lupus erythematosis, or ankylosing spondylitis.

The method can also be used to monitor inflammatory activity in immunosuppressed conditions, such as transplantation to monitor organ rejection.

Another aspect of the application is a method of detecting functionally impaired T cells in a subject, comprising the steps:
  (a) determining the expression of Tim-3 on the surface of T cells in a sample from the subject; and
  (b) comparing the expression of Tim-3 on the surface of the T cells from the sample with a control;
    wherein a difference in expression of Tim-3 on the surface of T cells in the sample from the subject as compared to the control is indicative of the presence of functionally impaired T cells in the subject.

The term "functionally impaired T cells" as used herein refers to hyporesponsive T cells, which are T cells that no longer mount a response to an antigen. In one embodiment, the T cells are antigen-specific $CD8^+$ and/or $CD4^+$ T cells, but no longer produce cytokines (such as IFN-$\gamma$, TNF-$\alpha$, IL-2 and/or IL-17), no longer are cytotoxic and/or no longer proliferate in response to antigen. In a specific embodiment, the antigen is a viral antigen, such as an HIV antigen.

The phrase "indicative of the presence of functionally impaired T cells in the subject" as used herein refers to comparing the expression of Tim-3 on the surface of T cells from the sample with a control and determining whether there is a difference of expression and whether the results indicate that the subject has more or fewer functionally impaired T cells as compared to the control.

The inventors identified that functionally impaired T cells express Tim-3. Thus, if the control is from a normal subject, known to be healthy and not have a viral infection or inflammatory disease, then increased Tim-3 expression on T cells from the subject as compared to the control indicates that the subject has more functionally impaired T cells than a normal control. In another example, if the control is from a normal subject, known to be healthy and not have a viral infection or inflammatory disease, then decreased Tim-3 expression on T cells from the subject as compared to the control indicates that the subject has fewer functionally impaired T cells than a normal control. In a further embodiment, if the control is a reference standard known to be indicative of a healthy individual not having a viral infection or inflammatory disease, then increased Tim-3 expression on T cells from the subject as compared to the control indicates that the subject indicates that the subject has more functionally impaired T cells than the normal control. If the control is a reference standard known to be indicative of viral infection or inflammatory disease, then decreased Tim-3 expression from the subject compared to the control indicates that the subject has fewer functionally impaired T cells than the normal control.

Another aspect of the application is a method of detecting or isolating functionally impaired T cells by detecting Tim-3 expression. For example, T cells expressing Tim-3 can be detected or isolated from a sample or population of cells for further study.

A further aspect of the application is a method of monitoring or assessing viral load in a subject, comprising
  (a) determining the expression of Tim-3 on the surface of T cells in a sample from the subject,
  (b) comparing the expression of Tim-3 on the surface of the T cells from the sample with a control;
    wherein a difference in expression of Tim-3 on the surface of T cells in the sample from the subject as compared to the control is indicative of viral load in the subject.

The term "viral load" refers to the amount of virus in a subject infected with a virus. For example, it refers to the amount of virus in the circulating blood. The method can be used to monitor or assess the viral load of a number of different types of viral infections, including chronic viral infections, such as HIV infection or hepatitis C viral infection (HCV). In a specific embodiment, the chronic viral infection is an HIV infection.

The term "HIV" as used herein refers to the human immunodeficiency virus, and includes HIV-1 and HIV-2.

The phrase "indicative of viral load in the subject" as used herein refers to comparing the expression of Tim-3 on the surface of T cells from the sample with a control and determining whether there is a difference of expression and whether the results indicate that the subject has a higher or lower viral load as compared to the control.

The inventors identified that viral load in a subject correlates with the expression of Tim-3 on T cells in the subject. Thus, if the control is from a normal subject, known to be healthy and not have a chronic viral infection, then increased Tim-3 expression on T cells from the subject as compared to the control indicates that the subject has a higher viral load than a normal control. In another example, if the control is from a normal subject, known to be healthy and not have a chronic viral infection, then decreased Tim-3 expression on T cells from the subject as compared to the control indicates that the subject has lower viral load than a normal control.

An additional aspect of the application is a method of monitoring or diagnosing viral infection in a subject, comprising the steps:
  (a) determining the expression of Tim-3 on the surface of T cells in a sample from the subject; and
  (b) comparing the expression of Tim-3 on the surface of the T cells from the sample with a control;
    wherein a difference in expression of Tim-3 on the surface of T cells in the sample from the subject as compared to the control is indicative of viral infection in a subject. In one embodiment, the viral infection is a chronic viral infection. In another embodiment, the viral infection is an acute viral infection.

The term "chronic viral infection" as used herein refers to a subject afflicted or infected with a chronic virus. In one embodiment, the chronic viral infection is an HIV infection or a hepatitis C viral infection (HCV). In a specific embodiment, the chronic viral infection is an HIV infection.

The term "acute viral infection" as used herein refers to a subject afflicted or infected with an acute virus. Acute viral infections include, without limitation, acute HIV infection, acute HCV infection, influenza infection, SARS infection, hepatitis B infection, hepatitis C infection, rhinovirus infection, cytomegalovirus infection, Epstein-barr virus infection, measles, varicella-zoster virus infection, herpes simplex infection, human papillomavirus infection, enterovirus infection, rubella infection, dengue virus, HTLV-I infection, HTLV-II infection, west nile virus, infection, and others.

The phrase "indicative of viral infection in a subject" as used herein refers to comparing the expression of Tim-3 on the surface of T cells from the sample with a control and determining whether there is a difference of expression and whether the results indicate that the subject has a viral infection or does not have a viral infection or the extent or severity of the viral infection as compared to the control.

The inventors identified that viral infection in a subject correlates with the expression of Tim-3 on T cells in the subject. Thus, if the control is from a normal subject, known to be healthy and not have a viral infection, then increased Tim-3 expression on T cells from the subject as compared to the control indicates that the subject has a viral infection, more of a viral infection or more severe of a viral infection than a normal control. In another example, if the control is from a normal subject, known to be healthy and not have a viral infection, then decreased Tim-3 expression on T cells from the subject as compared to the control indicates that the subject has less of a viral infection or less severe of a viral infection than a normal control. In a further embodiment, if the control is a reference standard known to be indicative of a healthy individual not having a viral infection, then increased Tim-3 expression on T cells from the subject as compared to the control indicates that the subject has a viral infection, more of a viral infection or more severe of a viral infection than the normal control. If the control is a reference standard known to be indicative of viral infection, then decreased Tim-3 expression from the subject compared to the control indicates that the subject has less of a viral infection or less severe of a viral infection than the normal control.

Another aspect of the application is a method of monitoring or assessing disease progression in a subject with a chronic viral infection, comprising
  (a) determining the expression of Tim-3 on the surface of T cells in a sample from the subject,
  (b) comparing the expression of Tim-3 on the surface of the T cell from the sample with a control;
    wherein an increase in expression of Tim-3 on the surface of T cells in the sample as compared to the control is indicative of disease progression, while a decrease in expression of Tim-3 on the surface of T cells in the sample is indicative of disease remission. in one embodiment the control comprises a sample from a previous time-point from the same individual.

A further aspect of the application is a method of monitoring the efficacy of highly active antiretroviral therapy (HAART), comprising the steps:
  (c) determining the expression of Tim-3 on the surface of T cells in an individual prior to initiating HAART; and
  (d) comparing Tim-3 expression on the surface of T cells at least one time point after initiation of HAART;
  wherein a decrease in Tim-3 expression is indicative of effective therapy.

A further aspect of the application is a method of treating a subject with a viral infection, comprising administering an effective amount of an inhibitor of Tim-3 to the subject afflicted with a viral infection. In one embodiment, the subject is afflicted with a chronic viral infection. In another embodiment, the subject is afflicted with an acute viral infection.

The term "afflicted with a chronic viral infection" as used herein refers to a subject with a long-term viral infection. In one embodiment, the viral infection is an HIV infection or a hepatitis C viral infection (HCV). In a specific embodiment, the chronic viral infection is an HIV infection.

The term "afflicted with an acute viral infection" as used herein refers to a subject with a short-term viral infection. In one embodiment, the viral infection is acute HIV infection, acute HCV infection, influenza infection, SARS infection, hepatitis B infection, hepatitis C infection, rhinovirus infection, cytomegalovirus infection, Epstein-barr virus infection, measles, varicella-zoster virus infection, herpes simplex infection, human papillomavirus infection, enterovirus infection, rubella infection, dengue virus, HTLV-I infection, HTLV-II infection, west nile virus infection.

A person skilled in the art can readily determine whether an infection is chronic or acute.

The phrase "method of treating a subject with a viral infection" as used herein includes inhibiting the infection, preventing the infection or reducing the symptoms associated with the infection.

The term a "therapeutically effective amount", "effective amount" or a "sufficient amount" of a compound or composition of the present application is a quantity sufficient to, when administered to the subject, including a mammal, for example a human, effect beneficial or desired results, including clinical results, and, as such, an "effective amount" or synonym thereto depends upon the context in which it is being applied. For example, in the context of treating a chronic viral infection, for example, it is an amount of the compound or composition sufficient to achieve such a treatment as compared to the response obtained without administration of the compound or composition. In the context of disease, therapeutically effective amounts of the compounds or compositions disclosed in the present application are used to treat, modulate, attenuate, reverse, or affect chronic viral infections in a mammal. An "effective amount" is intended to mean that amount of a compound or composition that is sufficient to treat, prevent or inhibit chronic viral infections. In some suitable embodiments, the amount of a given compound or composition will vary depending upon various factors, such as the given drug or compound, the pharmaceutical formulation, the route of administration, the type of disease or disorder, the identity of the subject or host being treated, and the like, but can nevertheless be routinely determined by one skilled in the art. Also, as used herein, a "therapeutically effective amount" of a compound or composition of the present application is an amount which prevents, inhibits, suppresses or reduces chronic viral infections in a subject as compared to a control. As defined herein, a therapeutically effective amount of a compound or composition of the present application may be readily determined by one of ordinary skill by routine methods known in the art.

The term "inhibitor of Tim-3" or "Tim-3 inhibitor" as used herein refers to a compound, substance or composition that can inhibit the function of Tim-3. For example, the inhibitor can inhibit the expression or activity of Tim-3, modulate or block the Tim-3 signaling pathway and/or block the binding of Tim-3 to a ligand. Such inhibitors include peptides, antibodies, nucleic acid molecules and small molecules. In one embodiment, the inhibitor binds a Tim-3 ligand. In another embodiment, the inhibitor is an antibody specific for Tim-3 and/or its ligand. Antibodies to Tim-3 can be prepared as described previously.

In an embodiment, the inhibitor is a soluble form of Tim-3. A soluble form of Tim-3 includes, without limitation, a molecule lacking the transmembrane and intracellular domains, for example, a molecule comprising the IgV and/or mucin domains of Tim-3. In one embodiment, the soluble form of Tim-3 comprises the amino acid sequence of SEQ ID NO:2 or a variant thereof. In another embodiment, the soluble form of Tim-3 consists of the amino acid sequence of SEQ ID NO:2. In another embodiment, the soluble form of Tim-3 comprises the amino acid sequence of SEQ ID NO:6 or a variant thereof. In another embodiment, the soluble form of Tim-3 consists of the amino acid sequence of SEQ ID NO:6.

The application also includes an isolated amino acid sequence comprising the amino acid sequence of SEQ ID NO: 2 or 6 or a variant thereof. The term variant has been defined previously.

In another embodiment, the Tim-3 inhibitor is a nucleic acid molecule. The nucleic acid molecule may be a small interfering RNA (SiRNA) or antisense molecule that targets and inhibits the expression of the Tim-3 nucleic acid sequence.

The term "antisense nucleic acid" as used herein means a nucleotide sequence that is complementary to its target e.g. a Tim-3 transcription product. The nucleic acid can comprise DNA, RNA or a chemical analog, that binds to the messenger RNA produced by the target gene. Binding of the antisense nucleic acid prevents translation and thereby inhibits or reduces target protein expression. Antisense nucleic acid molecules may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

The term "siRNA" refers to a short inhibitory RNA that can be used to silence gene expression of a specific gene. The siRNA can be a short RNA hairpin (e.g. shRNA) that activates a cellular degradation pathway directed at mRNAs corresponding to the siRNA. Methods of designing specific siRNA molecules and administering them are known to a person skilled in the art. It is known in the art that efficient silencing is obtained with siRNA duplex complexes paired to have a two nucleotide 3' overhang. Adding two thymidine nucleotides is thought to add nuclease resistance. A person skilled in the art will recognize that other nucleotides can also be added.

Aptamers are short strands of nucleic acids that can adopt highly specific 3-dimensional conformations. Aptamers can exhibit high binding affinity and specificity to a target molecule. These properties allow such molecules to specifically inhibit the functional activity of proteins. Thus, in another embodiment, the Tim-3 inhibitor is an aptamer that binds and inhibits Tim-3 activity.

The application also includes compositions comprising an inhibitor of Tim-3, such as a soluble form of Tim-3. In one embodiment, the inhibitor of Tim-3, such as a soluble form of Tim-3, is formulated into pharmaceutical compositions for administration to subjects in a biologically compatible form suitable for administration in vivo. By "biologically compatible form suitable for administration in vivo" is meant a form of the substance to be administered in which any toxic effects are outweighed by the therapeutic effects. Another embodiment is a pharmaceutical composition for treating a subject with a chronic viral infection comprising an inhibitor of Tim-3, such as a soluble form of Tim-3, and a pharmaceutically acceptable carrier, diluent or excipient.

The compositions described herein can be prepared by per se known methods for the preparation of pharmaceutically acceptable compositions that can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, 20th ed., Mack Publishing Company, Easton, Pa., USA, 2000). On this basis, the compositions include, albeit not exclusively, solutions of the substances in association with one or more pharmaceutically acceptable vehicles or diluents, and contained in buffered solutions with a suitable pH and iso-osmotic with the physiological fluids.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions. The pharmaceutical composition may be supplied, for example but not by way of limitation, as a lyophilized powder which is reconstituted with sterile water or saline prior to administration to the patient.

Pharmaceutical compositions of the application may comprise a pharmaceutically acceptable carrier. Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1(2,3-dioleyloxy) propyl)N, N, N-trimethylammonium chloride (DOTMA), diolesylphosphotidyl-ethanolamine (DOPE), and liposomes. Such compositions should contain a therapeutically effective amount of the compound, together with a suitable amount of carrier so as to provide the form for direct administration to the patient.

The composition may be in the form of a pharmaceutically acceptable salt which includes, without limitation, those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc In accordance with the methods disclosed herein, the inhibitors of Tim-3, may be administered to a patient in a variety of forms depending on the selected route of administration, as will be understood by those skilled in the art. The inhibitors of Tim-3 may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

The inhibitors of Tim-3 may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the compound of the invention may be incorporated with excipient and used in the form of ingestible tablets, buccal tablets, troches, capsules, elixirs, suspensions, syrups, wafers, and the like.

The inhibitors of Tim-3 may also be administered parenterally. Solutions of the inhibitors of Tim-3 can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (2000-20th edition) and in The United States Pharmacopeia: The National Formulary (USP 24 NF19) published in 1999.

The pharmaceutical forms suitable for injectable use include sterile aqueous solutions or dispersion and sterile powders for the extemporaneous preparation of sterile injectable solutions or dispersions. In all cases, the form must be sterile and must be fluid to the extent that easy syringability exists.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

The inhibitors of Tim-3 can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The inhibitors of Tim-3 may also be delivered by the use of monoclonal antibodies as individual carriers to which the inhibitors of Tim-3 are coupled. The compounds of the application may also be coupled with soluble polymers as targetable drug carriers. Such polymers can include polyvinylpyrrolidone, pyran copolymer, polyhydroxypropylmethacrylam ide-phenol, polyhydroxy-ethylaspartamide-phenol, or polyethyleneoxide-polylysine substituted with palmitoyl residues. Furthermore, compounds of the application may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The compounds of the application may be used alone or in combination with other known agents useful for treating or preventing chronic viral infections.

When used in combination with other agents useful in treating chronic viral infections, the inhibitors of Tim-3 are suitably administered contemporaneously with those agents. As used herein, "contemporaneous administration" of two substances to an individual means providing each of the two substances so that they are both biologically active in the individual at the same time. The exact details of the administration will depend on the pharmacokinetics of the two substances in the presence of each other, and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances.

The compounds of the application may be administered to an animal alone or also in combination with pharmaceutically acceptable carriers, as noted above, the proportion of which is determined by the solubility and chemical nature of the compound, chosen route of administration and standard pharmaceutical practice.

The dosage of inhibitors of Tim-3 can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the animal to be treated. One of skill in the art can determine the appropriate dosage based on the above factors. Compounds of the application may be administered initially in a suitable dosage that may be adjusted as required, depending on the clinical response. As a representative example, oral dosages of a compound of the invention will range between about 1 mg per day to about 400 mg per day for an adult, suitably about 1 mg per day to about 200 mg per day, more suitably about 1 mg per day to about 20 mg per day. When formulated for oral administration, the compounds are suitably in the form of tablets containing 0.25, 0.5, 0.75, 1.0, 5.0, 10.0, 20.0, 25.0, 30.0, 40.0, 50.0, 60.0, 70.0 75.0, 80.0, 90.0, 100.0 150, 200, 250, 300, 350 or 400 mg of active ingredient per tablet. Suitably, for oral administration, the compounds are suitably in the form of tablets containing 0.25, 0.5, 0.75, 1.0, 5.0 or 10.0, mg of active ingredient per tablet. The compounds of the invention may be administered in a single daily dose or the total daily dose may be divided into two, three of four daily doses. If the compounds of the application are to be administered transdermally, using, for example, those forms of transdermal skin patches that are well known to those skilled in the art, the dosage administration will be continuous rather than intermittent throughout the dosage range.

The application also includes the use of an effective amount of an inhibitor of Tim-3 for treating a subject afflicted with a chronic viral infection and the use of an effective amount of an inhibitor of Tim-3 for manufacturing a medicament for treating a subject afflicted with a chronic viral infection. In addition, the application relates to an inhibitor of Tim-3 for use in treating chronic viral infections.

A further aspect of the application is a method of improving the function of functionally impaired T cells, comprising treating the functionally impaired T cells with an inhibitor of Tim-3.

The term "improving the function of functionally impaired T cells" as used herein means improving or restoring the function of the functionally impaired T cells in comparison to functionally impaired T cells that have not been contacted with an inhibitor of Tim-3. For instance, the functionally impaired T cells with improved function will have improved or restored ability to mount a response to an antigen. In one embodiment, the functionally impaired T cells have improved or restored ability to produce cytokines, cytotoxic activity and/or proliferation in response to an antigen. In a specific embodiment, the antigen is a viral antigen, such as an HIV or HCV antigen.

The application also includes the use of an inhibitor of Tim-3 for improving the function of functionally impaired T cells and the use of an inhibitor of Tim-3 for manufacturing a medicament for improving the function of functionally impaired T cells. In addition, the application relates to an inhibitor of Tim-3 for use in improving the function of functionally impaired T cells.

In one embodiment, the method is performed ex vivo. For example, functionally impaired T cells, which express Tim-3, are obtained from a subject. These functionally impaired T cells are contacted or treated with an inhibitor of Tim 3, such as soluble Tim-3 or an antibody specific for Tim-3 and/or its ligand, for a period of time in vitro so that the function of the functionally impaired T cells is restored or improved, and then these T cells are re-infused back into the subject.

Another aspect of the invention is a method of reversing immune defects which persist with highly active antiretroviral treatment (HAART) therapy comprising administering an effective amount of an inhibitor of Tim-3 to the subject in need thereof.

The application also includes the use of an inhibitor of Tim-3 for reversing immune defects which persist with HAART therapy and the use of an inhibitor of Tim-3 for manufacturing a medicament for reversing immune defects which persist with HAART therapy. In addition, the application relates to an inhibitor of Tim-3 for use in reversing immune defects which persist with HAART therapy.

As described above, the inhibitor of Tim-3 is able to improve the function of functionally impaired T cells, such as hyporesponsive T cells, which are T cells that no longer mount a response to antigen. Thus, inhibitors of Tim-3 can be used in vaccine preparations to induce an immune response in a subject against a chronic virus, such as HIV-1 or HCV. This includes DNA vaccine approaches.

Accordingly, the application includes a method of inducing an immune response in a subject against a chronic virus, such as HIV-1 or HCV, comprising co-administering to said subject an effective amount of a chronic viral antigen, such as an HIV-1 antigen or HCV antigen, and an inhibitor of Tim-3.

The term "inducing an immune response" or "eliciting an immune response" as used herein means initiating, triggering, causing, enhancing, improving or augmenting any response of the immune system, for example, of either a humoral or cell-mediated nature. The initiation or enhancement of an immune response can be assessed using assays known to those skilled in the art including, but not limited to, antibody assays (for example ELISA assays), antigen specific cytotoxicity assays and the production of cytokines (for example ELISPOT assays).

The term "co-administering" as used herein means that the inhibitor of Tim-3 and chronic viral antigen is administered contemporaneously. As mentioned above, the term "contemporaneous administration" of two substances to an individual means providing each of the two substances so that they are both biologically active in the individual at the same time. The exact details of the administration will depend on the pharmacokinetics of the two substances in the presence of each other. In one embodiment, the inhibitor of Tim-3 is administered prior to the chronic viral antigen, for example, to pre-prime or improve the activity of the functionally impaired T cells. In another embodiment, the inhibitor of Tim-3 is administered at the same time as the chronic viral antigen.

In one embodiment, the chronic viral antigen is an HIV-1 antigen.

The term "HIV-1 antigen" as used herein refers to a portion of HIV that is capable of stimulating or inducing the immune system of a subject against HIV-1. The term includes, without limitation, HIV peptide-based vaccines (including gag and nef), recombinant subunit protein-based vaccines (including gp120, gp140 and gp160), live vector-based vaccines, and DNA vaccination containing coding sequences for any HIV-1 gene product (including Gag, Pol, Env, Nef, Tat, Vpu, Vpr, Vif, and Rev). The term also encompasses antigens not directly encoded by HIV-1, but expressed as a result of HIV-1 infection, which can be targeted as effective surrogate markers of HIV-1 infected cells. This includes some peptides and polypeptides encoded by human endogenous retroviruses (Garrison and Jones et al, T cell responses to human endogenous retroviruses in HIV-1 infection. PLoS Pathog. 2007 Nov.; 3(11):e165. PMID: 17997601), and human long interspersed nuclear element sequences.

In another embodiment, the viral antigen is an HCV antigen. The term "HCV antigen" as used herein refers to a portion of HCV that is capable of stimulating or inducing the immune system of a subject against HCV. The term includes, without limitation, HCV peptide-based vaccines (including C, E1, E2, NS1 NS2, NS3, NS4, NS5), recombinant subunit protein-based vaccines (including C, E1, E2, NS1 NS2, NS3, NS4, NS5), live vector-based vaccines, and DNA vaccination containing coding sequences for any HCV gene product (including Gag, C, E1, E2, NS1 NS2, NS3, NS4, NS5).

In another embodiment, the chronic viral antigen is an HIV-2 antigen. The term "HIV-2 antigen" as used herein refers to a portion of HIV-2 that is capable of stimulating or inducing the immune system of a subject against HIV-2. The term includes, without limitation, HIV-2 peptide-based vaccines (including gag and nef), recombinant subunit protein-based vaccines (including gp120, gp140 and gp160), live vector-based vaccines, and DNA vaccination containing coding sequences for any HIV-1 gene product (including Gag, Pol, Env, Nef, Tat, Vpr, Vif, and Rev). The term also encompasses antigens not directly encoded by HIV-2, but expressed as a result of HIV-2 infection, which can be targeted as effective surrogate markers of HIV-2 infected cells. This includes some peptides and polypeptides encoded by human endogenous retroviruses, and human long interspersed nuclear element sequences.

In another embodiment, the chronic viral antigen is an HTLV-I antigen. The term "HTLV-I antigen" as used herein refers to a portion of HTLV-I that is capable of stimulating or inducing the immune system of a subject against HTLV-I. The term includes, without limitation, HTLV-I peptide-based vaccines, recombinant subunit protein-based vaccines, live vector-based vaccines, and DNA vaccination containing coding sequences for any HTLV-I gene product. The term also encompasses antigens not directly encoded by HTLV-I, but expressed as a result of HTLV-I infection, which can be targeted as effective surrogate markers of HTLV-I infected cells.

In another embodiment, the antigen is derived from human endogenous retroviruses (HERVs). The term "HERV antigen" as used herein refers to a portion of HERV that is capable of stimulating or inducing the immune system of a subject against cells expressing HERVs. The term includes, without limitation, HERV peptide-based vaccines, recombinant subunit protein-based vaccines, live vector-based vaccines, and DNA vaccination containing coding sequences for any HERV gene product (including, but not limited to, HERV-K/HML-2, HERV-L, HERV-H, HERV-R, HERV-FRD, HERV-E families). This also includes antigens from HERV-derived open reading frames (ORFs), which do not correspond to full-length gene products (due to deletions, stop codons, frame-shift mutations).

In another embodiment, the antigen is derived from long-interspersed nuclear elements (LINEs). The term "LINE antigen" as used herein refers to a portion of LINE-1 or LINE-2 that is capable of stimulating or inducing the immune system of a subject against cells expressing LINE-1 or LINE-2. The term includes, without limitation, LINE peptide-based vaccines, recombinant subunit protein-based vaccines (ORF1p or ORF2p), live vector-based vaccines (ORF1 or ORF2), and DNA vaccination containing coding sequences for any LINE gene product including ORF1p and ORF2p. This also includes antigens from LINE-derived open reading frames (ORFs), which do not correspond to full-length gene products (due to deletions, stop codons, frame-shift mutations)

Immunogenicity can be significantly improved if the immunizing agent (i.e. the chronic viral antigen co-administered with an inhibitor of Tim-3) and/or composition is, regardless of administration format, co-immunized with an adjuvant. Adjuvants enhance the immunogenicity of an immunogen but are not necessarily immunogenic in and of themselves. Adjuvants may act by retaining the immunogen locally near the site of administration to produce a depot effect facilitating a slow, sustained release of immunogen to cells of the immune system. Adjuvants can also attract cells of the immune system to an immunogen depot and stimulate such cells to elicit immune response. As such, embodiments of this present application encompass pharmaceutical compositions further comprising adjuvants.

Adjuvants have been used for many years to improve the host immune responses to, for example, vaccines. Intrinsic adjuvants (such as lipopolysaccharides) normally are the components of killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established.

A wide range of extrinsic adjuvants can provoke potent immune responses to immunogens. These include saponins complexed to membrane protein antigens (immune stimulating complexes), pluronic polymers with mineral oil, killed mycobacteria and mineral oil, Freund's complete adjuvant, bacterial products such as muramyl dipeptide (MDP) and lipopolysaccharide (LPS), as well as lipid A, and liposomes.

In one aspect of the present application, adjuvants useful in any of the embodiments described herein are as follows. Adjuvants for parenteral immunization include aluminum compounds (such as aluminum hydroxide, aluminum phosphate, and aluminum hydroxy phosphate). The antigen can be precipitated with, or adsorbed onto, the aluminum compound according to standard protocols. Other adjuvants such as RIBI (ImmunoChem, Hamilton, Mont.) can also be used in parenteral administration.

Adjuvants for mucosal immunization include bacterial toxins (e.g., the cholera toxin (CT), the *E. coli* heat-labile toxin (LT), the *Clostridium difficile* toxin A and the pertussis toxin (PT), or combinations, subunits, toxoids, or mutants thereof). For example, a purified preparation of native cholera toxin subunit B (CTB) can be of use. Fragments, homologs, derivatives, and fusion to any of these toxins are also suitable, provided that they retain adjuvant activity. Preferably, a mutant having reduced toxicity is used. Suitable mutants have been described (e.g., in WO 95/17211 (Arg-7-Lys CT mutant), WO 96/6627 (Arg-192-Gly LT mutant), and WO 95/34323 (Arg-9-Lys and Glu-129-Gly PT mutant)). Additional LT mutants that can be used in the methods and compositions disclosed herein include, for example Ser-63-Lys, Ala-69-Gly, Glu-110-Asp, and Glu-112-Asp mutants. Other adjuvants (such as a bacterial monophosphoryl lipid A (MPLA) of various sources (e.g., *E. coli, Salmonella minnesota, Salmonella typhimurium*, or *Shigella flexneri*, saponins, or polylactide glycolide (PLGA) microspheres) can also be used in mucosal administration.

Adjuvants useful for both mucosal and parenteral immunization include polyphosphazene (for example, WO 95/2415), DC-chol (3 b-(N—(N',N'-dimethyl aminomethane)-carbamoyl) cholesterol (for example, U.S. Pat. No. 5,283,185 and WO 96/14831) and QS-21 (for example, WO 88/9336).

A subject may be immunized with a pharmaceutical composition comprising the chronic viral antigen, such as a HIV-1 antigen or HCV antigen, co-administered with an inhibitor of Tim-3 disclosed in the present application by any conventional route as is known to one skilled in the art. This may include, for example, immunization via a mucosal (e.g., ocular, intranasal, oral, gastric, pulmonary, intestinal, rectal, vaginal, or urinary tract) surface, via the parenteral (e.g., subcutaneous, intradermal, intramuscular, intravenous, or intraperitoneal) route or intranodally. Preferred routes depend upon the choice of the immunogen as will be apparent to one skilled in the art. The administration can be achieved in a single dose or repeated at intervals. The appropriate dosage depends on various parameters understood by skilled artisans such as the immunogen itself, the route of administration and the condition of the animal to be vaccinated (weight, age and the like).

The application also includes the use of an effective amount of a chronic viral antigen and an inhibitor of Tim-3 for inducing an immune response in a subject against a chronic virus and the use of an effective amount of a chronic viral antigen and an inhibitor of Tim-3 for manufacturing a medicament for inducing an immune response in a subject against a chronic virus. In addition, the application relates to a chronic viral antigen and an inhibitor of Tim-3 for use in inducing an immune response in a subject against a chronic virus.

Further, the application includes a method of treating or preventing a chronic viral infection, such as HIV-1 or HCV, in a subject comprising co-administering to said subject an effective amount of a chronic viral antigen, such as an HIV-1 antigen or HCV antigen, and an inhibitor of Tim-3.

As used herein, the phrase "treating or preventing a chronic viral infection" refers to inhibiting a chronic viral infection, preventing a chronic viral infection, decreasing the severity of a chronic viral infection, or improving signs and symptoms related to a chronic viral infection. In one embodiment, the chronic vial infection is an HIV-1 infection or an HCV infection.

The application also includes the use of an effective amount of a chronic viral antigen and an inhibitor of Tim-3 for treating or preventing a chronic viral infection in a subject and the use of an effective amount of a chronic viral antigen and an inhibitor of Tim-3 for manufacturing a medicament for treating or preventing a chronic viral infection in a subject. In addition, the application relates to a chronic viral antigen and an inhibitor of Tim-3 for use in treating or preventing a chronic viral infection in a subject.

The application also includes a soluble form of Tim-3 and methods and uses thereof. In one embodiment, the soluble form of Tim-3 comprises the amino acid sequence of SEQ ID NO:2 or 6. In another embodiment, the soluble form of Tim-3 consists of the amino acid sequence of SEQ ID NO:2 or 6.

A person skilled in the art will appreciate that the proteins of the invention, such as the soluble form of Tim-3 or other protein based inhibitors of Tim-3, may be prepared in any of several ways, but is most preferably prepared using recombinant methods.

Accordingly, nucleic acid molecules encoding the soluble form of Tim-3 or other protein based inhibitors of Tim-3 may be incorporated in a known manner into an appropriate expression vector which ensures good expression of the proteins. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", which means that the expression vectors contain a nucleic acid molecule of the application and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The application therefore contemplates a recombinant expression vector of the application containing a nucleic acid molecule encoding a soluble form of Tim-3 or other protein based inhibitors of Tim-3, and the necessary regulatory sequences for the transcription and translation of the inserted protein-sequence.

Suitable regulatory sequences may be derived from a variety of sources, including bacterial, fungal, viral, mammalian, or insect genes (For example, see the regulatory sequences described in Goeddel, Gene Expression Technology: Methods in Enzymology 185, Academic Press, San Diego, Calif. (1990)). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The recombinant expression vectors of the application may also contain a selectable marker gene which facilitates the selection of host cells transformed or transfected with a recombinant molecule of the application. Examples of selectable marker genes are genes encoding a protein such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the application and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of the target recombinant protein by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMal (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Recombinant expression vectors can be introduced into host cells to produce a transformed host cell. The terms "transformed with", "transfected with", "transformation" and "transfection" are intended to encompass introduction of nucleic acid (e.g. a vector) into a cell by one of many possible techniques known in the art. The term "transformed host cell" as used herein is intended to also include cells capable of glycosylation that have been transformed with a recombinant expression vector of the invention. Prokaryotic cells can be transformed with nucleic acid by, for example, electroporation or calcium-chloride mediated transformation. For example, nucleic acid can be introduced into mammalian cells via conventional techniques such as calcium phosphate or calcium chloride co-precipitation, DEAE-dextran mediated transfection, lipofectin, electroporation or microinjection. Suitable methods for transforming and transfecting host cells can be found in Sambrook et al.

(Molecular Cloning: A Laboratory Manual, 3rd Edition, Cold Spring Harbor Laboratory Press, 2001), and other laboratory textbooks.

Suitable host cells include a wide variety of eukaryotic host cells and prokaryotic cells. For example, the proteins of the application may be expressed in yeast cells or mammalian cells. Other suitable host cells can be found in Goeddel, Gene Expression Technology: Methods in Enzymology 185, Academic Press, San Diego, Calif. (1991). In addition, the proteins of the application may be expressed in prokaryotic cells, such as *Escherichia coli* (Zhang et al., Science 303 (5656): 371-3 (2004)). In addition, a *Pseudomonas* based expression system such as *Pseudomonas fluorescens* can be used (US Patent Application Publication No. US 2005/0186666, Schneider, Jane C et al.).

Yeast and fungi host cells suitable for carrying out the present application include, but are not limited to *Saccharomyces cerevisiae*, the genera *Pichia* or *Kluyveromyces* and various species of the genus *Aspergillus*. Examples of vectors for expression in yeast *S. cerevisiae* include pYepSec1 (Baldari. et al., Embo J. 6:229-234 (1987)), pMFa (Kurjan and Herskowitz, Cell 30:933-943 (1982)), pJRY88 (Schultz et al., Gene 54:113-123 (1987)), and pYES2 (Invitrogen Corporation, San Diego, Calif.). Protocols for the transformation of yeast and fungi are well known to those of ordinary skill in the art (see Hinnen et al., Proc. Natl. Acad. Sci. USA 75:1929 (1978); Itoh et al., J. Bacteriology 153: 163 (1983), and Cullen et al. (BioITechnology 5:369 (1987)).

Mammalian cells suitable for carrying out the present application include, among others: COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (Seed, B., Nature 329:840 (1987)) and pMT2PC (Kaufman et al., EMBO J. 6:187-195 (1987)).

Given the teachings provided herein, promoters, terminators, and methods for introducing expression vectors of an appropriate type into plant, avian, and insect cells may also be readily accomplished. For example, within one embodiment, the proteins of the application may be expressed from plant cells (see Sinkar et al., J. Biosci (Bangalore) 11:47-58 (1987), which reviews the use of *Agrobacterium rhizogenes* vectors; see also Zambryski et al., Genetic Engineering, Principles and Methods, Hollaender and Setlow (eds.), Vol. VI, pp. 253-278, Plenum Press, New York (1984), which describes the use of expression vectors for plant cells, including, among others, PAPS2022, PAPS2023, and PAPS2034).

Insect cells suitable for carrying out the present application include cells and cell lines from *Bombyx, Trichoplusia* or *Spodotera* species. Baculovirus vectors available for expression of proteins in cultured insect cells (SF 9 cells) include the pAc series (Smith et al., Mol. Cell Biol. 3:2156-2165 (1983)) and the pVL series (Lucklow, V. A., and Summers, M. D., Virology 170:31-39 (1989)). Some baculovirus-insect cell expression systems suitable for expression of the recombinant proteins of the application are described in PCT/US/02442.

Alternatively, the proteins of the application may also be expressed in non-human transgenic animals such as rats, rabbits, sheep and pigs (Hammer et al. Nature 315:680-683 (1985); Palmiter et al. Science 222:809-814 (1983); Brinster et al. Proc. Natl. Acad. Sci. USA 82:4438-4442 (1985); Palmiter and Brinster Cell 41:343-345 (1985) and U.S. Pat. No. 4,736,866).

The proteins may also be prepared by chemical synthesis using techniques well known in the chemistry of proteins such as solid phase synthesis (Merrifield, J. Am. Chem. Assoc. 85:2149-2154 (1964); Frische et al., J. Pept. Sci. 2(4): 212-22 (1996)) or synthesis in homogenous solution (Houbenweyl, Methods of Organic Chemistry, ed. E. Wansch, Vol. 15 I and II, Thieme, Stuttgart (1987)).

N-terminal or C-terminal fusion proteins comprising the soluble form of Tim-3 or other protein based inhibitors of Tim-3 conjugated with other molecules, such as proteins may be prepared by fusing, through recombinant techniques. The resultant fusion proteins contain a soluble form of Tim-3 or other protein based inhibitors of Tim-3 fused to the selected protein or marker protein as described herein. The recombinant protein of the application may also be conjugated to other proteins by known techniques. For example, the proteins may be coupled using heterobifunctional thiol-containing linkers as described in WO 90/10457, N-succinimidyl-3-(2-pyridyldithio-proprionate) or N-succinimidyl-5 thioacetate. Examples of proteins which may be used to prepare fusion proteins or conjugates include cell binding proteins such as immunoglobulins, hormones, growth factors, lectins, insulin, low density lipoprotein, glucagon, endorphins, transferrin, bombesin, asialoglycoprotein glutathione-S-transferase (GST), hemagglutinin (HA), and truncated myc.

Accordingly, the application provides a recombinant expression vector comprising the nucleic acid sequences that encode the soluble form of Tim-3 or other protein based inhibitors of Tim-3. Further, the application provides a host cell comprising the nucleic acid sequences or recombinant expression vectors disclosed herein.

In one embodiment, the term "isolated amino acid sequence" refers to an amino acid substantially free of cellular material or culture medium when produced by recombinant techniques.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present application:

EXAMPLES

Progressive loss of T cell functionality is a hallmark of chronic HIV-1 infection with viruses including HIV-1. A novel population of anergic T cells was identified in HIV-1 infection marked by surface expression of the glycoprotein Tim-3. The frequency of this population correlated positively with HIV-1 viral load, and inversely with $CD4^+$ T cell count. Blocking the Tim-3 signaling pathway using soluble Tim-3 restored proliferation and enhanced cytokine production in HIV-1-specific T cells. Thus the present inventors have uncovered a novel mechanism of HIV-1 induced T cell dysfunction, and presented a powerful opportunity for intervention.

Materials and Methods

Subjects.

Subjects were selected from participants in the Canadian Immunodeficiency Research Collaborative (CIRC) Cohort, Toronto, Canada, and the OPTIONS Cohort, University of California San Francisco (UCSF). The CIRC cohort represented acutely/early HIV-1 infected subjects, HIV-1-infected chronic progressors, and HIV-1-infected viral controllers. Acute/early subjects were defined as individuals infected with HIV-1 within the last 4 months. Chronic progressors were defined as individuals infected with HIV-1 for >1 year with $CD4^+$ T cell count decline>50 cells/mm$^3$/year. Viral controllers were defined as individuals infected with HIV-1>1 year, no evidence of $CD4^+$ T cell count decline, and viral load<5,000 copies/ml bDNA. Clinical data for the cohort employed in this study were: acute/early—absolute $CD4^+$ T cell counts (median, 542; range, 180-1240 cells/mm$^3$) and viral loads (median, 227,567; range, 79,000→500,000 copies/ml); chronic progressors—absolute $CD4^+$ T cell counts (median, 250; range, 132-660 cells/ml) and viral loads (median, 50,000; range, 290-500,000 copies/ml) and viral controllers—absolute $CD4^+$ T cell counts (median, 936; range, 600-1440 cells/mm$^3$) and viral loads (median, 100; range, 50-250 copies/mm$^3$). The subject with a viral load of 290 copies/ml, defined as a chronic progressor, was included in this patient group based on a $CD4^+$ T cell count that had declined to 200 cells/mm$^3$. The next lowest viral load in the chronic progressor group was 11,608 copies/ml. The chronic progressor with a relatively healthy absolute $CD4^+$ T cell count of 660 cells/mm$^3$ had a viral load of 51,250 copies/ml, and exhibited $CD4^+$ T cell count decline. The relatively high $CD4^+$ T cell count in this individual was likely to their relatively recent infection (13 months). Controls were obtained from HIV-1 uninfected patients in the same demographic area, with a similar age and sex profile, and were processed in an identical manner. OPTIONS Cohort: Baseline samples from all recruited subjects are evaluated to establish their HIV-1 infection status. Screened subjects must meet one of three criteria to be defined as having acute/early HIV-1 infection: (1) HIV-1 RNA>5,000 copies/ml with a negative or indeterminate HIV-1 antibody test, or; (2) a documented negative HIV-1 antibody test within 6 months with current seroconversion, or (3) a history compatible with acute/early HIV-1 infection with laboratory confirmation based on a non-reactive less sensitive antibody test. All subjects discuss the advantages and disadvantages of early antiretroviral therapy with study staff and arrangements are made for therapy for those who elect to initiate treatment; slightly over half of participants decline therapy. A total of 60 individuals with acute/early HIV-1 infection from the OPTIONS cohort were examined in this study; median $CD4^+$ T cell count of 544 (interquartile range 429.5, 721) cells/mm$^3$ and median HIV-1 viral load of 4.7 (interquartile range 3.66, 5.20) $\log_{10}$ copies/ml. Controls were obtained from HIV-1 uninfected patients from both the Stanford Blood Bank and from uninfected individuals from the cohort demographics. Additional subjects on HAART were recruited from these cohorts. This study was approved by the University of Toronto Institutional Review Board and by the UCSF Committee on Human Research and subjects gave written informed consent. Studies were performed on cryopreserved PBMCs immediately after thawing. At the initiation of this study a comparison between fresh and frozen PBMCs was performed and it was found that Tim-3 levels remained proportional after freezing/thawing. Culturing the cells overnight does however affect levels of Tim-3 expression, so it is important to minimize the time between thawing and staining.

Peptides and Stimulation Reagents.

Overlapping HIV-1 Clade B Gag and Nef pooled peptides (10 µg/ml) were obtained from the National Institutes of Health AIDS Research and Reference Reagent Program (Rockville, Md.). CEF (human Cytomegalovirus, Epstein Barr and Influenza Virus) pooled peptides (10 µg/ml) (Anaspec), SEB (Sigma), and purified anti-CD3 and anti-CD28 monoclonal antibodies (BD) were used as additional reagents.

Multicolor Cytokine Flow Cytometry.

PBMCs from healthy HIV-1 uninfected and HIV-1-infected individuals were stained with fluorophore-conjugated monoclonal antibodies to CD4, CD8, CD57, CCR7, CD27, CD45RA, CD25, Ki67 (BD), CD28, PD-1 (Biolegend), CD3 (Beckman Coulter), and TIM-3 (R&D Systems) to determine phenotype assessment. An Aqua amine dye (Invitrogen) was used as a discriminating marker for live and dead cells. In some experiments cells were stimulated after thawing with an HIV-1 Gag and Nef peptide pool, a CMV/EBV/influenza (CEF) peptide pool, or SEB followed by a fixation and permeabilzation step. Intracellular staining for cytokines was performed using anti-TNF-α and IFN-γ (BD). Cells were fixed in PBS+2% paraformaldehyde. Cells were acquired with a modified FACSAria, modified LSRII system, or FACSCalibur (Becton-Dickinson). A total of >100000 events were collected and analysed with FlowJo software (TreeStar). SPICE software (version 3.0, Mario Roederer, Vaccine Research Center, NIAID, NIH) was used to assist in the organization and presentation of multicolor flow data. (see below for Phospho flow cytometric methods)

Pentamer/Tetramer Analyses.

All pentamers were obtained from Proimmune Ltd, all tetramers were obtained from Beckman Coulter. Pentamers were used for the experiment displayed in FIG. 2, while tetramers were used for the experiment summarized in FIG. 7. Cryopreserved PBMC samples from chronically HIV-1 infected individuals were thawed, and washed with 2×10 ml of 1% FBS PBS with 2 mM EDTA. Staining was performed immediately after thawing with fluorophore conjugated antibodies against CD8 (BD), Tim-3 (R&D Systems), CD3 (BD), and the indicated pentamers (unlabled), followed by a secondary staining step with APC labeled pentamer fluorotags. Cells were washed 2× with 1% FBS PBS, and then fixed in 2% paraformaldehyde. Analysis was performed using a FACSCalibur instrument (BD Biosciences).

Synthesis of Recombinant Tim-3

The expression vector, pPA-TEV, was previously derived from pIRESpuro3 (Clontech), and modified to incorporate the transin leader sequence and N-terminal Protein A tag. The Tim-3 insert was obtained from PCR using the following primers

```
Tim-3-extF
                                              (SEQ ID NO: 3)
5' TTCGGCCGGCCCTCAGAAGTGGAATACAGAGCGG 3',
and Tim-3-extR
                                              (SEQ ID NO: 4)
5' TGAGCGGCCGCTCATCATCTGATGGTTGCTCCAGAGTC 3'.
```

For each primer the underlined bases represent the template annealing sequence. Additional 5' sequences comprise restriction sites and stop codons. The region amplified by these primers constitutes only the IgV and mucin domains of Tim-3. The resultant Tim-3 amplicon was cloned into the Fse I/Not I cloning site of pPA-TEV. 10 μg of circular DNA plasmid was then transfected into HEK293T cells using the calcium phosphate method (Invitrogen). Expression of Tim-3 was confirmed by Western blot using a 1/5000 dilution of a polyclonal anti-Tim-3 antibody (R&D Systems) and a 1/5000 dilution of HRP-conjugated streptavidin (Pierce). Transfection was then repeated with linearized pPA-TEV-Tim-3 plasmid to generate stable cell lines. A parallel transfection was performed with empty linearized pPA-TEV. Three days after transfection, puromycin drug selection was initiated by replacing the media with fresh media supplemented with 1 to 5□μg/ml puromycin. The media was exchanged with fresh puromycin containing media every 2 days. Ten days later 6 colonies from the pPA-TEV-Tim-3 transfection, and 6 from the pPA-TEV transfection were isolated and expanded into 6 well tissue culture plates. Secreted proteins were detected by Western blot analysis using an anti-Tim-3 antibody for pPA-TEV-Tim-3, and an anti-protein-A antibody for pPA-TEV. A Tim-3 secreting clone (pPA-TEV-Tim-3 transfected), and a control protein A secreting clone (pPA-TEV transfected) were selected and grown up in 2 L each of CHO-SFM-II media supplemented with 2% FBS, penicillin, streptomycin, HEPES, L-glutamine, and 1 ug/L apoprotinin (Sigma) in 6, T175 tissue culture flasks. Cells were plated at 50% confluency, and protein secretion was allowed to continue for 5 days. Supernatants were concentrated from 2 L to 10 ml using centricon plus 70 centrifugal filter units (Millipore). Proteins were purified using IgG Sepharose 6 Fast Flow beads (GE Healthcare) as per the manufacturer's instructions. 200 μl of 0.33 mg/ml His-tagged TEV protease were then added to the beads, and cleavage was allowed to proceed overnight at 4° C. Supernatants were removed from beads, the beads were washed 3× with 1 ml of TST, and supernatants were pooled with wash eluates. This combined eluate was passed through a 1 ml nickel column (B-PRE 6×His fusion protein purification kit, Pierce) to remove TEV protease, and washed with 3×2 ml of wash buffer 2 from the same kit. The eluates were subsequently passed through detoxi-gel endotoxin removal columns (Pierce) following manufacturer's instructions, and then concentrated to 0.5 ml using centricon plus-20 centrifugal filter units (Millipore). Volumes were then adjusted to 15 ml using sterile PBS, and reconcentrated to 0.5 ml. The purity and identity of products were confirmed by SDS-PAGE and Western blot analysis. Protein concentration was determined by a Bradford assay. As expected, only small amounts of residual protein were detectable in the protein-A control purification. This sample serves as a control for any effect of contaminant proteins, or reagents from the purification process on proliferation or cytokine production.

Proliferation Assay

To track cell division, PBMC from chronically HIV-1 infected individuals were labeled with 1 mM of the fluorescent intracellular dye, 5-(and -6) carboxyfluorescein diacetate, succinimidyl ester (CFSE; Molecular Probes) in PBS and mixed periodically for 10 minutes at room temperature. Labeling was quenched by addition of an equal volume of complete media (15% FBS in RPMI) for 2 minutes. The labeled cells were then washed twice, counted and resuspended in cell culture media. CFSE labeled cells were stimulated for 5-6 days with either DMSO alone, SLYNT-VATL peptide (SEQ ID NO:7), pooled HIV-1 derived Gag and Nef peptides or Cytomegalovirus, Epstein-Barr Virus, and Flu Virus (CEF) pooled peptides in the presence or absence of either sTim-3 or an equal volume of expression control. At the end of the culture period, cells were washed and incubated with a combination of the following conjugated anti-human monoclonal antibodies: CD4, CD8 (BD Biosciences, San Jose, Calif.), and. Intracellular staining for (IFN-γ, IL-2 (BD, San Diego, Calif.) and CD3 (Beckman Coulter, Fullerton, Calif.) was performed after cells were fixed and permeablized. Cells were then washed in PBC with 2 mM EDTA and 1% bovine serum albumin and then fixed in 1% paraformaldehyde before being run on an LSRII flow cytometer (BD Biosciences, San Jose, Calif.). Data was analyzed by using Flowjo Software version 6.4 (Treestar Inc, Ashland, Oreg.).

Signaling Analyses:

Prior to analyses of cellular signaling, archived PBMCs that had been viably frozen were thawed in 15 mL RPMI cell culture medium (Mediatech) containing 5% FBS (HyClone; RPMI+), washed in PBS containing 2% FBS (PBS+), and then rested at $5 \times 10^6$ cells/mL in RPMI+ at 37° C., 5% $CO_2$ over night. The following day, cells were washed with ice-cold PBS+, transferred to a 96-well V-bottom plate and stained for cell surface markers with fluorophore-conjugated monoclonal antibodies against CD3, CD8, CD27, CD45RA and Tim-3, on ice for 40 min. An amine-reactive dye (Invitrogen) was used to stain dead cells. After washing, cells were transferred to PBS containing IL-2 (SIGMA; final 100 ng/mL), or combination of phorbol 12-myristate 13-acetate (PMA) and ionomycin (P+I) (SIGMA; final 100 ng/mL and 1 μg/ml, respectively) at 37° C. to induce signaling. Signaling was arrested after 15, 30 and 45 min by immediate fixation, adding 4% paraformalehyde (final concentration 2%). After 20 min fixation and subsequent washing, cells were permeabilized in 70% ice cold methanol for 20 min on ice. Cells were washed and stained with an antibody cocktail containing phospho-specific antibodies: p-Erk1/2(pT202/pY204), pp38(pT180/pY182) and p-Stat5(pY694) (BD) for 60 min on ice. Before analysis, cells were washed and resuspended in PBS+ with 0.05% formaldehyde. The unstimulated control cells underwent the same manipulations. Cells were analyzed on a customized LSR II Flow Cytometer (BD). Analysis of data was performed using FlowJo (Tree Star). Fold changes in phosphorylation were calculated as the ratio of Median Fluorescence Intensity (MFI) of stimulated cells over unstimulated cells.

Quantitative PCR Primer sequences used as follows: TBP-for-GGGCATTATTTGTGCACTGAGA (SEQ ID NO:8), TBP-rev-TAGCAGCACGGTATGAGCAACT (SEQ ID NO:9), GATA-3-for-TGCATGACTCACTG-GAGGAC (SEQ ID NO:10), GATA-3-rev-TCAGG-GAGGACATGTGTCTG (SEQ ID NO:11), T-bet-for-GAGGCTGAGTTTCGAGCAGT (SEQ ID NO:12), T-bet-rev-CTGGCCTCGGTAGTAGGACA (SEQ ID NO:13), IFN-γ-for-TCCAAGTGATGGCTGAACTG (SEQ ID NO:14), IFN-□γ-rev-CTTCGACCTCGAAACAGCAT (SEQ ID NO:15). Manufacturers protocols were followed where applicable, unless otherwise noted. RNA was isolated from samples with Trizol (Invitrogen), resuspended in 44 μl DEPC water, and treated with DNAse using DNA-Free (Ambion Inc.). RNA concentrations were determined by spectrophotometry, and matched to the sample with the lowest concentration by dilution with DEPC treated water. 4 μl of RNA were used for each Superscript III First-Strand Synthesis SuperMix (Invitrogen) RT reaction with 1 μl 50 uM oligo(dT)$_{20}$. Parallel reactions lacking the RT enzyme were performed and consistently displayed no amplification in subsequent steps. Real-time PCRs were performed using the ABI Prism 7900HT (PE Applied Biosystems) in 384 micro-well plates. All samples, including the external standards, non-template control, and RT—controls were run in triplicate. Each 10 μl reaction contained 1×PCR buffer (Invitrogen), 3 mM MgCl2, 0.2 mM dNTP (Applied Biosystems), 1 nM forward and reverse primers (Invitrogen), ⅟50 dilution of ROX reference dye (Sigma-Aldrich Co.), ⅟100 000 dilution of SYBR Green I (Sigma-Aldrich Co.), 0.05 U of Platinum Taq polymerase (Invitrogen) and template DNA. Template was either a 7-fold serial dilution of gDNA for generation of standard curves, 5 μl of cDNA synthesis reactions, or 5 μl of matching RT—control. Reaction conditions were: 95° C. for 3 min, followed by 36 cycles of: 95° C.-15 s, 64° C.-15 s, 72° C.-20 s. A final dissociation stage was run to generate a melting curve for verification of amplification product specificity. Real-time PCR was monitored and analyzed by the Sequence Detection System version 2.0 (Applied Biosystems).

Statistical Analyses:

Mixed effects longitudinal analyses were used to determine if CD8+ T cell activation levels independently associated with Tim3 percentage on CD8+ T cells during antiretroviral therapy. A random effect for time and the individual was specified. The models were run in the SAS System 9.2 under Proc Mixed. Other statistical tests employed are identified in corresponding figure legends.

Results and Discussion

Tim-3 expression on PBMC was profiled from 9 HIV-1-uninfected subjects by flow cytometry using both monoclonal and polyclonal antibodies. Tim-3 was uniformly expressed on monocytes (FIG. 11 A-C), highly expressed in the CD3⁻ lymphocyte population, and expressed at lower frequencies on CD8+, CD4+ T cells and NKT cells (FIGS. 1 A, B, E, F, and 11 D, E). In a cohort of HAART naïve, acute/early and chronically infected HIV-1 infected patients, that included both viral controllers (non-progressors) and progressors, elevated frequencies of Tim-3 expressing CD8+ T cells was observed in acute/early, and chronic progressive HIV-1 infected individuals, but not in viral controllers, relative to uninfected individuals (28.5±6.8% for HIV-1 uninfected versus 49.0±16.2% for chronic progressors, p=0.0008; 52.8±17.5% for acutely/early infected individuals, p=0.0015; and 31.6±4.5%, p=0.48) (FIG. 1 A-H). Elevated Tim-3 expression on CD4+ T cells from chronic-progressive HIV-1-infected individuals were also observed when compared to both viral controllers and HIV-1 uninfected individuals (FIG. 1 A-H).

Figure 12B:
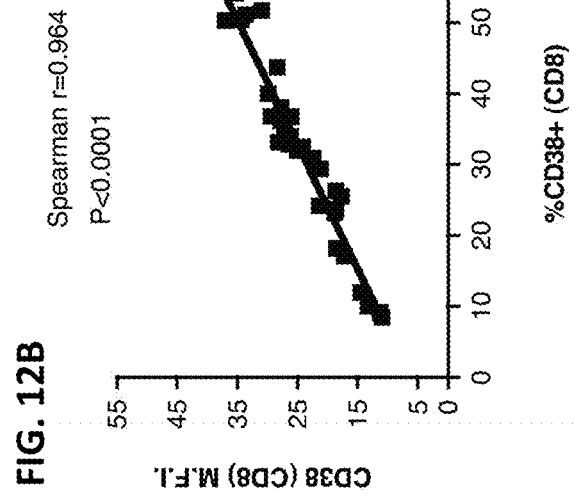
FIGS. 12A-12C show the correlation of the frequency of surface Tim-3 expression on CD8⁺ T cells from HIV-1 infected individuals as determined by either a rabbit monoclonal antibody (X-axis) or goat polyclonal antibodies (Y-axis) against Tim-3.
Figure 12A:
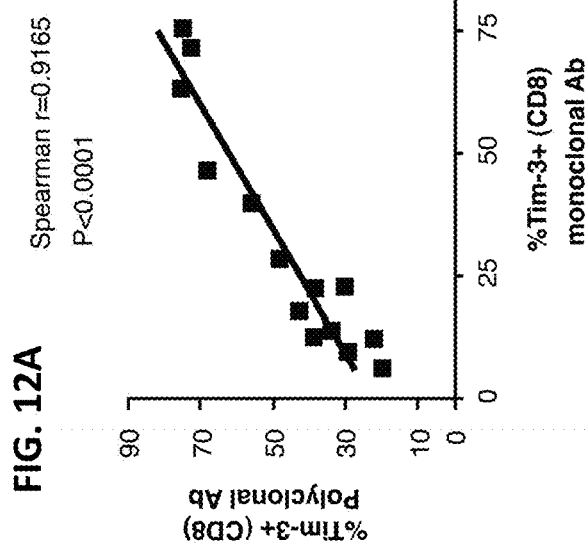
Figure 12C:
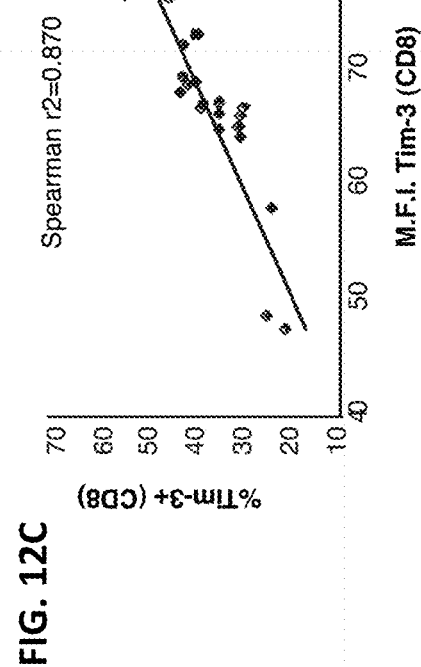

Since HIV-viral load and CD4 count predict disease progression, the relationship between Tim-3 expression and these surrogate markers was examined. A significant positive correlation was observed between the frequency of Tim-3+ CD8+ T cells and HIV-1 viral load (p<0.0001, FIG. 1I), and an inverse correlation with absolute CD4+ T cell counts (p=0.0397, p<0.05, FIG. 1J). Similarly, the frequencies of Tim-3+ CD4+ T cells were also significantly associated with viral load (p=0.0087) and absolute CD4+ T cell counts (0.0273) (FIG. 1 L, M). The status of T cell activation as reported by CD38 expression is an additional strong predictor of disease progression (24). CD38 expression on CD8+ T cells correlated with levels of Tim-3 expression on CD8+ T cells (p<0.0001, FIG. 1K), while CD38 expression on CD4+ T cells correlated with levels of Tim-3 expression on CD4+ T cells (p<0.05, FIG. 1N). In acute/early and chronic progressive HIV-1 infection, increased expression of both Tim-3 and CD38 manifested as a frequent dual Tim-3+ CD38+ population of CD8+ T cells (FIG. 1I). In a separate cohort of 60 treatment naïve, acutely/early HIV-1-infected individuals (OPTIONS cohort), an analogous increase was observed in the frequency of Tim-3+ CD8+ and CD4+ T cells as assessed with a monoclonal anti-Tim-3 antibody (FIG. 1H, FIG. 12A). Similar positive correlations between HIV-1 viremia, CD38 and Tim-3 expression on T cells were also observed in this acute/early infection cohort (FIG. 1 O-R).

Figure 2E:
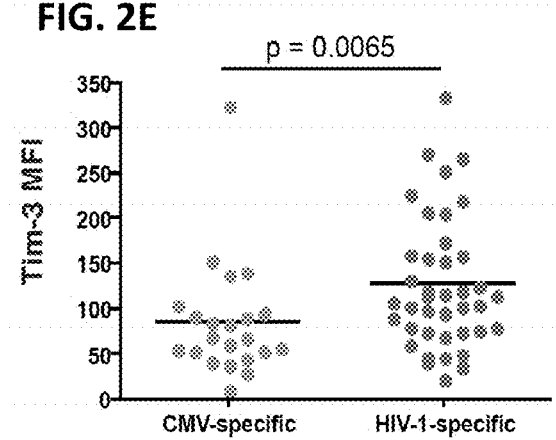
Figure 2F:
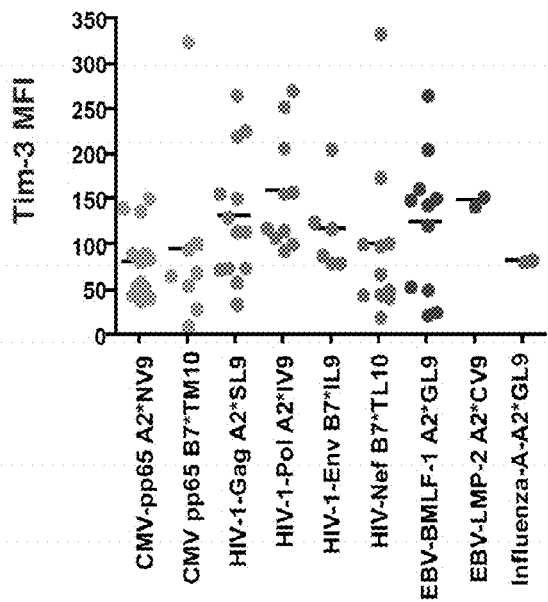
Figure 2G:
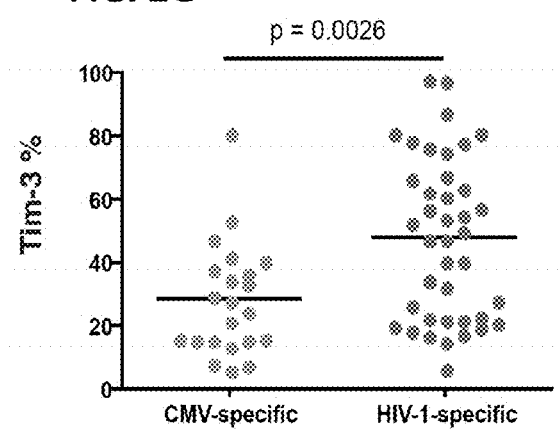
Figure 2H:
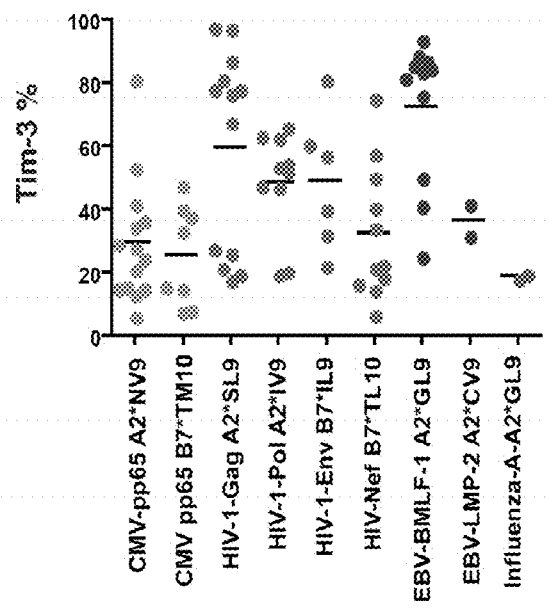

Next levels of Tim-3 expression was determined on EBV-GLCTLVAML (SEQ ID NO: 17), CMV-NLVPM-VATV (SEQ ID NO: 16), HIV-1-Gag-SLYNTVATL (SEQ ID NO: 7), and HIV-1-Pol-ILKEPVHGV (SEQ ID NO: 18) specific CD8+ T cells in 9 HLA A*0201+, HLA-B*0702+, and HLA-B*0801+ chronically HIV-1 infected individuals using matched MHC-I pentamers. Significantly higher levels of Tim-3 were observed on HIV-1-specific versus CMV-specific CD8+ T cells (p=0.0065 by MFI, p=0.0026 by % Tim-3+) (FIG. 2A-H). CMV-specific CD8+ T cells exhibited low levels of Tim-3 expression, with the exception of one response to CMV-pp65-TPRVTGGGAM (SEQ ID NO: 19), which exhibited high levels of Tim-3 expression as measured by MFI, observed in cells from an individual with AIDS (Abs CD4 count=132 cells/μl). Tim-3 expression was heterogeneous amongst HIV-1-specific responses with some exhibiting very high levels of Tim-3, while others exhibited only baseline levels (FIG. 2F,H). The heterogeneity observed in Tim-3 expression levels on HIV-1-specific CD8+ T cells cannot be attributed solely to inter-subject variability, as responses with high levels of Tim-3 expression were frequently observed contemporaneously with responses exhibiting low levels of Tim-3 expression within the same individual.

Figure 13A:
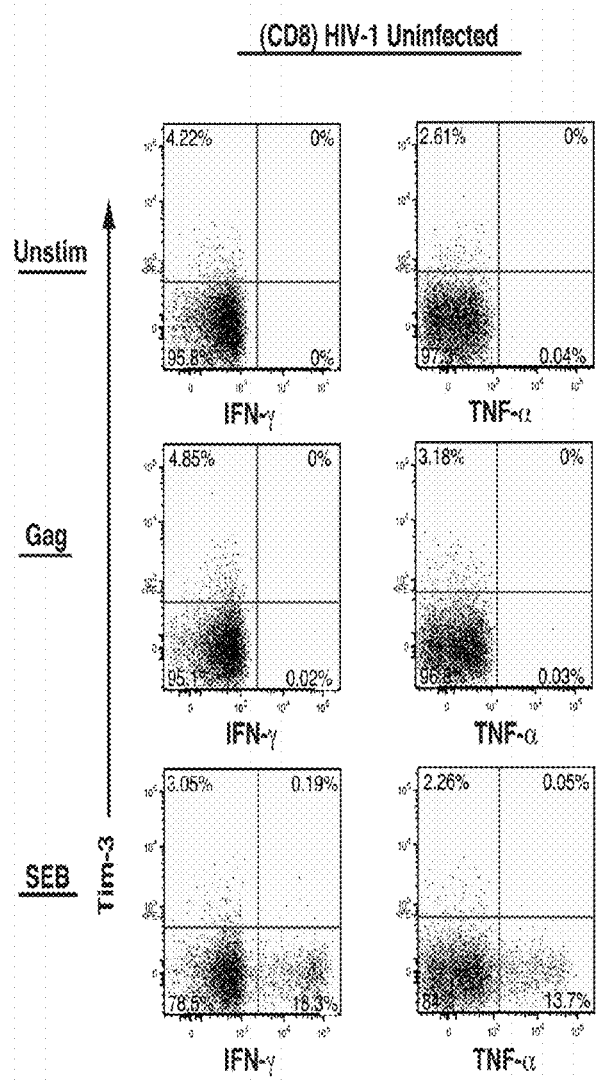
FIGS. 13A-13B show analogous patterns of cytokine production were observed for acutely/early infected individuals, chronic progressors, viral controllers, and HIV-1-uninfected subjects.
Figure 13B:
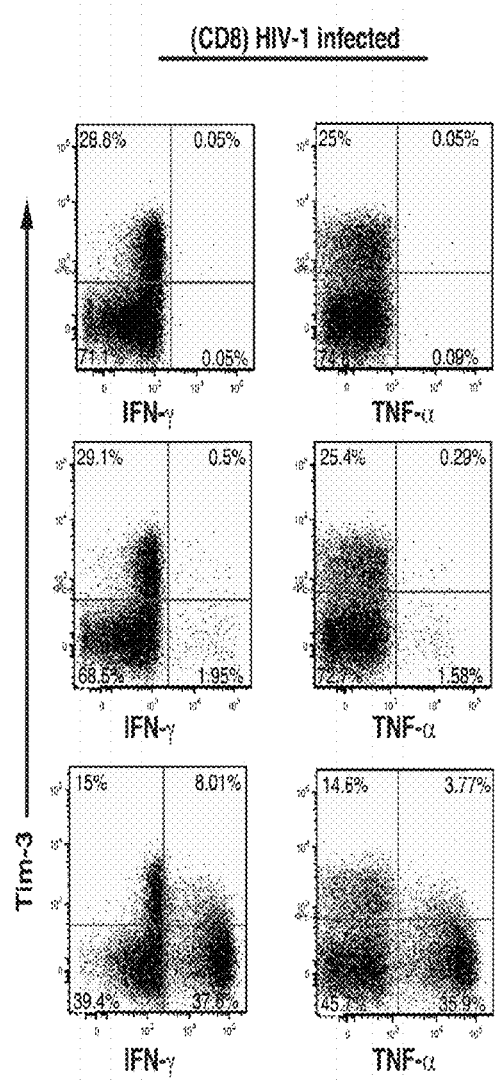

Using PBMC from both HIV-1-infected and uninfected individuals, Tim-3+ populations were sorted from Tim-3⁻ populations within both CD8+ and CD4+ T cell subsets and T-bet ($T_{h1}$), GATA-3 ($T_{h2}$), and IFN-γ ($T_{h1}$) mRNA was quantified by qPCR. For both CD8+ and CD4+ T cell populations, GATA-3 was expressed at higher levels in the Tim-3⁻ fraction than in the Tim-3+ fraction, while T-bet was more highly expressed in the Tim-3+ population (FIG. 4). Despite the $T_{h1}/T_{c1}$ character of Tim-3+ cells, the majority of IFN-γ mRNA was detected in the Tim-3⁻ CD8+ population. IFN-γ and TNF-α production was then examined in response to stimulation with pooled HIV-1-Gag peptides, CMV/EBV/Influenza (CEF) peptides, or *staphylococcus* enterotoxin B (SEB) in PBMC from 10 acutely/early HIV-1-infected individuals, 10 chronic progressors, 10 viral controllers, and 5 HIV-1-uninfected individuals. In both HIV-1-infected and uninfected subjects, IFN-γ production from CD4+ and CD8+ T cells in response to stimulation was observed predominately from the Tim-3⁻ population with minimal cytokine production observed in either the Tim-3$^{lo}$ or Tim-3$^{hi}$ populations (FIG. 5 A-D). Analogous patterns of cytokine production were observed for acutely/early infected individuals, chronic progressors, viral controllers, and HIV-1-uninfected subjects (FIG. 13 A-B). TNF-α and CD107a expression in response to antigen were similarly restricted to Tim-3⁻ cells (FIG. 13 A-B, FIG. 14 A-D). As a corollary, HIV-1-specific CD8+ T cells were identified by staining with MHC-I tetramers and observed that, in response to cognate peptide, IFN-γ was produced only by the Tim-3$^{-/lo}$ fraction, with no IFN-γ production from tetramer+ Tim-3$^{hi}$ cells (FIG. 5 E-G). Thus, the lack of cytokine secretion from the Tim-3$^{hi}$ population cannot be attributed to an absence of antigen specific cells.

Tim-3$^{+/hi}$ cells were subsequently sorted from Tim-3$^{-/lo}$ cells using ex vivo PBMC from untreated chronic progressor HIV-1 infected individuals. Both subsets were stimulated with anti-CD3 and anti-CD28, and proliferation was assessed by CFSE dilution. Proliferation of the Tim-3$^{-/lo}$ cells was observed, while minimal proliferation was detected in the Tim-3$^{hi}$ population (FIG. 5H-L). Ex vivo PBMC from 5 HIV-1-uninfected individuals and 5 HIV-1-infected chronic progressors were contained with Tim-3 and Ki67 antigen. Ki67 antigen is a nuclear protein that is generally expressed only in cells in late $G_1$, S, $G_2$ and M phases of cell cycle (30), hence it is generally used as a marker of proliferating cells. In chronic HIV-1 infection, however, it has been demonstrated that the large majority (92±5%) of Ki67$^+$ T cells in peripheral blood are activated cells that are arrested in the $G_0/G_1$ phases of cell cycle (31). A number of studies have noted that Ki67 expression on T cells from HIV-1-infected individuals is associated with dysfunction or anergy (32-34). In line with previous studies, elevated frequencies of Ki67$^+$ cells were observed in both the CD4$^+$ and CD8$^+$ T cell subsets of HIV-1-infected versus uninfected PBMC (35) (FIG. 5 M-N). While the large majority of Tim-3$^+$ cells were Ki67$^-$, Ki67$^+$ CD8$^+$ and CD4$^+$ T cells were greatly enriched for Tim-3 expressing cells (FIG. 5R, p=0.0159). Expression of Tim-3 on this population, which has been characterized as activated but arrested in cell-cycle, is consistent with in vitro data showing a lack of proliferation of Tim-3 expressing cells. Taken together, these studies indicate that Tim-3 expression defines a population of activated, but dysfunctional T cells in HIV-1 infection.

Figure 6E:
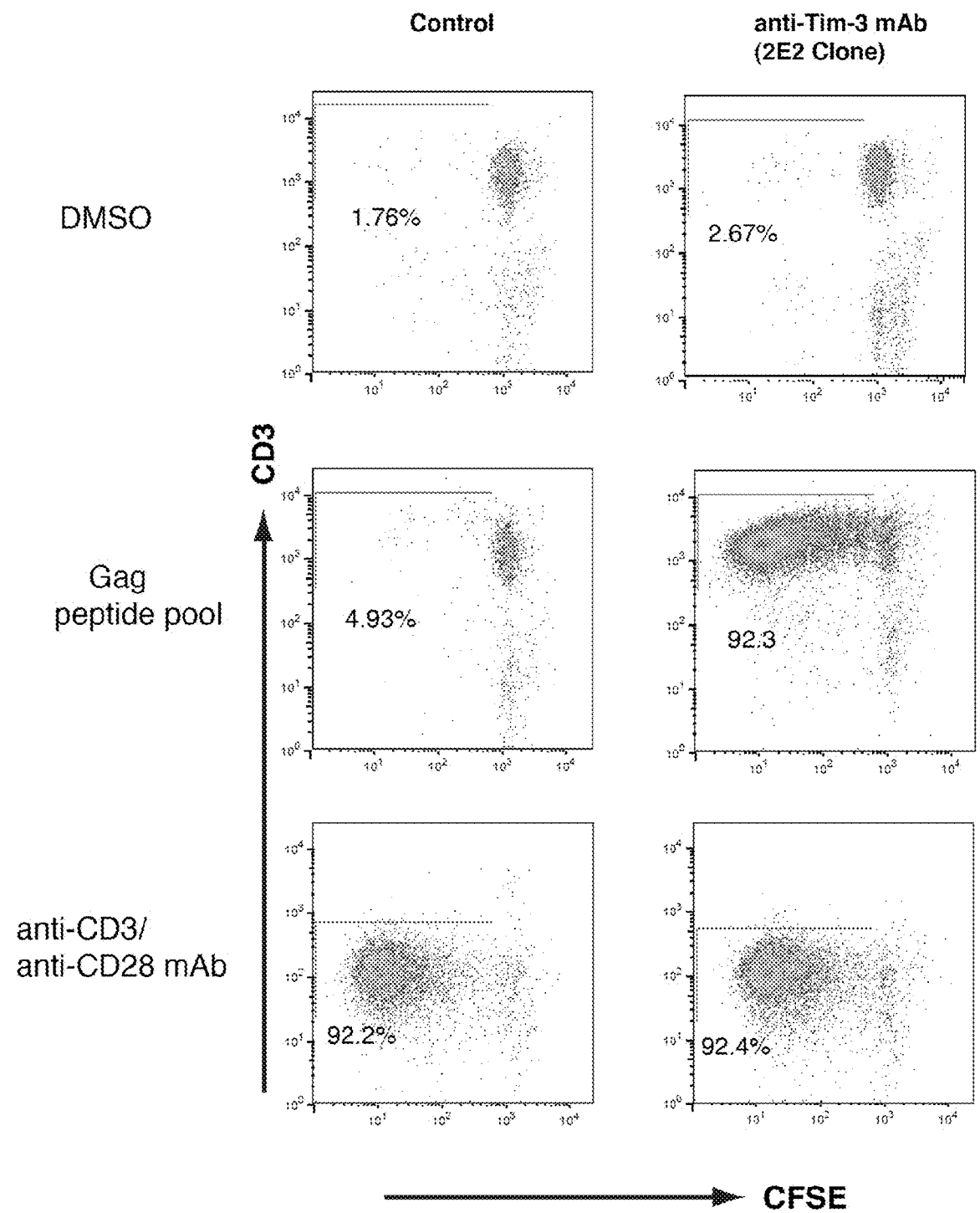
Figure 15:
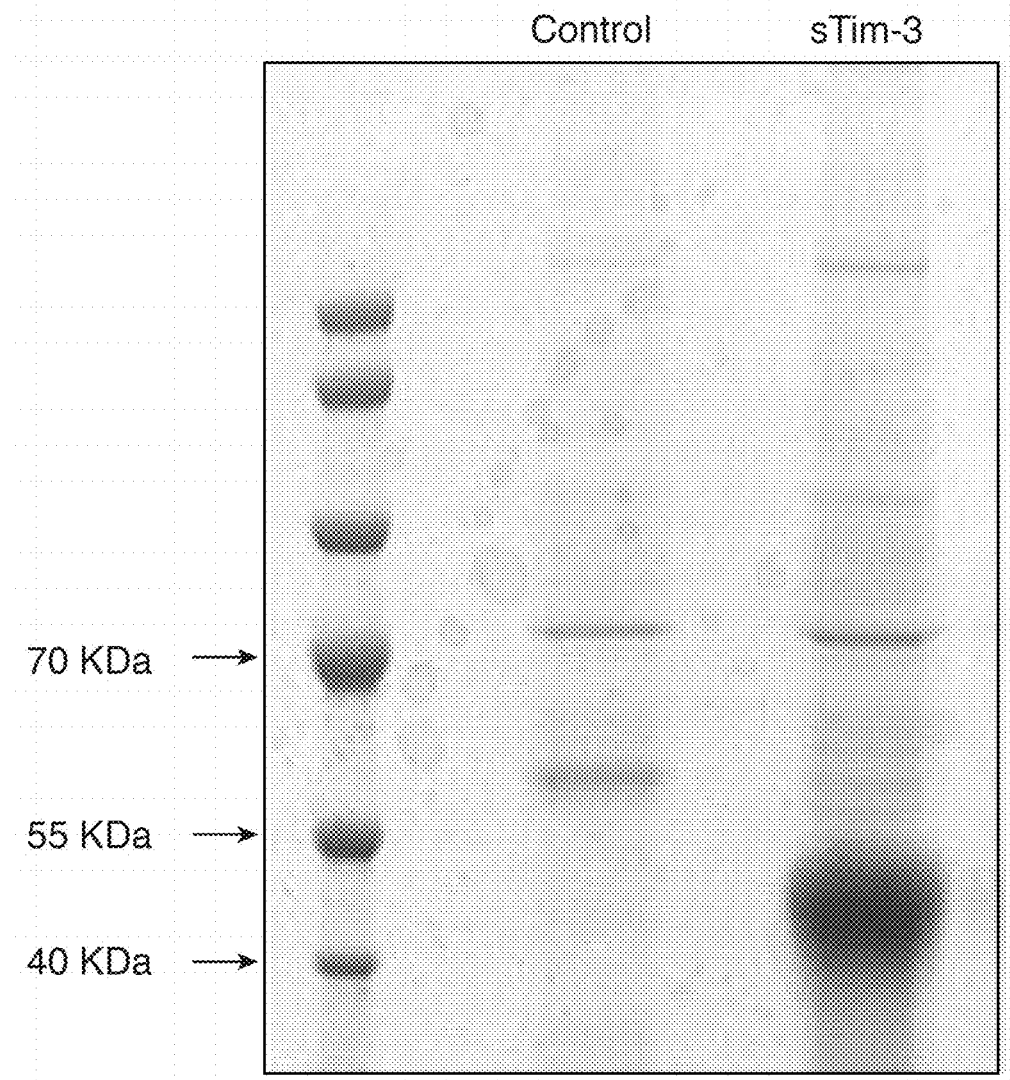
FIG. 15 is a silver-stained SDS PAGE of purified soluble Tim-3 (lane 3) and an expression control (lane 2).
Figure 16:
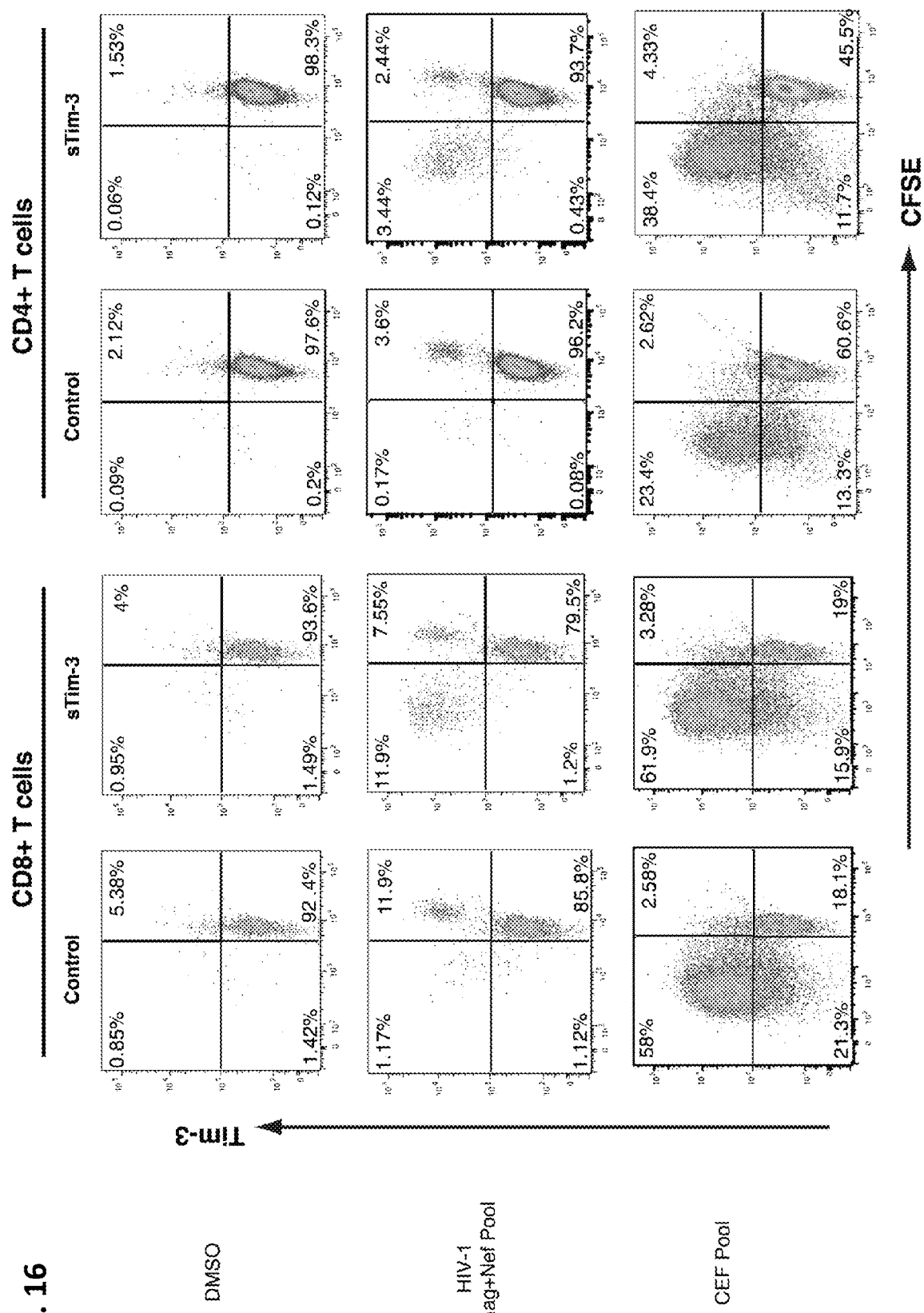
FIG. 16 shows the cells which had undergone proliferation in vitro exhibited high levels of Tim-3 expression FIG. 17 demonstrates that in the presence of sTim-3 the cells in FIG. 16 consistently express higher levels of IFN-γ than in the presence of a control.
Figure 17:
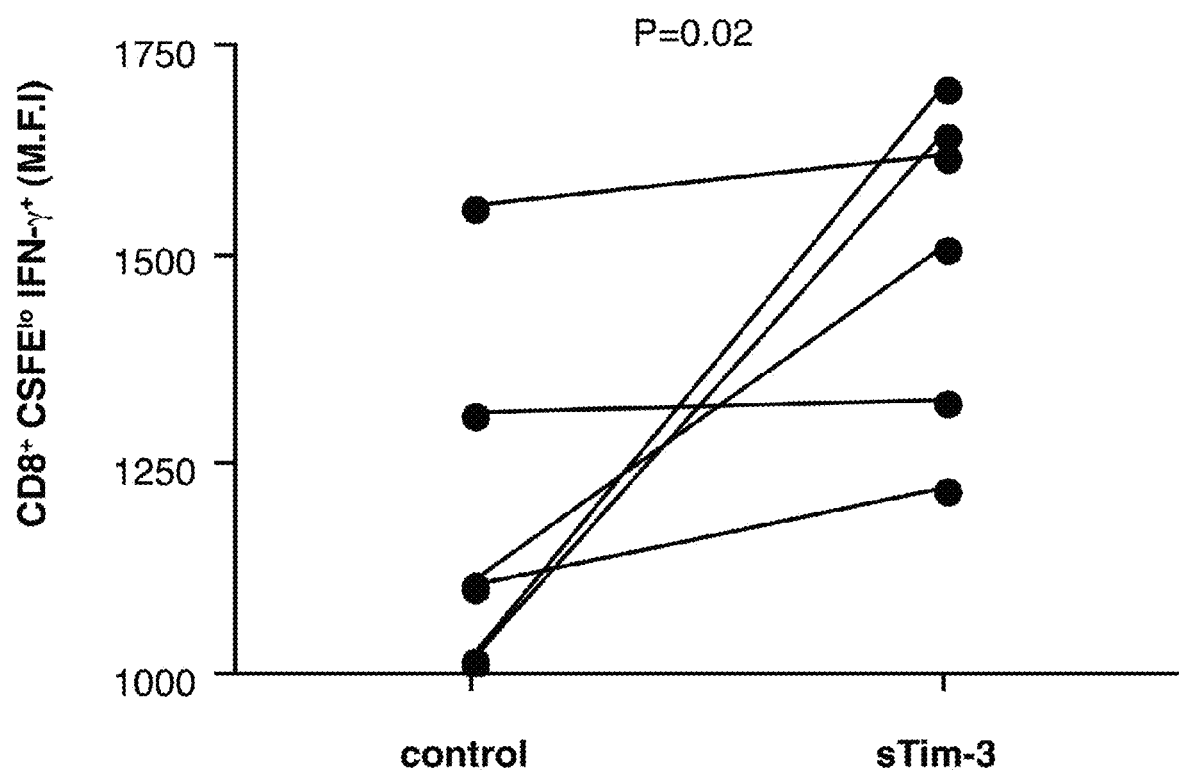
Figure 18:
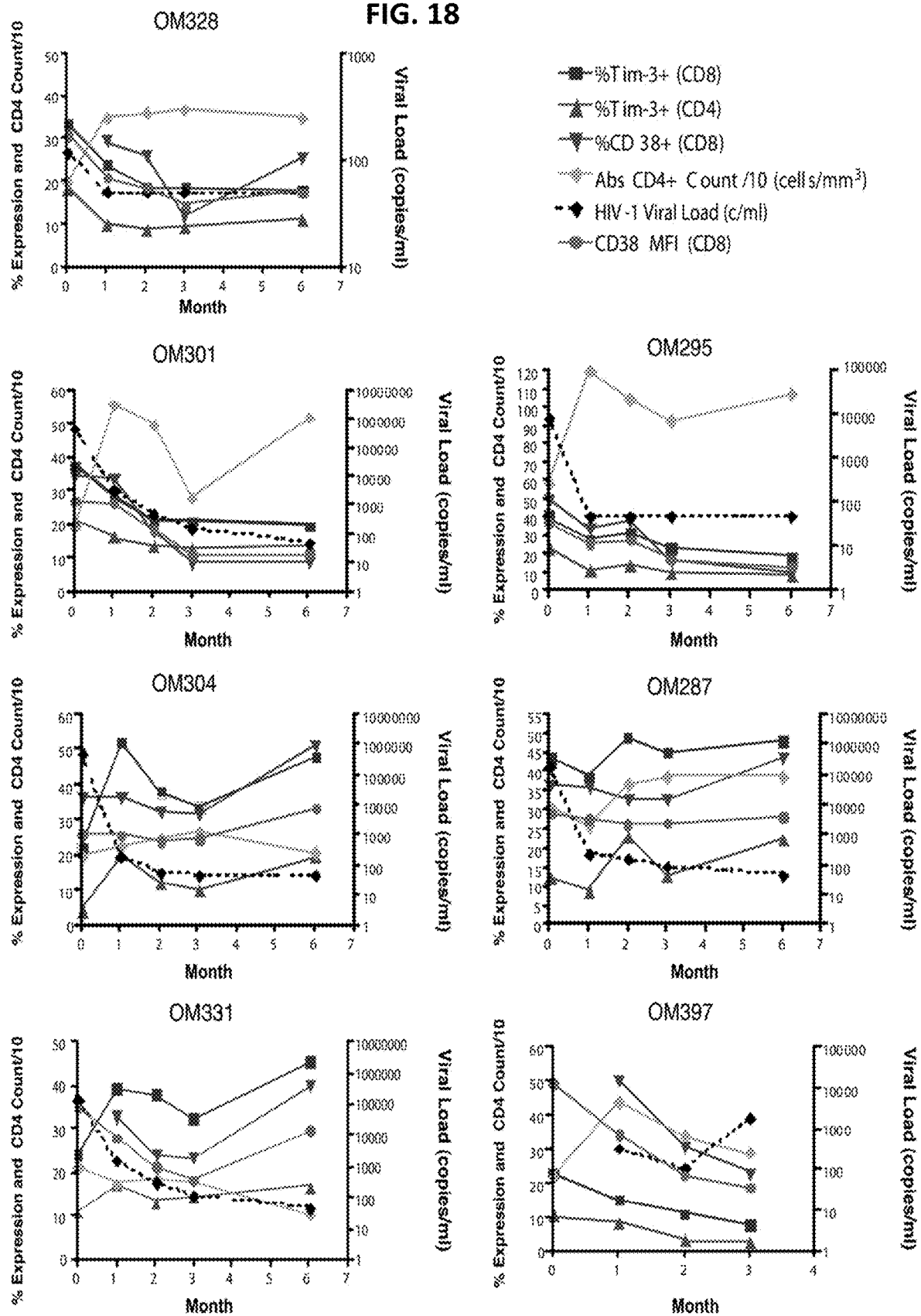
FIG. 18 shows the effect of HAART on levels of Tim-3 expression in Chronic HIV-1 infection. Seven chronically HIV-1-infected individuals from the CIRC cohort were sampled at baseline and at 1, 2, 3 and 6 months post-initiation of HAART. Shown are Tim-3 and CD38 expression levels as determined by flow cytometry, along with absolute CD4+ T cell count and HIV-1 viral load clinical data. Absolute CD4+ T cell count is displayed as cells/mm3 divided by 10.

To delineate the causal relationship between Tim-3 expression and T cell dysfunction, it was tested whether blocking the interaction of Tim-3 with its ligand(s) would restore proliferation, and cytokine production of Tim-3$^+$ cells. In mice, galectin-9 has been identified as a carbohydrate dependent ligand for Tim-3 (10). In humans it has been suggested that Tim-3 may also have an as of yet unidentified, carbohydrate independent ligand (5). To ensure a comprehensive block of Tim-3 signaling, a recombinant soluble Tim-3 glycoprotein was employed to saturate all Tim-3 binding ligands (FIG. 15). Addition of sTim-3 enhanced the expansion of CD8$^+$ T cells specific for the HLA-A*0201 restricted HIV-1-Gag epitope 'SLYNTVATL' (SL9) (SEQ ID NO: 7) in HIV-1-infected chronic progressors in a dose-dependent manner up to 2 µg/ml (FIG. 6A). Enhanced proliferation of both CD8$^+$ and CD4$^+$ T cells was also observed when PBMC from chronic progressors were stimulated with pooled Gag and Nef peptides (FIG. 6B-D). These data were corroborated by employing a blocking anti-Tim-3 mAb clone (2E2) to disrupt the Tim-3 pathway in an analogous proliferation assay experiment. Addition of 10 µg/ml of mAb 2E2 resulted in a profound rescue of HIV-1-Gag T cell proliferative responses (FIG. 6E). An additional observation from these experiments is that cells which had undergone proliferation in vitro exhibited high levels of Tim-3 expression (FIG. 16). Tim-3 upregulation in response to anti-CD3/anti-CD28 was observed as early as 20 hours after stimulation, and progressively increased out to at least 120 hours. This is consistent with Tim-3 acting as a negative immune regulator, where antigen stimulated cells perform effector functions and then upregulate Tim-3 as a means of terminating responses. In reconciling the ex vivo data showing a lack of cytokine production from Tim-3$^+$ cells with published in vitro data demonstrating an association between IFN-γ production and high levels of Tim-3 expression there is an important distinction to make. Cells expressing Tim-3 ex vivo have been subjected to chronic stimulation in vivo and are dysfunctional to further in vitro stimulation. In contrast, when Tim-3$^-$ cultured cells are stimulated in vitro they perform effector functions, such as produce IFN-γ, and then upregulate Tim-3 to dampen these responses. Thus, depending on when one observes these cultures, high levels of Tim-3 and IFN-γ could be observed in association. This model predicts that in addition to restoring functions of exhausted HIV-1-specific T cells, in vitro treatment with sTim-3 should prolong effector function in response to other antigens. This is supported by examining the level of IFN-γ production at day 5 of in vitro stimulation with anti-CD3/CD28. Under these conditions, all cells that have undergone division express high levels of Tim-3. In the presence of sTim-3 these cells consistently express higher levels of IFN-γ than in the presence of a control (FIG. 17).

Figure 7C:
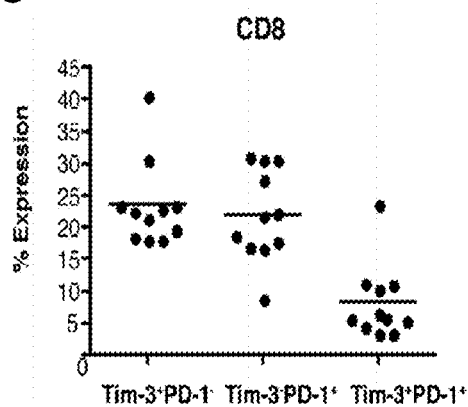
Figure 7D:
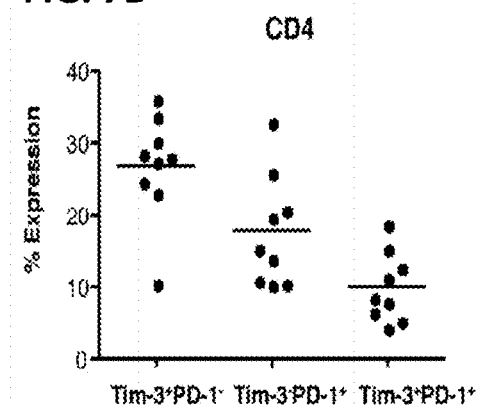
Figure 7E:
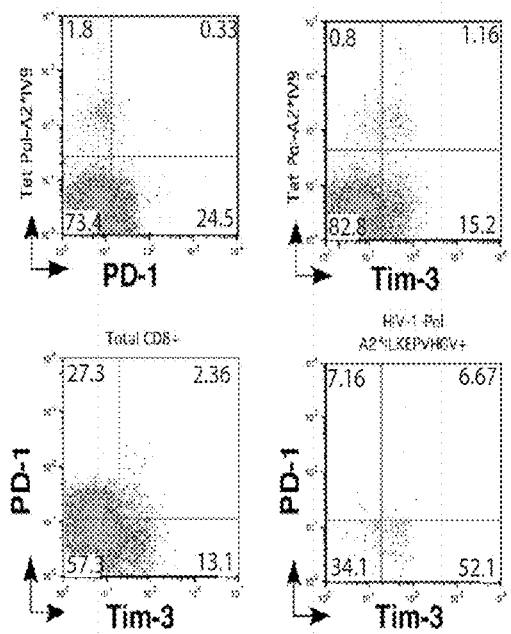
Figure 7F:
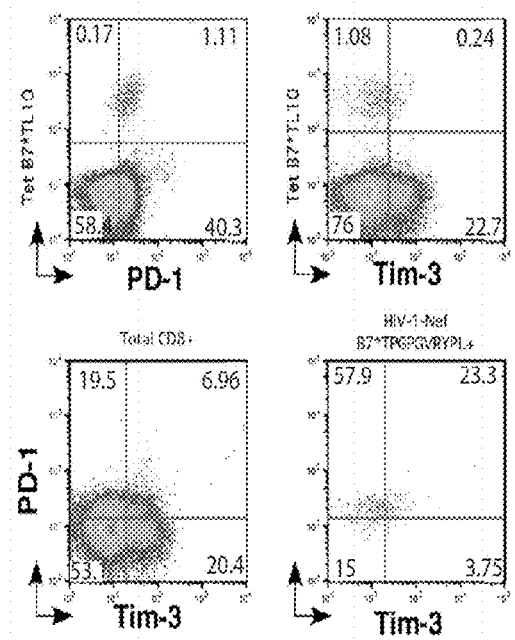
Figure 8A:
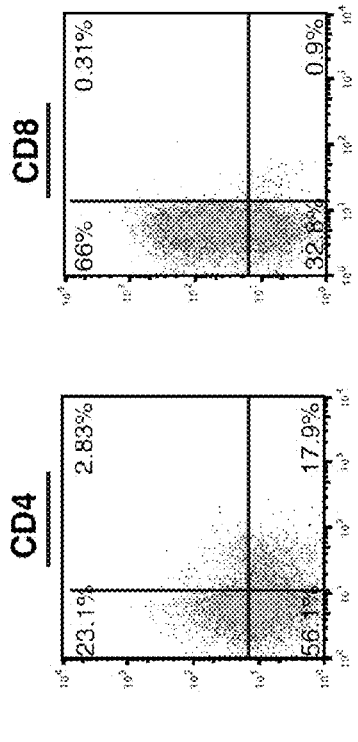
FIGS. 8A-8B show dual staining for Tim-3 and CD25 on both CD4⁺ and CD8⁺ T cells. Tim-3 and CD25 were primarily expressed by distinct populations of T cells and demonstrate that Tim-3 expression on CD4⁺ T cells does not mark a population of classical regulatory T cells.
Figure 8B:
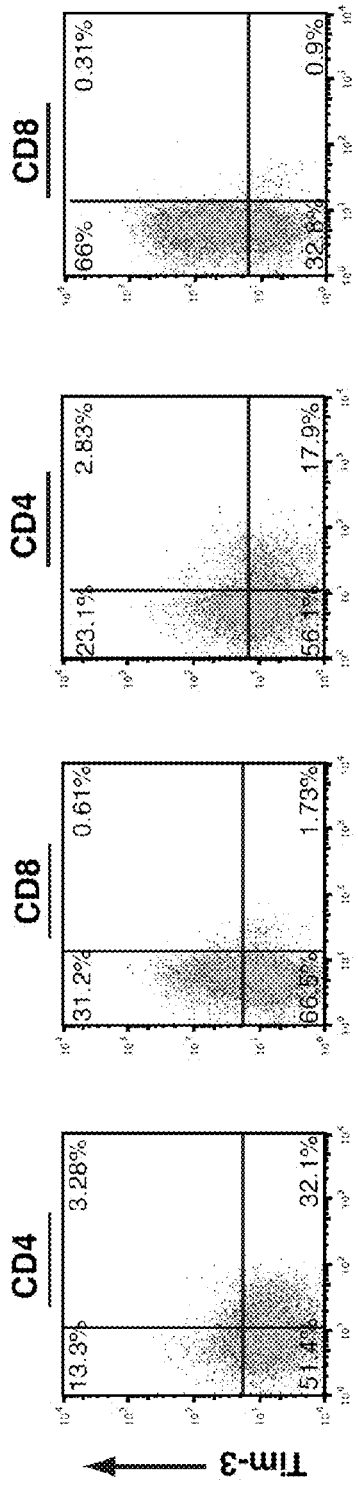
Figure 8C:
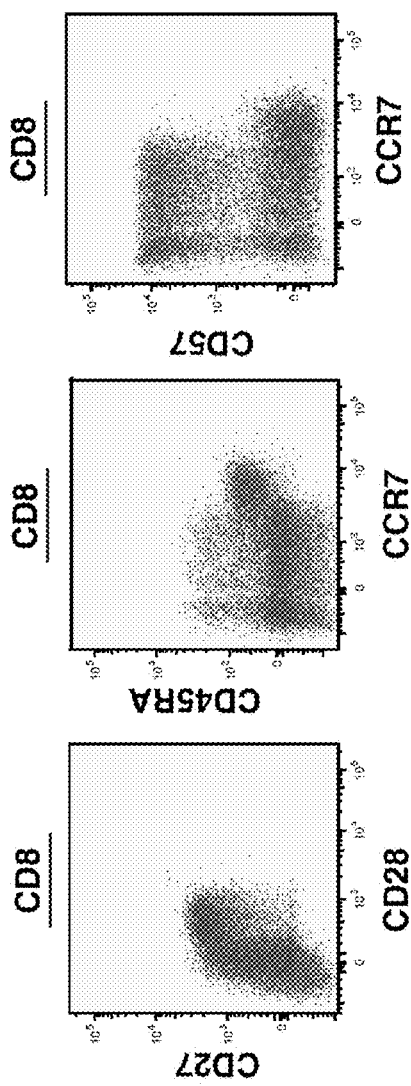
(FIGS. 8C-8E) Demonstrates a phenotypic flow cytometry assessment of Tim-3⁺ (FIG. 8D) versus Tim-3⁻ (FIG. 8E) CD8⁺ T cells subpopulations from chronically HIV-1 infected individuals. PBMCs were stained with monoclonal antibodies against Tim-3, CD3, CD8, CD28, CD27, CD45RA, CCR7 and CD57, as well as with a dead cell discriminating marker. Gating was first performed to include only the viable, CD3⁺CD8⁺ population in subsequent analysis. Gating for maturation/differentiation markers was determined based on fluorescence minus one controls, and results were analyzed using SPICE software. Shown are the frequencies of populations with the corresponding combination of phenotypic markers, with each individual represented by a single bar. These data support that Tim-3 expressing CD8⁺ T cells from chronically HIV-1-infected individuals were distributed across a range of phenotypic profiles.
Figure 8D:
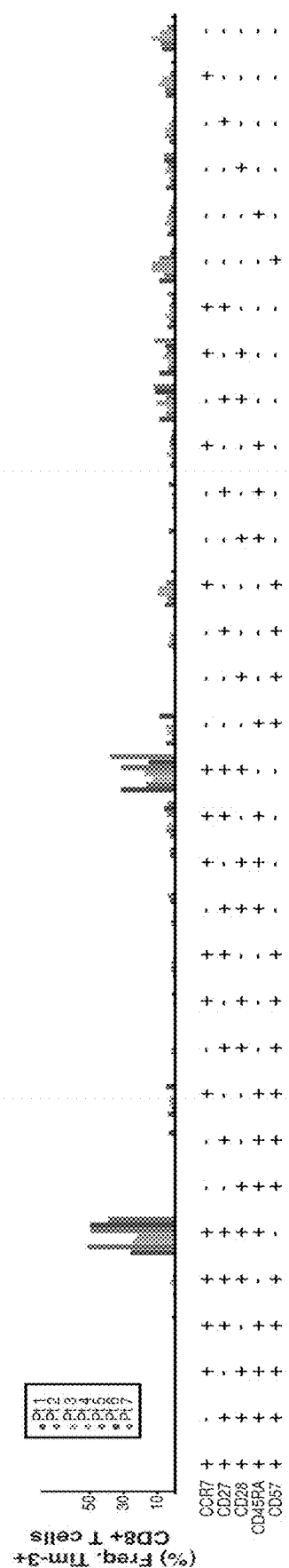
Figure 8E:
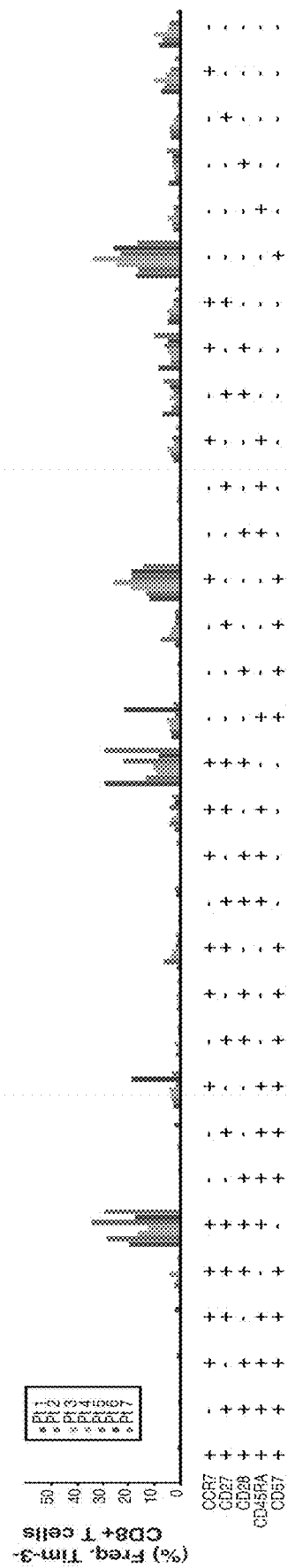

Since PD-1 has previously been identified as a marker of exhausted HIV-1-specific T cells, it was determined whether Tim-3 expression represents a second marker of this same exhausted population, or defines a distinct population. PBMC from 10 individuals with chronic progressive HIV-1 infection were co-stained for Tim-3 and PD-1. Expression was analyzed by flow cytometry after gating on CD8$^+$ or CD4$^+$ T cells (FIG. 7). In 9/10 subjects, Tim-3 and PD-1 were primarily expressed by distinct populations of CD8$^+$ T cells. One subject, OM513, displayed a frequent Tim-3$^+$ PD-1$^+$ population (23.6%), but retained both Tim-3$^+$ PD-1$^-$ and Tim-3$^-$PD-1$^+$ populations (23.0% and 16.7% respectively). Similarly 9/10 subjects showed primarily divergent staining for PD-1 and Tim-3 on CD4$^+$ T cells (FIG. 7C,D). In HIV-1-specific CD8$^+$ T cells, two patterns of expression were observed: tetramer$^+$ populations were predominantly Tim-3$^+$ PD-1$^-$ (FIG. 7E), or they were predominantly Tim-3$^-$ and PD-1$^+$ (FIG. 7F). In both patterns, a minority population co-expressed both Tim-3 and PD-1 (FIG. 7E,F). Thus Tim-3 and PD-1 expression define primarily distinct populations. Dual staining for Tim-3 and CD25 was performed on both CD4$^+$ and CD8$^+$ T cells (FIG. 8A, B). Tim-3 and CD25 were primarily expressed by distinct populations of T cells. These data demonstrate that Tim-3 expression on CD4$^+$ T cells does not mark a population of classical regulatory T cells. It was then determined if the Tim-3$^{hi}$ population could be defined by other cell surface markers that have been used to define the maturation/differentiation status of T cells, by co-staining for CD57, CD45RA, CD27, CD28, and CCR7 (26-28, 36). Tim-3 expressing CD8$^+$ T cells from chronically HIV-1-infected individuals were distributed across a range of phenotypic profiles (FIG. 8C-E).

The kinetics of STAT5, Erk and p38 phosphorylation (pSTAT5, pErk and p38 respectively) were assessed after stimulation in Tim-3$^{hi}$ versus Tim-3$^{-/lo}$ CD8$^+$ T cells in three HIV-1 infected individuals (37). Tim-3$^{hi}$ CD8$^+$ T cells had higher levels of basal phosphorylation of STAT5, p38 and ERK1/2 compared to Tim-3$^{-/lo}$ CD8$^+$ T cells, and exhibited lower fold changes in the phosphorylation of these molecules when stimulated in vitro, with: IL-2 for the STAT5 pathway, and PMA/Ionomycin (P+I) for p38 and ERK1/2 (MAP kinase pathway) (FIG. 9A,B). This impaired signaling response was seen in every stage of differentiation of Tim-3 expressing cells (FIG. 9C-E). Thus, Tim-3 expressing CD8$^+$ T cells exhibit a blunted change in phosphorylation of 'pre-activated' signaling proteins. This is consistent with the model recently proposed by Schweneker et al in which HIV-1 infection induces chronic activation of T cells resulting in enhanced basal phosphorylation and perturbed signaling in response to restimulation (37). The intracellular domain of Tim-3 contains 5 conserved tyrosine residues, but does not contain sequences corresponding to the ITIM consensus, and its downstream signaling targets remain unknown.

These data provide evidence that human Tim-3 acts to suppress effector functions of activated T cells in chronic viral infection. This complements and integrates previous studies which have identified an important role for Tim-3 in immunoregulation, and have implicated defective Tim-3 signaling in the pathogenesis of multiple sclerosis and other autoimmune diseases (38-40). In HIV-1 infection, the proportion of $CD8^+$ and $CD4^+$ T cells in peripheral blood that express Tim-3 can reach in excess of 70% and 30% respectively (in contrast to means of 28.5% and 17.6% in HIV-1-uninfected individuals). As these frequencies exceed the proportion of HIV-1-specific cells in the periphery, suppression of T cell function by Tim-3 likely contributes not only to the loss of functional virus-specific responses, but also to the impairment of responses to other antigens. This is supported by the present observations that a subset of CMV and EBV-specific $CD8^+$ T cells in chronic HIV-1-infected individuals express high levels of Tim-3, and is consistent with observations that HIV-1-infected individuals have reduced responses to recall antigens and vaccinations (41). The factors leading to this generalized expression of Tim-3 are not fully elucidated. The present data does however show a disproportionately high level of Tim-3 expression on HIV-1-specific $CD8^+$ T cells, consistent with the preferential dysfunction of HIV-1-specific $CD8^+$ T cells in chronic HIV-1 infection. Whether the fixation of escape mutations results in diminished Tim-3 expression on epitope-specific T cells and improvement in functionality, as has been described for PD-1 can be determined (42).

Figure 3A:
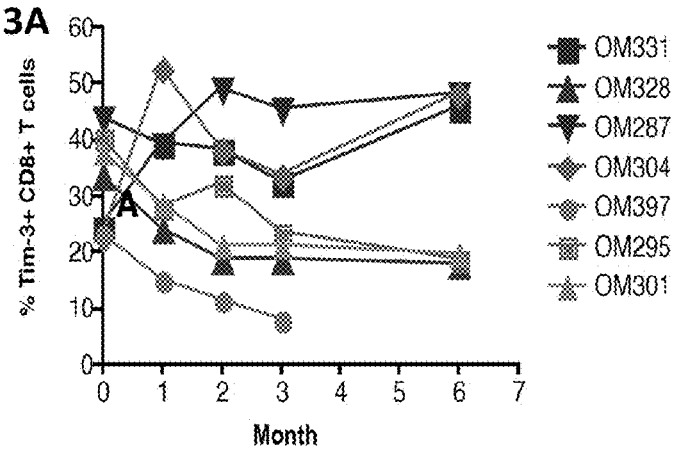
FIGS. 3A-3B show the effect of HAART on levels of Tim-3 expression in Chronic HIV-1 infection. Seven chronically HIV-1-infected individuals from the CIRC cohort were sampled at baseline and at 1, 2, 3 and 6 months post-initiation of HAART. Shown are (FIG. 3A) compiled Tim-3 expression on CD8$^+$ T cells versus month post-initiation of HAART (FIG. 3B) Tim-3 and CD38 expression levels as determined by flow cytometry, along with absolute CD4$^+$ T cell count and HIV-1 viral load clinical data. The 6 individuals followed for 6 months achieved undetectable viral loads (bDNA<50 copies/ml). The chart in panel (FIG. 3B) summarizes the p values obtained from a mixed-effects longitudinal analysis studying associations between Tim-3 expression on CD8+ T cells with: HIV-1 viral load, CD8$^+$ T cell activation as measured by CD38 expression (MFI), and absolute CD4$^+$ T cell count.
Figure 3B:
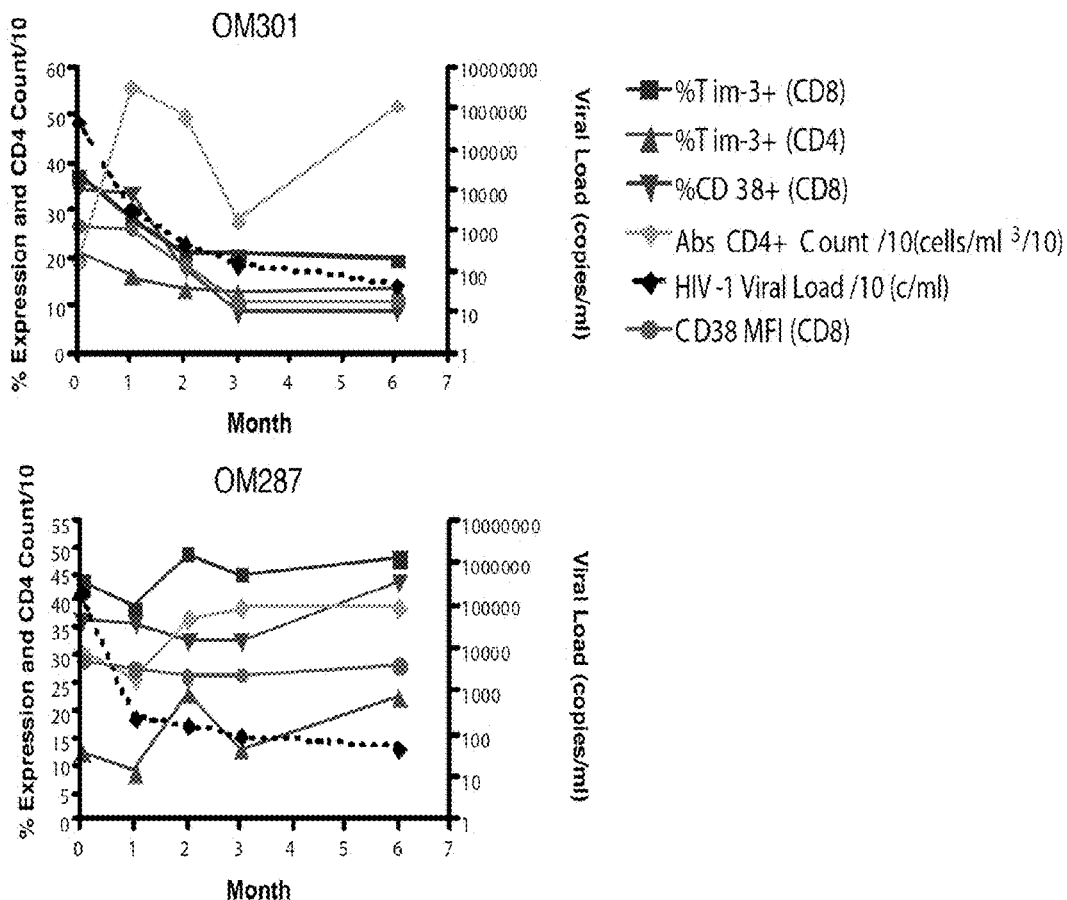

Reduction of Tim-3 expression upon initiation of HAART is correlated with levels of ongoing T cell activation (CD38 expression)—The effect of highly active antiretroviral therapy (HAART) on Tim-3 expression was studied in 7 chronically HIV-1-infected individuals at baseline and at 1, 2, 3 and 6 months post-initiation of HAART (FIG. 3). Four subjects with chronic infection demonstrated a steady decline in Tim-3 levels on both $CD4^+$ and $CD8^+$ T cells with HAART, while three subjects (OM 304, 331, 287) maintained high levels of Tim-3 expression despite achieving undetectable HIV-1 viral loads (<50 copies/ml bDNA) (FIG. 3a,b). In a mixed-effects longitudinal analysis it was observed that $CD8^+$ T cell activation, as measured by CD38 expression, was found to be significantly associated with Tim-3 expression over the period of HAART. Both the percentage of $CD8^+$ T cells expressing CD38, and the CD38 median fluorescence intensity on $CD8^+$ T cells each associated with higher Tim-3 percentages on $CD8^+$ T cells during therapy (0.38 (SE=0.11) percentage point higher Tim-3 expression on $CD8^+$ per each 1 percent higher CD38 expression on $CD8^+$ T cells (p=0.001; FIGS. 3b), and 0.7 (SE=0.19) percentage point higher Tim-3 expression on $CD8^+$ per each 1 unit higher CD38 MFI on $CD8^+$ T cells (p=0.001). These effects remained unaltered when adjusted for $CD4^+$ T cell count. In contrast, neither HIV-1 viral load (p=0.25) nor absolute $CD4^+$ T cell count (p=0.07), were significantly associated with Tim-3 expression post-HAART. Maintenance of high levels of Tim-3 expression in a subset of chronically HIV-1-infected individuals treated with HAART therapy is thus related to ongoing T cell activation (CD38 expression).

Recent data supporting that a dysregulation of the Tim-3 pathway may contribute to the pathology of multiple sclerosis highlights the importance of Tim-3 in regulating potentially harmful immune responses (38, 43). This situation is analogous to the considerations required in pursuing PD-1 as a therapeutic target. An important distinction of Tim-3 as a therapeutic target is its unique association with T cells that are impaired not only in their survival and proliferative potential, but also in their ability to produce cytokine. Thus, blockade of the Tim-3 pathway carries the novel potential to enhance not only the numbers of T cells in HIV-1 infection, but also to improve the functionality of both $CD8^+$ and $CD4^+$ T cells in HIV-1-infected individuals. Since a subset of subjects maintain high levels of Tim-3 expression despite seemingly effective HAART regimens, Tim-3 therapeutics may also play a role in reversing immune defects which persist with HAART.

The data presented herein clearly demonstrate that Tim-3 expression defines a distinct population of exhausted T cells from that of the recently identified PD-1 expressing population. This corroborates a recent study which reported that PD-1 expressing cells comprise only a sub-population of dysfunctional HIV-1-specific $CD8^+$ T cells in chronic progressors (44). The mechanisms leading to T cell exhaustion in the context of HIV-1 infection are clearly complex, and cannot be attributed to a single pathway. Further, it may be that there is an additive, or a synergistic, effect of simultaneously blocking both the Tim-3 and PD-1 pathways, which may allow for a more comprehensive reversal of T cell exhaustion, potentially leading to potent combination therapies.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

REFERENCES

1. X. Jin et al., *J Exp Med* 189, 991 (Mar. 15, 1999).
2. P. Motta et al., *Medicina* (B Aires) 62, 245 (2002).
3. O. O. Yang et al., *J Virol* 71, 3120 (April, 1997).
4. J. E. Schmitz et al., *Science* 283, 857 (Feb. 5, 1999).
5. C. Petrovas et al., *J Exp Med* 203, 2281 (Oct. 2, 2006).
6. C. L. Day et al., *Nature* 443, 350 (Sep. 21, 2006).
7. L. Trautmann et al., *Nat Med* 12, 1198 (October, 2006).
8. V. Appay et al., *J Exp Med* 192, 63 (Jul. 3, 2000).
9. M. A. Ostrowski et al., *J Immunol* 165, 6133 (Dec. 1, 2000).
10. M. T. Roos et al., *J Infect Dis* 182, 451 (August, 2000).
11. L. E. Gamadia, I. J. ten Berge, L. J. Picker, R. A. van Lier, *Nat Immunol* 3, 203 (March, 2002).
12. M. J. Deeths, R. M. Kedl, M. F. Mescher, *J Immunol* 163, 102 (Jul. 1, 1999).
13. E. L. Tham, P. Shrikant, M. F. Mescher, *J Immunol* 168, 1190 (Feb. 1, 2002).
14. D. Scott-Algara et al., *J Clin Immunol* 25, 57 (January, 2005).
15. A. R. Thomsen, O. Marker, *Scand J Immunol* 24, 137 (August, 1986).
16. P. Shankar et al., *Blood* 96, 3094 (Nov. 1, 2000).
17. L. A. Trimble, J. Lieberman, *Blood* 91, 585 (Jan. 15, 1998).
18. S. Kostense et al., *Eur J Immunol* 31, 677 (March, 2001).

19. L. Monney et al., Nature 415, 536 (Jan. 31, 2002).
20. C. Zhu et al., Nat Immunol 6, 1245 (December, 2005).
21. H. G. Zhu, Z. H. Feng, H. Geng, G. M. Zhang, *Xi Bao Yu Fen Zi Mian Yi Xue Za Zhi* 21, 403 (July, 2005).
22. A. Sanchez-Fueyo et al., *Nat Immunol* 4, 1093 (November, 2003).
23. C. A. Sabatos et al., *Nat Immunol* 4, 1102 (November, 2003).
24. J. V. Giorgi et al., *J Acquir Immune Defic Syndr* 6, 904 (August, 1993).
25. E. Cao et al., *Immunity* 26, 311 (March, 2007).
26. B. Emu et al., *J Virol* 79, 14169 (November, 2005).
27. V. Appay et al., *Nat Med* 8, 379 (April, 2002).
28. P. Champagne et al., *Nature* 410, 106 (Mar. 1, 2001).
29. O. D. Perez, G. P. Nolan, *Nat Biotechnol* 20, 155 (February, 2002).
30. J. Gerdes et al., Immunol 133, 1710 (1984)
31. B. Combadere et al., European Journal of immunology 30, 3598 (2000)
32. M. G. van Oijen et al., American journal of clinical pathology 110, 24 (1998)
33. Z. Grossman, W. E. Paul, *Nature medicine* 6, 976 (2000)
34. Z. Grossman et al., *Proceedings of the National Academy of Sciences of the United States of America* 95, 6314 (1998)
35. N. Sachsenberg et al., *The Journal of experimental medicine* 187, 1295 (1998)
36. K. E. Garrison et al., PLoS pathogens 3, e165 (2007)
37. M. Schweneker et al., Journal of Immunology 180, 6490 (2008)
38. K. Koguchi et al., The Journal of experimental medicine 203, 1413 (2006)
39. L. Yang et al., Journal of Immunology 180, 4409 (2008)
40. A. C. Anderson, D. E. Anderson, Current opinion in immunology 18, 665 (2006)
41. H. C. Lane et al., New England Journal of Medicine 313, 79 (1985)
42. H. Streeck et al., PLoS medicine 5, e100 (2008)
43. A. C. Anderson, et al., Science 318, 1141 (2007)
44. C. Wang, et al., Journal of Immunology 179, 8252 (2007)

TABLE 1

Tim-3-external nucleic acid sequence (SEQ ID NO: 1)
CCTCAGAAGTGGAATACAGAGCGGAGGTCGGTCAGAATGCCTATCTGCCC
TGCTTCTACACCCCAGCCGCCCCAGGGAACCTCGTGCCCGTCTGCTGGGG
CAAAGGAGCCTGTCCTGTGTTTGAATGTGGCAACGTGGTGCTCAGGACTG
ATGAAAGGGATGTGAATTATTGGACATCCAGATACTGGCTAAATGGGGAT
TTCCGCAAAGGAGATGTGTCCCTGACCATAGAGAATGTGACTCTAGCAGA
CAGTGGGATCTACTGCTGCCGGATCCAAATCCCAGGCATAATGAATGATG
AAAAATTTAACCTGAAGTTGGTCATCAAACCAGCCAAGGTCACCCCTGCA
CCGACTCGGCAGAGAGACTTCACTGCAGCCTTTCCAAGGATGCTTACCAC
CAGGGGACATGGCCCAGCAGAGACACAGACACTGGGGAGCCTCCCTGATA
TAAATCTAACACAAATATCCACATTGGCCAATGAGTTACGGGACTCTAGA
TTGGCCAATGACTTACGGGACTCTGGAGCAACCATCAGA Tim-3-external-translated amino acid sequence (SEQ ID NO: 2)
SEVEYRAEVGQNAYLPCFYTPAAPGNLVPVCWGKGACPVFECGNVVLRTD
ERDVNYWTSRYWLNGDFRKGDVSLTIENVTLADSGIYCCRIQIPGIMNDE
KFNLKLVIKPAKVTPAPTRQRDFTAAFPRMLTTRGHGPAETQTLGSLPDI
NLTQISTLANELRDSRLANDLRDSGATIR Tim-3-external-IgV-domain translated amino acid sequence (SEQ ID NO: 6)
SEVEYRAEVGQNAYLPCFYTPAAPGNLVPVCWGKGACPVFECGNVVLRTD
ERDVNYWTSRYWLNGDFRKGDVSLTIENVTLADSGIYCCRIQIPGIMN

The invention claimed is:

1. A method for inhibiting a viral infection in a subject in need thereof comprising administering an effective amount of an inhibitor of T-cell immunoglobulin and mucin domain-containing molecule 3 (Tim-3), wherein the inhibitor is a means for binding Tim-3, and wherein the viral infection is a human immunodeficiency virus (HIV) infection or a hepatitis C virus (HCV) infection, and wherein the Tim-3 to which the inhibitor binds has at least 90% sequence identity to SEQ ID NO: 2 or 6.

2. The method of claim 1, wherein the viral infection is a chronic viral infection.

3. The method of claim 1, further comprising administering an effective amount of an antigen expressed by a virus that causes a chronic infection.

4. The method of claim 3, wherein the chronic virus is human immunodeficiency virus type 1 (HIV-1) or hepatitis C virus (HCV).

5. The method of claim 1 wherein the viral infection is a human immunodeficiency virus (HIV) infection.

6. The method of claim 1 wherein the viral infection is a hepatitis C virus (HCV) infection.

7. The method of claim 1 wherein the means for binding Tim-3 comprises an anti-Tim-3 antibody that specifically binds to an amino acid sequence according to SEQ ID NO: 2 or 6.

* * * * *

SEQUENCE LISTING

<160> NUMBER OF SEQ ID NOS: 19

<210> SEQ ID NO 1
<211> LENGTH: 539
<212> TYPE: DNA
<213> ORGANISM: Homo sapiens

<400> SEQUENCE: 1
cctcagaagt ggaatacaga gcggaggtcg gtcagaatgc ctatctgccc tgcttctaca    60
ccccagccgc cccagggaac ctcgtgcccg tctgctgggg caaaggagcc tgtcctgtgt   120
ttgaatgtgg caacgtggtg ctcaggactg atgaaaggga tgtgaattat tggacatcca   180
gatactggct aaatggggat ttccgcaaag gagatgtgtc cctgaccata gagaatgtga   240
ctctagcaga cagtgggatc tactgctgcc ggatccaaat cccaggcata atgaatgatg   300
aaaaatttaa cctgaagttg gtcatcaaac cagccaaggt caccoctgca ccgactcggc   360 agagagactt cactgcagcc tttccaagga tgcttaccac caggggacat ggcccagcag   420
agacacagac actggggagc ctccctgata taaatctaac acaaatatcc acattggcca   480
atgagttacg ggactctaga ttggccaatg acttacggga ctctggagca accatcaga    539

<210> SEQ ID NO 2
<211> LENGTH: 179
<212> TYPE: PRT
<213> ORGANISM: Homo sapiens

<400> SEQUENCE: 2

Ser Glu Val Glu Tyr Arg Ala Glu Val Gly Gln Asn Ala Tyr Leu Pro

```
  1               5                  10                 15
Cys Phe Tyr Thr Pro Ala Ala Pro Gly Asn Leu Val Pro Val Cys Trp
             20                 25                 30

Gly Lys Gly Ala Cys Pro Val Phe Glu Cys Gly Asn Val Val Leu Arg
             35                 40                 45

Thr Asp Glu Arg Asp Val Asn Tyr Trp Thr Ser Arg Tyr Trp Leu Asn
             50                 55                 60

Gly Asp Phe Arg Lys Gly Asp Val Ser Leu Thr Ile Glu Asn Val Thr
 65                 70                 75                 80

Leu Ala Asp Ser Gly Ile Tyr Cys Cys Arg Ile Gln Ile Pro Gly Ile
                 85                 90                 95

Met Asn Asp Glu Lys Phe Asn Leu Lys Leu Val Ile Lys Pro Ala Lys
                100                105                110

Val Thr Pro Ala Pro Thr Arg Gln Arg Asp Phe Thr Ala Ala Phe Pro
            115                120                125

Arg Met Leu Thr Thr Arg Gly His Gly Pro Ala Glu Thr Gln Thr Leu
 130                135                140

Gly Ser Leu Pro Asp Ile Asn Leu Thr Gln Ile Ser Thr Leu Ala Asn
145                150                155                160

Glu Leu Arg Asp Ser Arg Leu Ala Asn Asp Leu Arg Asp Ser Gly Ala
                165                170                175

Thr Ile Arg

<210> SEQ ID NO 3
<211> LENGTH: 34
<212> TYPE: DNA
<213> ORGANISM: Artificial Sequence
<220> FEATURE:
<223> OTHER INFORMATION: Primer-Tim-3-extF

<400> SEQUENCE: 3
ttcggccggc cctcagaagt ggaatacaga gcgg                           34

<210> SEQ ID NO 4
<211> LENGTH: 38
<212> TYPE: DNA
<213> ORGANISM: Artificial Sequence
<220> FEATURE:
<223> OTHER INFORMATION: Primer-Tim-3-extR

<400> SEQUENCE: 4
tgagcggccg ctcatcatct gatggttgct ccagagtc                       38

<210> SEQ ID NO 5
<211> LENGTH: 301
<212> TYPE: PRT
<213> ORGANISM: Homo sapiens

<400> SEQUENCE: 5

Met Phe Ser His Leu Pro Phe Asp Cys Val Leu Leu Leu Leu Leu Leu
 1               5                  10                 15

Leu Leu Thr Arg Ser Ser Glu Val Glu Tyr Arg Ala Glu Val Gly Gln
             20                 25                 30

Asn Ala Tyr Leu Pro Cys Phe Tyr Thr Pro Ala Ala Pro Gly Asn Leu
             35                 40                 45

Val Pro Val Cys Trp Gly Lys Gly Ala Cys Pro Val Phe Glu Cys Gly
 50                 55                 60

Asn Val Val Leu Arg Thr Asp Glu Arg Asp Val Asn Tyr Trp Thr Ser
```

```
                65                  70                  75                  80
Arg Tyr Trp Leu Asn Gly Asp Phe Arg Lys Gly Asp Val Ser Leu Thr
                    85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
            115                 120                 125

Ile Lys Pro Ala Lys Val Thr Pro Ala Pro Thr Arg Gln Arg Asp Phe
        130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
        195                 200                 205

Ile Cys Ala Gly Leu Ala Leu Ala Leu Ile Phe Gly Ala Leu Ile Phe
    210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
        275                 280                 285

Gln Pro Ser Gln Pro Leu Gly Cys Arg Phe Ala Met Pro
    290                 295                 300

<210> SEQ ID NO 6
<211> LENGTH: 98
<212> TYPE: PRT
<213> ORGANISM: Homo sapiens

<400> SEQUENCE: 6

Ser Glu Val Glu Tyr Arg Ala Glu Val Gly Gln Asn Ala Tyr Leu Pro
1               5                   10                  15

Cys Phe Tyr Thr Pro Ala Ala Pro Gly Asn Leu Val Pro Val Cys Trp
                20                  25                  30

Gly Lys Gly Ala Cys Pro Val Phe Glu Cys Gly Asn Val Val Leu Arg
            35                  40                  45

Thr Asp Glu Arg Asp Val Asn Tyr Trp Thr Ser Arg Tyr Trp Leu Asn
        50                  55                  60

Gly Asp Phe Arg Lys Gly Asp Val Ser Leu Thr Ile Glu Asn Val Thr
65                  70                  75                  80

Leu Ala Asp Ser Gly Ile Tyr Cys Cys Arg Ile Gln Ile Pro Gly Ile
                85                  90                  95

Met Asn

<210> SEQ ID NO 7
<211> LENGTH: 9
<212> TYPE: PRT
<213> ORGANISM: Human immunodeficiency virus

<400> SEQUENCE: 7
```

Ser Leu Tyr Asn Thr Val Ala Thr Leu
1               5

<210> SEQ ID NO 8
<211> LENGTH: 22
<212> TYPE: DNA
<213> ORGANISM: Artificial Sequence
<220> FEATURE:
<223> OTHER INFORMATION: Primer-TBP-for

<400> SEQUENCE: 8
gggcattatt tgtgcactga ga                                              22

<210> SEQ ID NO 9
<211> LENGTH: 22
<212> TYPE: DNA
<213> ORGANISM: Artificial Sequence
<220> FEATURE:
<223> OTHER INFORMATION: Primer-TBP-rev

<400> SEQUENCE: 9
tagcagcacg gtatgagcaa ct                                              22

<210> SEQ ID NO 10
<211> LENGTH: 20
<212> TYPE: DNA
<213> ORGANISM: Artificial Sequence
<220> FEATURE:
<223> OTHER INFORMATION: Primer-GATA-3-for

<400> SEQUENCE: 10
tgcatgactc actggaggac                                                 20

<210> SEQ ID NO 11
<211> LENGTH: 20
<212> TYPE: DNA
<213> ORGANISM: Artificial Sequence
<220> FEATURE:
<223> OTHER INFORMATION: Primer-GATA-3-rev

<400> SEQUENCE: 11
tcagggagga catgtgtctg                                                 20

<210> SEQ ID NO 12
<211> LENGTH: 20
<212> TYPE: DNA
<213> ORGANISM: Artificial Sequence
<220> FEATURE:
<223> OTHER INFORMATION: Primer-T-bet-for

<400> SEQUENCE: 12
gaggctgagt ttcgagcagt                                                 20

<210> SEQ ID NO 13
<211> LENGTH: 20
<212> TYPE: DNA
<213> ORGANISM: Artificial Sequence
<220> FEATURE:
<223> OTHER INFORMATION: Primer-T-bet-rev

<400> SEQUENCE: 13
ctggcctcgg tagtaggaca                                                 20

<210> SEQ ID NO 14
<211> LENGTH: 20

```
<212> TYPE: DNA
<213> ORGANISM: Artificial Sequence
<220> FEATURE:
<223> OTHER INFORMATION: Primer-IFN-gamma-for

<400> SEQUENCE: 14
tccaagtgat ggctgaactg                                                 20

<210> SEQ ID NO 15
<211> LENGTH: 20
<212> TYPE: DNA
<213> ORGANISM: Artificial Sequence
<220> FEATURE:
<223> OTHER INFORMATION: Primer-IFN-gamma-rev

<400> SEQUENCE: 15
cttcgacctc gaaacagcat                                                 20

<210> SEQ ID NO 16
<211> LENGTH: 9
<212> TYPE: PRT
<213> ORGANISM: Cytomegalovirus

<400> SEQUENCE: 16

Asn Leu Val Pro Met Val Ala Thr Val
1               5

<210> SEQ ID NO 17
<211> LENGTH: 9
<212> TYPE: PRT
<213> ORGANISM: Epstein Barr viru

<400> SEQUENCE: 17

Gly Leu Cys Thr Leu Val Ala Met Leu
1               5

<210> SEQ ID NO 18
<211> LENGTH: 9
<212> TYPE: PRT
<213> ORGANISM: Human immunodeficiency virus

<400> SEQUENCE: 18

Ile Leu Lys Glu Pro Val His Gly Val
1               5

<210> SEQ ID NO 19
<211> LENGTH: 10
<212> TYPE: PRT
<213> ORGANISM: Cytomegalovirus

<400> SEQUENCE: 19

Thr Pro Arg Val Thr Gly Gly Gly Ala Met
1               5                   10
```